United States Patent
Barbee et al.

(10) Patent No.: US 10,267,790 B1
(45) Date of Patent: *Apr. 23, 2019

(54) SYSTEMS FOR BIOLOGICAL SAMPLE PROCESSING AND ANALYSIS

(71) Applicant: Ultima Genomics, Inc., Newark, CA (US)

(72) Inventors: Kristopher Barbee, Pleasanton, CA (US); Nathan Beckett, Oakland, CA (US); Denis Pristinski, Dublin, CA (US); Derek Schulte, Los Angeles, CA (US); Avishai Bartov, Hod-Hasharon (IL); Jamie Sullivan, Eugene, OR (US); Dumitru Brinza, Montara, CA (US); Abizar Lakdawalla, Los Altos Hills, CA (US); Steven Menchen, Fremont, CA (US); Gilad Almogy, Palo Alto, CA (US); Mark Pratt, Bozeman, MT (US)

(73) Assignee: ULTIMA GENOMICS, INC., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,441

(22) Filed: May 8, 2018

Related U.S. Application Data

(60) Provisional application No. 62/588,139, filed on Nov. 17, 2017, provisional application No. 62/623,743, (Continued)

(51) Int. Cl.
*G01N 33/543* (2006.01)
*C12Q 1/6874* (2018.01)
(Continued)

(52) U.S. Cl.
CPC .... *G01N 33/54366* (2013.01); *B01J 19/0046* (2013.01); *B01L 3/5023* (2013.01);
(Continued)

(58) Field of Classification Search
CPC ............ G01N 33/54366; B01J 19/0046; B01J 2219/00605; B01J 2219/00702;
(Continued)

(56) References Cited

U.S. PATENT DOCUMENTS

| 4,611,881 A | 9/1986 | Schmidt et al. |
| 5,216,247 A | 6/1993 | Wang et al. |

(Continued)

FOREIGN PATENT DOCUMENTS

| JP | 2000304688 A | 11/2000 |
| WO | WO-0039625 A2 | 7/2000 |
| WO | WO-0039625 A3 | 10/2000 |

OTHER PUBLICATIONS

Adessi et al. Solid phase DNA amplification: Charcterisation of primer attachment and amplification mechanisms, Nucl. Acids Res, 2000, 28(20):E87.

(Continued)

*Primary Examiner* — Samuel P Siefke
(74) *Attorney, Agent, or Firm* — Wilson, Sonsini, Goodrich & Rosati

(57) ABSTRACT

Provided are systems for biological sample processing and analysis. A system can comprise a substrate configured to rotate. The substrate can comprise an array configured to immobilize a biological analyte. A fluid flow unit comprising a fluid channel can be configured to dispense a solution comprising a plurality of probes. The solution may be directed, via centrifugal force, across the substrate during rotation of the substrate, to couple at least one of the plurality of probes with the biological analyte. A detector in (Continued)

optical communication with the array can be configured to detect one or more signals from the at least one probe coupled to the biological analyte.

50 Claims, 25 Drawing Sheets

Related U.S. Application Data filed on Jan. 30, 2018, provisional application No. 62/664,049, filed on Apr. 27, 2018.

(51) Int. Cl.
*C12Q 1/6809* (2018.01)
*C12Q 1/6825* (2018.01)
*B01L 3/00* (2006.01)
*B01J 19/00* (2006.01)

(52) U.S. Cl.
CPC ......... *C12Q 1/6809* (2013.01); *C12Q 1/6825* (2013.01); *C12Q 1/6874* (2013.01); *B01J 2219/00596* (2013.01); *B01J 2219/00605* (2013.01); *B01J 2219/00689* (2013.01); *B01J 2219/00702* (2013.01); *B01J 2219/00722* (2013.01); *B01L 2200/026* (2013.01); *B01L 2200/0647* (2013.01)

(58) Field of Classification Search
CPC .... B01J 2219/00596; B01J 2219/00689; B01J 2219/00722; B01L 3/5023; B01L 2200/026; B01L 2200/0647; C12Q 1/6825; C12Q 1/6809; C12Q 1/6874
See application file for complete search history.

(56) References Cited

U.S. PATENT DOCUMENTS

| 5,409,811 | A | 4/1995 | Tabor et al. |
| 5,641,658 | A | 6/1997 | Adams et al. |
| 5,674,716 | A | 10/1997 | Tabor et al. |
| 6,737,238 | B2 | 5/2004 | Suzuki et al. |
| 8,597,882 | B2 | 12/2013 | Corbett et al. |
| 9,891,177 | B2 | 2/2018 | Vazhaeparambil et al. |
| 2003/0193589 | A1 | 10/2003 | Lareau et al. |
| 2015/0125346 | A1 | 5/2015 | Schaff et al. |
| 2016/0032380 | A1 | 2/2016 | Craighead et al. |
| 2016/0097727 | A1 | 4/2016 | Vazhaeparambil et al. |

OTHER PUBLICATIONS

Brenner, et al. Gene expression analysis by massively parallel signature sequencing (MPSS) on microbead arrays. Nat Biotechnol. Jun. 2000;18(6):630-4.
Brenner et al. In vitro cloning of complex mixtures of DNA on microbeads: Physical separation of differentially expressed cDNAs, Proc. Natl. Acad. Sci. USA 2000, 97(4):1665-1670.
Co-pending U.S. Appl. No. 15/974,364, filed May 8, 2018.
Co-pending U.S. Appl. No. 15/974,543, filed May 8, 2018.
Dressman, et al. Transforming single DNA molecules into fluorescent magnetic particles for detection and enumeration of genetic variations. Proc Natl Acad Sci USA. 2003;100(15):8817-8822.
Lizardi, et al. Mutation detection and single-molecule counting using isothermal rolling-circle amplification. Nat Genet. Jul. 1998;19(3):225-32.
Mitra, et al. Digital genotyping and haplotyping with polymerase colonies. Proc Natl Acad Sci USA. 2003.100(10):15926-5931.
Mitra et al. Fluorescent in situ sequencing on polymerase colonies, Anal. Biochem, 320:55-65. (2003).
Pemov et al. DNA analysis with multiplex microarray-enhanced PCR, Nucl. Acids Res, 2005, 33(2):e11, pp. 1-9.
Reinartz, et al. Massively parallel signature sequencing (MPSS) as a tool for in-depth quantitative gene expression profiling in all organisms. Brief Funct Genomic Proteomic. Feb. 2002;1(1):95-104.
Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.
U.S. Appl. No. 15/974,543 Notice of Allowance dated Dec. 13, 2018.

SYSTEMS FOR BIOLOGICAL SAMPLE PROCESSING AND ANALYSIS

CROSS-REFERENCE

This application claims the benefit of U.S. Provisional Patent Application No. 62/588,139, filed Nov. 17, 2017, U.S. Provisional Patent Application No. 62/623,743, filed Jan. 30, 2018, and U.S. Provisional Patent Application No. 62/664,049, filed Apr. 27, 2018, each of which is entirely incorporated herein by reference.

BACKGROUND

Biological sample processing has various applications in the fields of molecular biology and medicine (e.g., diagnosis). For example, nucleic acid sequencing may provide information that may be used to diagnose a certain condition in a subject and in some cases tailor a treatment plan. Sequencing is widely used for molecular biology applications, including vector designs, gene therapy, vaccine design, industrial strain design and verification. Biological sample processing may involve a fluidics system and/or a detection system.

SUMMARY

Despite the prevalence of biological sample processing systems and methods, such systems and methods may have low efficiency that can be time-intensive and wasteful of valuable resources, such as reagents. Recognized herein is a need for methods and systems for sample processing and/or analysis with high efficiency.

The present disclosure provides methods and systems for sample processing and/or analysis.

In an aspect, provided is a system for analyzing a biological analyte, comprising: a substrate comprising an array configured to immobilize the biological analyte, wherein the substrate is configured to rotate with respect to a central axis; a fluid flow unit comprising a fluid channel configured to dispense a solution comprising a plurality of probes to the array, wherein during rotation of the substrate, the solution is directed centrifugally along a direction away from the central axis and brought in contact with the biological analyte under conditions sufficient to couple at least one probe of the plurality of probes to the biological analyte; a detector in optical communication with the array, wherein the detector is configured to detect one or more signals from the at least one probe coupled to the biological analyte; and one or more computer processors operatively coupled to the fluid flow unit and the detector, wherein the one or more computer processors are individually or collectively programmed to (i) direct the fluid flow unit to dispense the solution through the fluid channel to the array, which solution comprising the plurality of probes is directed centrifugally along a direction away from the central axis and brought in contact with the biological analyte during rotation of the substrate, and (ii) use the detector to detect the one or more signals from the at least one probe coupled to the biological analyte.

In some embodiments, the substrate is movable along the central axis. In some embodiments, the fluid channel is configured to dispense the solution when the substrate is at a first location along the central axis, and wherein the detector is configured to detect the one or more signals when the substrate is at a second location along the central axis, which second location is different from the first location. In some embodiments, wherein at the first location, the substrate is rotatable at a first angular velocity and, at the second location, the substrate is rotatable at a second angular velocity that is different than the first angular velocity.

In some embodiments, the system further comprises an additional fluid channel comprising configured to dispense an additional solution to the array, wherein the fluid channel and the additional fluid channel are fluidically isolated upstream from one another upstream of outlet ports of the fluid channel and the additional fluid channel.

In some embodiments, the system further comprises an optical imaging objective configured to be at least partially immersed in a fluid in contact with the substrate, which optical imaging objective is in optical communication with the detector.

In some embodiments, the system further comprises a container encircling the optical imaging objective, which container is configured to retain at least a portion of the fluid.

In some embodiments, the fluid channel does not contact the substrate.

In some embodiments, the array is a substantially planar array.

In some embodiments, the one or more computer processors are individually or collectively programmed to direct the fluid flow unit to dispense the solution through the fluid channel to the array prior to rotation of the substrate.

In some embodiments, the one or more computer processors are individually or collectively programmed to direct the fluid flow unit to dispense the solution through the fluid channel to the array when the substrate is undergoing rotation.

In some embodiments, the detector is configured to detect the one or more signals during rotation of the substrate. In some embodiments, the detector is configured to continuously scan the array along a nonlinear path during rotation of the substrate.

In some embodiments, the detector is configured to detect the one or more signals when the substrate is not rotating.

In some embodiments, the detector is an optical detector and wherein the one or more signals are one or more optical signals.

In some embodiments, the array comprises a plurality of individually addressable locations. In some embodiments, the plurality of individually addressable locations are individually physically accessible.

In some embodiments, the substrate is textured or patterned.

In some embodiments, the system further comprises a container comprising the substrate. In some embodiments, the system further comprises an environmental unit that is configured to regulate a temperature or a humidity of an environment of the container. In some embodiments, the detector comprises a time delay and integration (TDI) sensor or a pseudo-TDI rapid frame rate sensor. In some embodiments, the system further comprises an additional detector in optical communication with the array, wherein the detector and the additional detector are configured to scan the array along different paths. In some embodiments, the different paths are non-linear.

In some embodiments, the system further comprises one or more optics between, and in optical communication with, the array and the detector, wherein the one or more optics are configured to provide an optical magnification gradient across the array. In some embodiments, the optical magnification gradient is anamorphic.

In another aspect, provided is a system for sequencing a nucleic acid molecule, comprising: a substrate comprising a substantially planar array configured to immobilize a biological analyte, wherein the substrate is configured to rotate with respect to a central axis; a fluid flow unit comprising a fluid channel configured to dispense a solution comprising a plurality of probes to the substantially planar array, wherein during rotation of the substrate, the solution is directed across the substantially planar array and brought in contact with the biological analyte under conditions sufficient to couple at least one probe of the plurality of probes to the biological analyte; a detector in optical communication with the substantially planar array, wherein the detector is configured to detect one or more signals from the at least one probe coupled to the biological analyte; and one or more computer processors operatively coupled to the fluid flow unit and the detector, wherein the one or more computer processors are individually or collectively programmed to (i) direct the fluid flow unit to dispense the solution through the fluid channel to the array, which solution comprising the plurality of probes is directed across the substantially planar array and brought in contact with the biological analyte during rotation of the substrate, and (ii) use the detector to detect the one or more signals from the at least one probe coupled to the biological analyte.

In some embodiments, the system further comprises an optical imaging objective configured to be at least partially immersed in a fluid in contact with the substrate, which optical imaging objective is in optical communication with the detector. The fluid may be confined or controlled, such as by using an electrical field controlling the hydrophobicity of one or more of regions on the substrate and a fluid enclosure.

In some embodiments, the detector comprises a time delay and integration (TDI) sensor or a pseudo-TDI rapid frame rate sensor.

In some embodiments, the detector is configured to detect the one or more signals during rotation of the substrate. In some embodiments, the detector is configured to continuously scan the array along a nonlinear path during rotation of the substrate.

In another aspect, provided is a method for processing a biological analyte, comprising: (a) providing a substrate comprising an array having immobilized thereto the biological analyte, wherein the substrate is rotatable with respect to a central axis; (b) directing a solution comprising a plurality of probes across the substrate and in contact with the biological analyte during rotation of the substrate, wherein the solution is directed centrifugally along a direction away from the central axis; (c) subjecting the biological analyte to conditions sufficient to conduct a reaction between at least one probe of the plurality of probes and the biological analyte, to couple the at least one probe to the biological analyte; and (d) detecting one or more signals from the at least one probe coupled to the biological analyte, thereby analyzing the biological analyte.

In some embodiments, the biological analyte is a nucleic acid molecule, and wherein analyzing the biological analyte comprises identifying a sequence of the nucleic acid molecule. In some embodiments, the plurality of probes is a plurality of nucleotides. In some embodiments, (c) comprises subjecting the nucleic acid molecule to a primer extension reaction under conditions sufficient to incorporate at least one nucleotide from the plurality of nucleotides into a growing strand that is complementary to the nucleic acid molecule. In some embodiments, in (d), the one or more signals are indicative of incorporation of the at least one nucleotide. In some embodiments, the plurality of nucleotides comprise nucleotide analogs. In some embodiments, the plurality of nucleotides is of a first canonical base type. In some embodiments, the method further comprises repeating (b) and (c) with an additional plurality of nucleotides that are of a second canonical base type, wherein the second canonical base type is different than the first canonical base type. In some embodiments, the plurality of probes is a plurality of oligonucleotide molecules.

In some embodiments, the biological analyte is a nucleic acid molecule, and (c) comprises conducting a complementarity binding reaction between the at least one probe and the nucleic acid molecule to identify a presence of homology between the at least one probe and the biological analyte in (d).

In some embodiments, the detecting in (d) is conducted using a sensor that continuously scans the array along a nonlinear path during rotation of the substrate.

In some embodiments, the method further comprises, prior to (b), (i) dispensing the solution on the substrate when the substrate is stationary, and (ii) subjecting the substrate to rotation to direct the solution across the array.

In some embodiments, the method further comprises (i) subjecting the substrate to rotation prior to (b), and (ii) while the substrate is rotating, dispensing the solution on the substrate.

In some embodiments, the method further comprises repeating (b)-(d) with an additional plurality of probes that is different than the plurality of probes.

In some embodiments, the fluid viscosity of the solution or a rotational velocity of the substrate is selected to yield a predetermined thickness of a layer of the solution adjacent to the array.

In some embodiments, the biological analyte is immobilized to the array via a linker.

In some embodiments, the biological analyte is coupled to a bead, which bead is immobilized to the array.

In some embodiments, the solution is directed to the array using one or more dispensing nozzles that are directed at or in proximity to the central axis of the substrate.

In some embodiments, the array comprises a plurality of individually addressable locations, and wherein the biological analyte is disposed at a given individually addressable location of the plurality of individually addressable locations.

In some embodiments, the array has immobilized thereto one or more additional biological analytes.

In some embodiments, the substrate is textured or patterned.

In some embodiments, the one or more signals include one or more optical signals.

In some embodiments, the method further comprises terminating rotation of the substrate prior to detecting the one or more signals in (d).

In some embodiments, (b) and/or (c) is performed while the substrate is rotated at a first angular velocity and (d) is performed while the substrate is rotated at a second angular velocity that is different than the first angular velocity.

In some embodiments, the substrate is movable with respect to the central axis, and wherein (b) and/or (c) is performed when the substrate is at a first location of the central axis and (d) is performed when the substrate is at a second location of the central axis, which second location is different from the first location. In some embodiments, at the first location the substrate rotates at a first angular velocity and at the second location the substrate rotates at a second angular velocity that is different than the first angular velocity.

In some embodiments, the array is a substantially planar array.

In another aspect, provided is a method for processing a biological analyte, comprising: (a) providing a substrate comprising a substantially planar array having immobilized thereto the biological analyte, wherein the substrate is rotatable with respect to a central axis; (b) directing a solution comprising a plurality of probes across the substantially planar array and in contact with the biological analyte during rotation of the substrate; (c) subjecting the biological analyte to conditions sufficient to conduct a reaction between at least one probe of the plurality of probes and the biological analyte, to couple the at least one probe to the biological analyte; and (d) detecting one or more signals from the at least one probe coupled to the biological analyte, thereby analyzing the biological analyte.

In some embodiments, the biological analyte is a nucleic acid molecule, and wherein analyzing the biological analyte comprises identifying a sequence of the nucleic acid molecule.

In some embodiments, the detecting in (d) is conducted using a sensor that continuously scans the substantially planar array along a nonlinear path during rotation of the substrate.

In some embodiments, the substantially planar array comprises a plurality of individually addressable locations, and wherein the biological analyte is disposed at a given individually addressable location of the plurality of individually addressable locations.

In another aspect, provided is a method for analyte detection or analysis, comprising: (a) rotating an open substrate about a central axis, the open substrate having an array of immobilized analytes thereon; (b) delivering a solution having a plurality of probes to a region proximal to the central axis to introduce the solution to the open substrate; (c) dispersing the solution across the open substrate at least by centrifugal force such that at least one of the plurality of probes binds to at least one of the immobilized analytes to form a bound probe; and (d) using a detector to detect at least one signal from the bound probe via continuous rotational area scanning of the open substrate.

In some embodiments, the continuous rotational area scanning compensates for velocity differences at different radial positions of the array with respect to the central axis within a scanned area. In some embodiments, the continuous rotational area scanning comprises using an optical imaging system having an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the continuous rotational area scanning comprises reading two or more regions on the open substrate at two or more scan rates, respectively, to at least partially compensate for tangential velocity differences in the two or more regions.

In some embodiments, (d) further comprises using an immersion objective lens in optical communication with the detector and the open substrate to detect the at least one signal, which immersion objective lens is in contact with a fluid that is in contact with the open substrate. In some embodiments, the fluid is in a container, and an electric field is used to regulate a hydrophobicity of one or more surfaces of the container to retain at least a portion of the fluid contacting the immersion objective lens and the open substrate.

In some embodiments, the continuous rotational area scanning is performed in a first environment having a first operating condition, and wherein the delivering of the solution is performed in a second environment having a second operating condition different from the first operating condition.

In some embodiments, the immobilized analytes comprise nucleic acid molecules, wherein the plurality of probes comprises fluorescently labeled nucleotides, and wherein at least one of the fluorescently labeled nucleotides binds to at least one of the nucleic acid molecules via nucleotide complementarity binding.

In some embodiments, the open substrate is substantially planar.

In another aspect, provided is an apparatus for analyte detection or analysis, comprising: a housing configured to receive an open substrate having an array of immobilized analytes thereon; one or more dispensers configured to deliver a solution having a plurality of probes to a region proximal to a central axis of the open substrate; a rotational unit configured to rotate the open substrate about a central axis to thereby disperse the solution across the open substrate at least by centrifugal force, such that at least one of the plurality of probes binds to at least one of the analytes to form a bound probe; and a detector configured to detect at least one signal from the bound probe via continuous rotational area scanning of the open substrate.

In some embodiments, the detector is configured to compensate for velocity differences at different radial positions of the array with respect to the central axis within a scanned area. In some embodiments, the one or more optics are configured to generate an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the apparatus further comprises a processor configured to adjust the anamorphic magnification gradient to compensate for different imaged radial positions with respect to the central axis.

In some embodiments, the detector is configured to scan two or more regions on the open substrate at two or more scan rates, respectively, to at least partially compensate for tangential velocity differences in the two or more regions.

In some embodiments, the detector comprises a sensor and one or more optics in optical communication with the open substrate.

In some embodiments, the apparatus further comprises an immersion objective lens in optical communication with the detector and the open substrate, which immersion objective lens is configured to be in contact with a fluid that is in contact with the open substrate. In some embodiments, the apparatus further comprises a container configured to retain the fluid and an electric field application unit configured to regulate a hydrophobicity of one or more surfaces of the container to retain at least a portion of the fluid contacting the immersion objective lens and the open substrate. In some embodiments, the immersion objective lens is configured to separate a first environment from a second environment, wherein the first environment and second environment have different operating conditions. In some embodiments, the immersion objective lens forms a seal between the first environment and the second environment.

In some embodiments, the detector is configured to detect the at least one signal from the bound probe in a non-linear scanning path across the open substrate. In some embodiments, non-linear scanning path is a substantially spiral scanning path or a substantially ring-like scanning path.

In another aspect, provided is a computer-readable medium comprising non-transitory instructions stored thereon, which when executed cause one or more computer processors to implement a method for analyte detection or analysis, the method comprising: rotating an open substrate about a central axis, the open substrate having an array of immobilized analytes thereon; delivering a solution having a plurality of probes to a region proximal to the central axis, to introduce the solution to the open substrate; dispersing the solution across the open substrate at least by centrifugal force such that at least one of the plurality of probes binds to at least one of the immobilized analytes to form a bound probe; and using a detector to detect at least one signal from the bound probe via continuous rotational area scanning of the open substrate.

In some embodiments, the method further comprises using an immersion objective lens in optical communication with the detector and the open substrate to detect the at least one signal, which immersion objective lens is in contact with a fluid that is in contact with the open substrate. In some embodiments, the method further comprises using an electric field to regulate a hydrophobicity of one or more surfaces of a container to retain at least a portion of the fluid contacting the immersion objective lens and the open substrate.

In some embodiments, the immobilized analytes comprise nucleic acid molecules, wherein the plurality of probes comprises fluorescently labeled nucleotides, and wherein at least one of the fluorescently labeled nucleotides binds to at least one of the nucleic acid molecules via a primer extension reaction.

In some embodiments, the continuous rotational area scanning compensates for velocity differences at different radial positions of the array with respect to the central axis within a scanned area. In some embodiments, the continuous rotational area scanning comprises using an optical imaging system having an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the method further comprises adjusting the anamorphic magnification gradient to compensate for different imaged radial positions with respect to the central axis. In some embodiments, the detector is configured to scan two or more regions on the open substrate at two or more scan rates, respectively, to at least partially compensate for tangential velocity differences in the two or more imaged regions.

In some embodiments, the continuous rotational area scanning comprises using an algorithmic compensation for velocity differences substantially perpendicular to a scanning direction along the open substrate.

In some embodiments, the detector is configured to detect the at least one signal from the bound probe in a non-linear scanning path across the open substrate.

In another aspect, provided is a method for sequencing a nucleic acid molecule, comprising: (a) providing a substrate comprising a planar array having immobilized thereto the nucleic acid molecule, wherein the substrate is configured to rotate with respect to an axis; (b) directing a solution comprising a plurality of nucleotides across the planar array during rotation of the substrate; (c) subjecting the nucleic acid molecule to a primer extension reaction under conditions sufficient to incorporate at least one nucleotide from the plurality of nucleotides into a growing strand that is complementary to the nucleic acid molecule; and (d) detecting a signal indicative of incorporation of the at least one nucleotide, thereby sequencing the nucleic acid molecule.

The method may further comprise, prior to (b), (i) dispensing the solution on the substrate when the substrate is stationary, and (ii) subjecting the substrate to rotation to direct the solution across the planar array. The method may further comprise (i) subjecting the substrate to rotation prior to (b), and (ii) while the substrate is rotating, dispensing the solution on the substrate. The method may further comprise repeating (b)-(d) one or more times to identify one or more additional signals indicative of incorporation of one or more additional nucleotides, thereby sequencing the nucleic acid molecule.

Different solutions may be directed to the planar array during rotation of the substrate for consecutive cycles. The rotation may yield centrifugal forces that subject the solution to flow over the planar array. A layer thickness of the planar array may be engineered based on adjusting fluid viscosity. A first fluid having a first viscosity may be used for generating a layer with the nucleic acid molecule on the planar array and a second fluid having a second viscosity may be used for washing the planar array. The first viscosity may be different from the second viscosity. The first viscosity may be controlled by controlling a temperature of the first fluid. The second viscosity may be controlled by controlling a temperature of the second fluid.

The planar array may comprise a linker that is coupled to the nucleic acid sample. The nucleic acid sample may be coupled to a bead, which bead is immobilized to the planar array.

The planar array may be in fluid communication with at least one sample inlet and at least one sample outlet. The solution may be directed to the planar array using one or more dispensing nozzles. The one or more nozzles may be directed at or in proximity to a center of the substrate.

The method may further comprise recycling a subset of the solution that has contacted the substrate. Recycling may comprise collecting, filtering, and reusing the subset of the solution. The filtering may be molecular filtering.

The planar array may comprise a plurality of individually addressable locations. The planar array may be textured. The planar array may be a patterned array.

The signal may be an optical signal. The signal may be a fluorescent signal.

The method may further comprise terminating rotation of the substrate prior to detecting the signal in (d). The signal in (d) may be detected while the substrate is rotating.

The operations (b) and/or (c) may be performed at a first a location and (d) may be performed at a second location that is different from the first location. The first location may comprise a first processing bay and the second location may comprise a second processing bay that is different from the second location. The first location may comprise a first rotating spindle interior to a second rotating spindle and the second location may comprise the second rotating spindle. The first location may comprise a first rotating spindle exterior to a second rotating spindle and the second location may comprise the second rotating spindle. The first rotating spindle and second rotating spindle may be configured to rotate at different angular velocities. The operation (b) may be performed at the first location. The operation (c) may be performed at the second location. The operation (c) may be performed at the first location.

The method may further comprise transferring the substrate between the first location and the second location. The operations (b) and/or (c) may be performed while the substrate is rotated at a first angular velocity and (d) may be performed while the substrate is rotated at a second angular velocity that is different from the first angular velocity. The first angular velocity may be less than the second angular velocity. The first angular velocity may be between 0 revolutions per minute (rpm) and 100 rpm. The second angular velocity may be between 100 rpm and 5,000 rpm. The operation (b) may be performed while the substrate is rotated at the first angular velocity. The operation (c) may be performed while the substrate is rotated at the second angular velocity. The operation (c) may be performed while the substrate is rotated at the first angular velocity.

In an aspect, a method for sequencing a nucleic acid molecule may comprise: (a) providing a substrate comprising an array having immobilized thereto the nucleic acid molecule, wherein the substrate is configured to rotate with respect to an axis; (b) directing a solution comprising a plurality of natural nucleotides and/or non-natural nucleotides across the array during rotation of the substrate; (c) subjecting the nucleic acid molecule to a primer extension reaction under conditions sufficient to incorporate at least one nucleotide from the plurality of natural nucleotides and non-natural nucleotides into a growing strand that is complementary to the nucleic acid molecule; and (d) detecting a signal indicative of incorporation of the at least one nucleotide, thereby sequencing the nucleic acid molecule.

The method may further comprise, prior to (b), (i) dispensing the solution on the substrate when the substrate is stationary, and (ii) subjecting the substrate to rotation to direct the solution to the array. The method may further comprise (i) subjecting the substrate to rotation prior to (b), and (ii) while the substrate is rotating, dispensing the solution on the substrate. The method may further comprise, subsequent to (c), modifying the at least one nucleotide. The modifying may comprise labeling the at least one nucleotide. The at least one nucleotide may be cleavably labeled. The method may further comprise, subsequent to (d), cleaving or modifying a label of the at least one nucleotide. The method may further comprise repeating (b)-(d) one or more times to identify one or more additional signals indicative of incorporation of one or more additional nucleotides, thereby sequencing the nucleic acid molecule.

Different solution may be directed to the array during rotation of the substrate for consecutive cycles. Subsequent to (d), and prior to a next iteration of (b), the at least one nucleotide may be modified. The rotation may yield centrifugal forces that subject the solution to flow over the array. A layer thickness of the array may be engineered based on fluid viscosity. A first fluid having a first viscosity may be used for generating a layer with the nucleic acid molecule on the array and a second fluid having a second viscosity may be used for washing the array. The first viscosity may be different from the second viscosity. The first viscosity may be controlled by controlling a temperature of the first fluid. The second viscosity may be controlled by controlling a temperature of the second fluid.

The array may comprise a linker that is coupled to the nucleic acid sample. The nucleic acid sample may be coupled to a bead, which bead is immobilized to the array.

The array may be in fluid communication with at least one sample inlet and at least one sample outlet. The solution may be directed to the array using one or more dispensing nozzles. The one or more nozzles may be directed at or in proximity to a center of the substrate.

The method may further comprise recycling a subset of the solution that has contacted the substrate. Recycling may comprise collecting, filtering, and reusing the subset of the solution. The filtering may be molecular filtering.

The array may comprise a plurality of individually addressable locations. The array may be planar. The array may be textured. The array may be a patterned array.

The signal may be an optical signal. The signal may be a fluorescent signal.

The method may further comprise, prior to (b), subjecting the substrate to rotation with respect to the axis. The method may further comprise terminating rotation of the substrate prior to detecting the signal in (d). The signal in (d) may be detected while the substrate is rotating.

The operations (b) and/or (c) may be performed at a first location and (d) may be performed at a second location that is different from the first location. The first location may comprise a first processing bay and the second location may comprise a second processing bay that is different from the first processing bay. The first location may comprise a first rotating spindle interior to a second rotating spindle and the second location may comprise the second rotating spindle. The first location may comprise a first rotating spindle exterior to a second rotating spindle and the second location may comprise the second rotating spindle. The first rotating spindle and second rotating spindle may be configured to rotate at different angular velocities. The operation (b) may be performed at the first location. The operation (c) may be performed at the second location. The operation (c) may be performed at the first location.

The method may further comprise transferring the substrate between the first location and the second location. The operations (b) and/or (c) may be performed while the substrate is rotated at a first angular velocity and (d) may be performed while the substrate is rotated at a second angular velocity that is different from the first angular velocity. The first angular velocity may be less than the second angular velocity. The first angular velocity may be between 0 rpm and 100 rpm. The second angular velocity may be between 100 rpm and 5,000 rpm. The operation (b) may be performed while the substrate is rotated at the first angular velocity. The operation (c) may be performed while the substrate is rotated at the second angular velocity. The operation (c) may be performed while the substrate is rotated at the first angular velocity.

In an aspect, a system for sequencing a nucleic acid molecule may comprise: a substrate comprising an array configured to immobilize the nucleic acid molecule, wherein the substrate is configured to (i) rotate with respect to an axis and (ii) undergo a change in relative position with respect to a longitudinal axis; a first fluid channel comprising a first fluid outlet port that is configured to dispense a first fluid to the array; a second fluid channel comprising a second fluid outlet port that is configured to dispense a second fluid to the array, wherein the first fluid channel and the second fluid channel are fluidically isolated upstream of the first fluid outlet port; and a detector configured to detect a signal from the array.

The first fluid outlet port and the second fluid outlet port may be external to the substrate. The first fluid outlet port and the second fluid outlet port may not contact the substrate. The first fluid outlet port and the second fluid outlet port may be nozzles.

The axis may be substantially parallel with the longitudinal axis. The longitudinal axis may be coincident with the axis. The longitudinal axis may be substantially perpendicular to a surface of the substrate. The relative position of the substrate may be configured to alternate between at least a first position and a second position with respect to the longitudinal axis.

The system may further comprise (i) a third fluid channel comprising a first fluid inlet port located at a first level of the longitudinal axis, wherein the first fluid inlet port is downstream of and in fluid communication with the substrate when the substrate is in the first relative position, and (ii) a fourth fluid channel comprising a second fluid inlet port located at a second level of the longitudinal axis, wherein the second fluid inlet port is downstream of and in fluid communication with the substrate when the substrate is in the relative second position. The third fluid channel may be in fluid communication with the first fluid channel and the fourth fluid channel may be in fluid communication with the second fluid channel. The substrate may be configured to have (i) the first relative position prior to, during, or subsequent to receiving the first fluid from the first fluid outlet port and (ii) the second relative position prior to, during, or subsequent to receiving the second fluid from the second fluid outlet port. The third fluid channel and the first fluid channel may define at least part of a first cyclic fluid flow path and the fourth fluid channel and the second fluid channel may define at least part of a second cyclic fluid flow path. At least one of the first cyclic fluid flow path and the second cyclic fluid flow path may comprise a filter. The filter may be a molecular filter.

The system may further comprise a shield that prevents fluid communication between the substrate and (i) the second fluid inlet port when the substrate is in the first position and (ii) the first fluid inlet port when the substrate is in the second position. The substrate may be translatable along the longitudinal axis. The substrate may be stationary along the longitudinal axis. At least one of a first axis of the first fluid outlet port and a second axis of the second fluid outlet port may be substantially coincident with the axis. At least one of a first axis of the first fluid outlet port and a second axis of the second fluid outlet port may be substantially parallel to the axis.

The first fluid and the second fluid may comprise different types of reagents. The first fluid may comprise a first type of nucleotide or nucleotide mixture and the second fluid may comprise a second type of nucleotide or nucleotide mixture. The first fluid or the second fluid may comprise a washing reagent.

The detector may be configured to detect the signal from the substrate during rotation of the substrate. The detector may be configured to detect the signal from the substrate when the substrate is not rotating.

The signal may be an optical signal. The signal may be a fluorescent signal.

The first fluid outlet port may be configured to dispense the first fluid to the array during rotation of the substrate. The second fluid outlet port may be configured to dispense the second fluid to the array during rotation of the substrate. The first fluid outlet port and the second fluid outlet port may be configured to dispense at non-overlapping times. The substrate may be configured to rotate with at least one of (i) different speeds and (ii) different number of rotations when the first fluid outlet port dispenses and when the second fluid outlet port dispenses. During the rotation, the array may be configured to direct the first fluid in a substantially radial direction away from the axis. The first fluid outlet port may be configured to dispense the first fluid to the array during more than one full rotation of the substrate.

The array may comprise a plurality of individually addressable locations. The array may comprise a plurality of individually addressable locations. The array may comprise a linker that is coupled to the nucleic acid sample. The nucleic acid sample may be coupled to a bead, which bead is immobilized to the array. The array may be textured. The array may be a patterned array. The array may be planar.

In an aspect, a system for sequencing a nucleic acid molecule may comprise: a substrate comprising a planar array configured to immobilize the nucleic acid molecule, wherein the substrate is configured to rotate with respect to an axis; a fluid flow unit configured to direct a solution comprising a plurality of nucleotides to the planar array during rotation of the substrate; a detector in sensing communication with the planar array; and one or more computer processors operatively coupled to the fluid flow unit and the detector, wherein the one or more computer processors are individually or collectively programmed to (i) direct the fluid flow unit to direct the solution comprising the plurality of nucleotides across the planar array during rotation of the substrate; (ii) subject the nucleic acid molecule to a primer extension reaction under conditions sufficient to incorporate one or more nucleotides from the plurality of nucleotides into a growing strand that is complementary to the nucleic acid molecule; and (iii) use the detector to detect one or more signals indicative of incorporation of the at one or more nucleotides, thereby sequencing the nucleic acid molecule.

In an aspect, a system for sequencing a nucleic acid molecule may comprise: a substrate comprising an array configured to immobilize the nucleic acid molecule, wherein the substrate is configured to rotate with respect to an axis; a fluid flow unit configured to direct a solution comprising a plurality of nucleotides to the array during rotation of the substrate, wherein the plurality of nucleotides comprises natural nucleotides and/or non-natural nucleotides; a detector in sensing communication with the planar array; and one or more computer processors operatively coupled to the fluid flow unit and the detector, wherein the one or more computer processors are individually or collectively programmed to (i) direct the fluid flow unit to direct the solution comprising the plurality of nucleotides across the array during rotation of the array; (ii) subject the nucleic acid molecule to a primer extension reaction under conditions sufficient to incorporate one or more nucleotides of the plurality of nucleotides into a growing strand that is complementary to the nucleic acid molecule; and (iii) use the detector to detect one or more signals indicative of incorporation of the one or more nucleotides, thereby sequencing the nucleic acid molecule.

In an aspect, an optical system for continuous area scanning of a substrate during rotational motion of the substrate, wherein the rotational motion is with respect to an axis of the substrate, may comprise: a focal plane segmented into a plurality of regions; one or more sensors in optical communication with the plurality of regions; and a controller operatively coupled to the one or more sensors, wherein the controller is programmed to process optical signals from each region of the plurality of regions with independent clocking during the rotational motion, wherein the independent clocking is based at least in part on a distance of each region from a projection of the axis and an angular velocity of the rotational motion.

The focal plane may be segmented into the plurality of regions along an axis substantially normal to a projected direction of the rotational motion. The focal plane may be segmented into the plurality of regions along an axis parallel to a projected direction of the rotational motion. The focal plane may be optically segmented.

A given sensor of the one or more sensors may be configured to process each region of the plurality of regions with independent clocking during the rotational motion. The one or more sensors may be a plurality of sensors, wherein each of the plurality of sensors is in optical communication with a different region of the plurality of regions, and wherein the controller is configured to process optical signals from each of the plurality of regions with independent clocking during the rotational motion. The one or more sensors may comprise one or more time delay and integration (TDI), pseudo-TDI rapid frame rate, charge coupled device (CCD), or complementary metal oxide semiconductor (CMOS) detectors. The independent clocking may comprise TDI line rate or pseudo-TDI frame rate.

One or more of the sensors may be configured to be in optical communication with at least 2 of the plurality of regions in the focal plane. One or more of the sensors may comprise a plurality of segments. Each segment of the plurality of segments may be in optical communication with a region of the plurality of regions. Each segment of the plurality of segments may be independently clocked. The independent clocking of a segment may correspond to a velocity of an image in an associated region of the focal plane.

The optical system may further comprise an optical imaging objective configured to be immersed in a fluid. The optical system may further comprise an enclosure encircling the optical imaging objective. The optical system may further comprise a fluidic line coupled to the enclosure, the fluidic line configured to provide a fluid to the enclosure. The fluid may be in contact with the substrate. The fluid may be confined or controlled, such as by using an electrical field controlling the hydrophobicity of one or more of regions on the substrate and/or a fluid enclosure.

In an aspect, an optical system for imaging a substrate during rotational motion of the substrate, wherein the rotational motion is with respect to an axis of the support, may comprise: a sensor; and an optical element in optical communication with the sensor, wherein the optical element is configured to direct optical signals from the substrate to the sensor, and wherein at least one of the sensor and the optical element is configured to generate an optical magnification gradient across the detector along a direction substantially perpendicular to a projected direction of the rotational motion. The system may further comprise a controller operatively coupled to the detector and the optical element, wherein the controller is programmed to direct adjustment of at least one of the sensor and the optical element to generate the optical magnification gradient across the sensor along the direction substantially perpendicular to a projected direction of the rotational motion.

The optical element may be a lens. The controller may be programmed to direct adjustment of at least one of the sensor and the optical element to produce an anamorphic optical magnification gradient. A ratio of (i) a first optical magnification at a first radial position of a field dimension having a least distance in the field dimension from a projection of the axis to (ii) a second optical magnification at a second radial position of the field dimension having a greatest distance in the field dimension from the projection of the axis may be substantially equal to a ratio of the greatest distance to the least distance. The optical magnification gradient may be generated by rotation of the optical element and a focal plane substantially perpendicular to the projected direction of the rotational motion. The controller may be programmed to direct rotation of the optical element. The controller may be programmed to direct adjustment the gradient of magnification based at least in part on a radial range of a field dimension relative to a projection of the axis. The controller may be programmed to subject the rotational motion to the substrate.

The optical system may further comprise an optical imaging objective configured to be immersed in a fluid. The optical system may further comprise an enclosure encircling the optical imaging objective. The optical system may further comprise a fluidic line coupled to the enclosure, the fluidic line configured to provide a fluid to the enclosure. The fluid may be in contact with the substrate.

In an aspect, an optical system for imaging a substrate during rotational motion of the substrate, wherein the rotational motion is with respect to an axis of the support, may comprise: a plurality of sensors, each sensor of the plurality of sensors in optical communication with the substrate; and a controller operatively coupled to each sensor of the plurality of sensors, wherein the controller is programmed to direct each sensor of the plurality of sensors along an imaging path, wherein an imaging path for one or more sensors of the plurality of sensors is distinct from an imaging path of another sensor of the plurality of sensors. The controller may be programmed to direct each sensor of the plurality of sensors along an imaging path having a spiral shape or a ring shape. Each sensor of the plurality of sensors may be configured to receive light having a wavelength in a predetermined wavelength range.

The optical system may further comprise an optical imaging objective configured to be immersed in a fluid. The optical system may further comprise an enclosure encircling the optical imaging objective. The optical system may further comprise a fluidic line coupled to the enclosure, the fluidic line configured to provide a fluid to the enclosure.

In an aspect, a method for processing an analyte may comprise: (a) providing a substrate comprising a planar array having immobilized thereto said analyte, wherein said substrate is configured to rotate with respect to an axis; (b) directing a solution comprising a plurality of adaptors across said planar array during rotation of said substrate; (c) subjecting said analyte to conditions sufficient to cause a reaction between said analyte and said plurality of adaptors; and (d) detecting a signal indicative of said reaction between said analyte and said plurality of adaptors, thereby analyzing said analyte.

The planar array may comprise two or more types of analytes. The two or more types of analytes may be arranged randomly. The two or more types of analytes may be arranged in a regular pattern. The analyte may be a single cell analyte. The analyte may be a nucleic acid molecule. The analyte may be a protein molecule. The analyte may be a single cell. The analyte may be a particle. The analyte may be an organism. The analyte may be part of a colony. The analyte may be immobilized in an individually addressable location on the planar array.

The plurality of adaptors may comprise a plurality of probes. A given probe of the plurality of probes may be oligonucleotides 1 to 10 bases in length. A given probe may be a dibase probe. A given probe may be 10 to 20 bases in length. The plurality of probes may be labeled.

The substrate may comprise a linker that is coupled to the analyte. The linker may comprise a carbohydrate molecule. The linker may comprise an affinity binding protein. The linker may be hydrophilic. The linker may be hydrophobic. The linker may be electrostatic. The linker may be labeled. The linker may be integral to the substrate. The linker may be an independent layer on the substrate.

The method may further comprise, prior to (a), directing the analyte across the substrate comprising the linker. The analytic may be coupled to a bead, which bead is immobilized to the planar array. The planar array may be in fluid communication with at least one sample inlet and at least one sample outlet. The solution may be directed to the planar array using one or more dispensing nozzles. The one or more nozzles may be directed at or in proximity of the center of the substrate.

The method may further comprise recycling a subset of the solution that has contacted the substrate. The recycling may comprise collecting, filtering, and reusing the subset of the solution. The filtering may be molecular filtering.

The planar array may comprise a plurality of individually addressable locations. The planar array may be textured. The planar array may be a patterned array.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal.

The method may further comprise, prior to (b), subjecting the substrate to rotation with respect to the axis. The method may further comprise terminating rotation of the substrate prior to detecting the signal in (d). The signal may be detected in (d) while the substrate is rotating.

The signal may be generated by binding of a label to the analyte. The label may be bound to a molecule, particle, cell, or organism. The label may be bound to the molecule, particle, cell, or organism prior to (a). The label may be bound to the molecule, particle, cell, or organism subsequent to (a). The signal may be generated by formation of a detectable product by a chemical reaction. The reaction may comprise an enzymatic reaction. The signal may be generated by formation of a detectable product by physical association. The signal may be generated by formation of a detectable product by proximity association. The proximity association may comprise Förster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. The reaction may comprise a hybridization reaction or ligation reaction. The reaction may comprise a hybridization reaction and a ligation reaction.

The plurality of adaptors may comprise a plurality of carbohydrate molecules. The plurality of adaptors may comprise a plurality of lipid molecules. The plurality of adaptors may comprise a plurality of affinity binding proteins. The plurality of adaptors may comprise a plurality of aptamers. The plurality of adaptors may comprise a plurality of antibodies. The plurality of adaptors may be hydrophilic. The plurality of adaptors may be hydrophobic. The plurality of adaptors may be electrostatic. The plurality of adaptors may be labeled. The plurality of adaptors may comprise a plurality of oligonucleotide molecules. The plurality of adaptors may comprise a random sequence. The plurality of adaptors may comprise a targeted sequence. The plurality of adaptors may comprise a repeating sequence. The repeating sequence may be a homopolymer sequence.

The method may further comprise repeating (b)-(d) one or more times. Different solutions may be directed to the planar array during rotation of the substrate for consecutive cycles.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
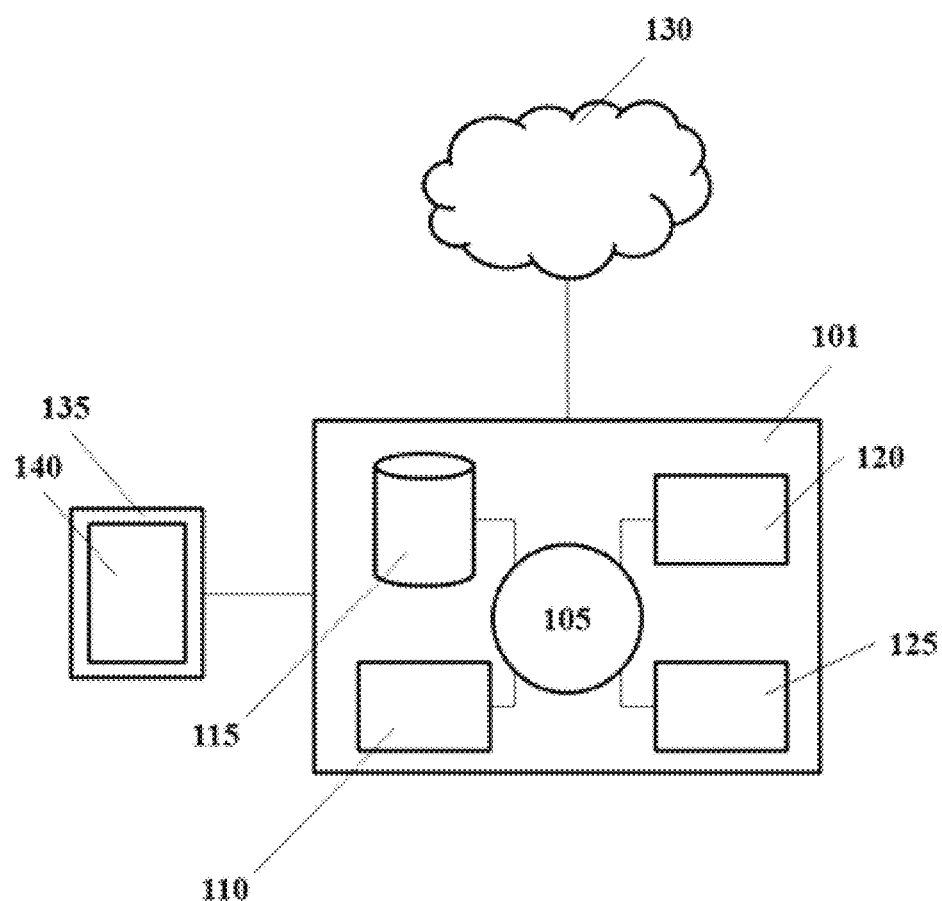
FIG. 1 shows a computer control system that is programmed or otherwise configured to implement methods provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "processing an analyte," as used herein, generally refers to one or more stages of interaction with one more sample substances. Processing an analyte may comprise conducting a chemical reaction, biochemical reaction, enzymatic reaction, hybridization reaction, polymerization reaction, physical reaction, any other reaction, or a combination thereof with, in the presence of, or on, the analyte. Processing an analyte may comprise physical and/or chemical manipulation of the analyte. For example, processing an analyte may comprise detection of a chemical change or physical change, addition of or subtraction of material, atoms, or molecules, molecular confirmation, detection of the presence of a fluorescent label, detection of a Forster resonance energy transfer (FRET) interaction, or inference of absence of fluorescence. The term "analyte" may refer to molecules, cells, biological particles, or organisms. In some instances, a molecule may be a nucleic acid molecule, antibody, antigen, peptide, protein, or other biological molecule obtained from or derived from a biological sample. An analyte may originate from, and/or be derived from, a biological sample, such as from a cell or organism. An analyte may be synthetic.

The term "sequencing," as used herein, generally refers to a process for generating or identifying a sequence of a biological molecule, such as a nucleic molecule. Such sequence may be a nucleic acid sequence, which may include a sequence of nucleic acid bases. Sequencing may be single molecule sequencing or sequencing by synthesis, for example. Sequencing may be performed using template nucleic acid molecules immobilized on a support, such as a flow cell or one or more beads.

The term "biological sample," as used herein, generally refers to any sample from a subject or specimen. The biological sample can be a fluid or tissue from the subject or specimen. The fluid can be blood (e.g., whole blood), saliva, urine, or sweat. The tissue can be from an organ (e.g., liver, lung, or thyroid), or a mass of cellular material, such as, for example, a tumor. The biological sample can be a feces sample, collection of cells (e.g., cheek swab), or hair sample. The biological sample can be a cell-free or cellular sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell free DNA or cell free RNA. The nucleic acid molecules may be derived from a variety of sources including human, mammal, non-human mammal, ape, monkey, chimpanzee, reptilian, amphibian, avian, or plant sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

The term "subject," as used herein, generally refers to an individual from whom a biological sample is obtained. The subject may be a mammal or non-mammal. The subject may be an animal, such as a monkey, dog, cat, bird, or rodent. The subject may be a human. The subject may be a patient. The subject may be displaying a symptom of a disease. The subject may be asymptomatic. The subject may be undergoing treatment. The subject may not be undergoing treatment. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The terms "nucleic acid," "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or deoxyribonucleic acids (DNA) or ribonucleotides or ribonucleic acids (RNA), or analogs thereof. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, and isolated RNA of any sequence. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 20 kb, 30 kb, 40 kb, 50 kb, 100 kb, 200 kb, 300 kb, 400 kb, 500 kb, 1 megabase (Mb), or more. A nucleic acid molecule (e.g., polynucleotide) can comprise a sequence of four natural nucleotide bases: adenine (A); cytosine (C); guanine (G); and thymine (T) (uracil (U) for thymine (T) when the polynucleotide is RNA). A nucleic acid molecule may include one or more nonstandard nucleotide(s), nucleotide analog(s) and/or modified nucleotide(s).

Nonstandard nucleotides, nucleotide analogs, and/or modified analogs may include, but are not limited to, diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyl adenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

The term "nucleotide," as used herein, generally refers to any nucleotide or nucleotide analog. The nucleotide may be naturally occurring or non-naturally occurring. The nucleotide analog may be a modified, synthesized or engineered nucleotide. The nucleotide analog may not be naturally occurring or may include a non-canonical base. The naturally occurring nucleotide may include a canonical base. The nucleotide analog may include a modified polyphosphate chain (e.g., triphosphate coupled to a fluorophore). The nucleotide analog may comprise a label. The nucleotide analog may be terminated (e.g., reversibly terminated). The nucleotide analog may comprise an alternative base.

The terms "amplifying," "amplification," and "nucleic acid amplification" are used interchangeably and generally refer to generating one or more copies of a nucleic acid or a template. For example, "amplification" of DNA generally refers to generating one or more copies of a DNA molecule. Moreover, amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, recombinase polymerase reaction (RPA), and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C.C. PNAS, 1989, 86, 4076-4080 and U.S. Pat. Nos. 5,409,811 and 5,674,716, each of which is herein incorporated by reference in its entirety.

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference).

The term "detector," as used herein, generally refers to a device that is capable of detecting a signal, including a signal indicative of the presence or absence of one or more incorporated nucleotides or fluorescent labels. The detector may detect multiple signals. The signal or multiple signals may be detected in real-time during, substantially during a biological reaction, such as a sequencing reaction (e.g., sequencing during a primer extension reaction), or subsequent to a biological reaction. In some cases, a detector can include optical and/or electronic components that can detect signals. The term "detector" may be used in detection methods. Non-limiting examples of detection methods include optical detection, spectroscopic detection, electrostatic detection, electrochemical detection, acoustic detection, magnetic detection, and the like. Optical detection methods include, but are not limited to, light absorption, ultraviolet-visible (UV-vis) light absorption, infrared light absorption, light scattering, Rayleigh scattering, Raman scattering, surface-enhanced Raman scattering, Mie scattering, fluorescence, luminescence, and phosphorescence. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "continuous area scanning," as used herein, generally refers to area scanning in rings, spirals, or arcs on a rotating substrate using an optical imaging system and a detector. Continuous area scanning may scan a substrate or array along a nonlinear path. Alternatively or in addition, continuous area scanning may scan a substrate or array along a linear or substantially linear path. The detector may be a continuous area scanning detector. The scanning direction may be substantially θ in an (R, θ) coordinate system in which the object rotation motion is in a θ direction. Across any field of view on the object (substrate) imaged by a scanning system, the apparent velocity may vary with the radial position (R) of the field point on the object as $$R\frac{d\theta}{dt}.$$

Continuous area scanning detectors may scan at the same rate for all image positions and therefore may not be able to operate at the correct scan rate for all imaged points in a curved (or arcuate or non-linear) scan. Therefore the scan may be corrupted by velocity blur for imaged field points moving at a velocity different than the scan velocity. Continuous rotational area scanning may comprise an optical detection system or method that makes algorithmic, optical, and/or electronic corrections to substantially compensate for this tangential velocity blur, thereby reducing this scanning aberration. For example, the compensation is accomplished algorithmically by using an image processing algorithm that deconvolves differential velocity blur at various image positions corresponding to different radii on the rotating substrate to compensate for differential velocity blur.

In another example, the compensation is accomplished by using an anamorphic magnification gradient. This may serve to magnify the substrate in one axis (anamorphic magnification) by different amounts at two or more substrate positions transverse to the scan direction. The anamorphic magnification gradient may modify the imaged velocities of the two or more positions to be substantially equal thereby compensating for tangential velocity differences of the two positions on the substrate. This compensation may be adjustable to account for different velocity gradients across the field of view at different radii on the substrate.

The imaging field of view may be segmented into two or more regions, each of which can be electronically controlled to scan at a different rate. These rates may be adjusted to the mean projected object velocity within each region. The regions may be optically defined using one or more beam splitters or one or more mirrors. The two or more regions may be directed to two or more detectors. The regions may be defined as segments of a single detector.

The term "continuous area scanning detector," as used herein, generally refers to an imaging array sensor capable of continuous integration over a scanning area wherein the scanning is electronically synchronized to the image of an object in relative motion. A continuous area scanning detector may comprise a time delay and integration (TDI) charge coupled device (CCD), Hybrid TDI, or complementary metal oxide semiconductor (CMOS) pseudo TDI.

The term "open substrate", as used herein, generally refers to a substantially planar substrate in which a single active surface is physically accessible at any point from a direction normal to the substrate. Substantially planar may refer to planarity at a micrometer level or nanometer level. Alternatively, substantially planar may refer to planarity at less than a nanometer level or greater than a micrometer level (e.g., millimeter level).

The term "anamorphic magnification", as used herein, generally refers to differential magnification between two axes of an image. An anamorphic magnification gradient may comprise differential anamorphic magnification in a first axis across a displacement in the second axis. The magnification in the second axis may be unity or any other value that is substantially constant over the field.

The term "field of view", as used herein, generally refers to the area on the sample or substrate that is optically mapped to the active area of the detector.

Processing an Analyte Using a Rotating Array

Prior microfluidic systems have utilized substrates containing numerous long, narrow channels. The typical flow cell geometry for such substrates introduces a need to compromise between two competing requirements: 1) minimizing volume to minimize reagent usage; and 2) maximizing effective hydraulic diameter to minimize flow time. This trade-off may be especially important for washing operations, which may require large wash volumes and thus long amounts of time to complete. The tradeoff is illustrated by the Poiseuille equation that dictates flow in the laminar regime and is thus inherent to microfluidic systems that utilize such flow cell geometries. Such flow cell geometries may also be susceptible to contamination. Because such flow cell geometries allow for a finite, limited number of channels in the microfluidic systems, such finite number of channels may be shared between a plurality of different mixtures comprising different analytes, reagents, agents, and/or buffers. Contents of fluids flowing through the same channels may be contaminated.

Described herein are devices, systems, and methods for processing analytes using open substrates or flow cell geometries that can address at least the abovementioned problems. The devices, systems and methods may be used to facilitate any application or process involving a reaction or interaction between an analyte and a fluid (e.g., a fluid comprising reagents, agents, buffers, other analytes, etc.). Such reaction or interaction may be chemical (e.g., polymerase reaction) or physical (e.g., displacement). The systems and methods described herein may benefit from higher efficiency, such as from faster reagent delivery and lower volumes of reagents required per surface area. The systems and methods described herein may avoid contamination problems common to microfluidic channel flow cells that are fed from multiport valves which can be a source of carryover from one reagent to the next. The devices, systems, and methods may benefit from shorter completion time, use of fewer resources (e.g., various reagents), and/or reduced system costs. The open substrates or flow cell geometries may be used to process any analyte, such as but not limited to, nucleic acid molecules, protein molecules, antibodies, antigens, cells, and/or organisms, as described herein. The open substrates or flow cell geometries may be used for any application or process, such as, but not limited to, sequencing by synthesis, sequencing by ligation, amplification, proteomics, single cell processing, barcoding, and sample preparation, as described herein.

The systems and methods may utilize a substrate comprising an array (such as a planar array) of individually addressable locations. Each location, or a subset of such locations, may have immobilized thereto an analyte (e.g., a nucleic acid molecule, a protein molecule, a carbohydrate molecule, etc.). For example, an analyte may be immobilized to an individually addressable location via a support, such as a bead. A plurality of analytes immobilized to the substrate may be copies of a template analyte. For example, the plurality of analytes may have sequence homology. In other instances, the plurality of analytes immobilized to the substrate may be different. The plurality of analytes may be of the same type of analyte (e.g., a nucleic acid molecule) or may be a combination of different types of analytes (e.g., nucleic acid molecules, protein molecules, etc.). The substrate may be rotatable about an axis. The analytes may be immobilized to the substrate during rotation. Reagents (e.g., nucleotides, antibodies, washing reagents, enzymes, etc.) may be dispensed onto the substrate prior to or during rotation (for instance, spun at a high rotational velocity) of the substrate to coat the array with the reagents and allow the analytes to interact with the reagents. For example, when the analytes are nucleic acid molecules and when the reagents comprise nucleotides, the nucleic acid molecules may incorporate or otherwise react with (e.g., transiently bind) one or more nucleotides. In another example, when the analytes are protein molecules and when the reagents comprise antibodies, the protein molecules may bind to or otherwise react with one or more antibodies. In another example, when the reagents comprise washing reagents, the substrate (and/or analytes on the substrate) may be washed of any unreacted (and/or unbound) reagents, agents, buffers, and/or other particles.

High speed coating across the substrate may be achieved via tangential inertia directing unconstrained spinning reagents in a partially radial direction (that is, away from the axis of rotation) during rotation, a phenomenon commonly referred to as centrifugal force. High speed rotation may involve a rotational speed of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, at least 10,000 rpm, or greater. This mode of directing reagents across a substrate may be herein referred to as centrifugal or inertial pumping. One or more signals (such as optical signals) may be detected from a detection area on the substrate prior to, during, or subsequent to, the dispensing of reagents to generate an output. For example, the output may be an intermediate or final result obtained from processing of the analyte. Signals may be detected in multiple instances. The dispensing, rotating, and/or detecting operations, in any order (independently or simultaneously), may be repeated any number of times to process an analyte. In some instances, the substrate may be washed (e.g., via dispensing washing reagents) between consecutive dispensing of the reagents.

Provided herein is a method for processing a biological analyte, comprising providing a substrate comprising an array having immobilized thereto the biological analyte, wherein the substrate is rotatable with respect to a central axis. In some instances, the array can be a planar array. In some instances, the array can be an array of wells. In some instances, the substrate can be textured and/or patterned. The method can comprise directing a solution across the substrate and bringing the solution in contact with the biological analyte during rotation of the substrate. The solution may be directed in a radial direction (e.g., outwards) with respect to the substrate to coat the substrate and contact the biological analytes immobilized to the array. In some instances, the solution may comprise a plurality of probes. In some instances, the solution may be a washing solution. The method can comprise subjecting the biological analyte to conditions sufficient to conduct a reaction between at least one probe of the plurality of probes and the biological analyte. The reaction may generate one or more signals from the at least one probe coupled to the biological analyte. The method can comprise detecting one or more signals, thereby analyzing the biological analyte.

The substrate may be a solid substrate. The substrate may entirely or partially comprise one or more of glass, silicon, a metal such as aluminum, copper, titanium, chromium, or steel, a ceramic such as titanium oxide or silicon nitride, plastic such as polyethylene (PE), low-density polyethylene (LDPE), high-density polyethylene (HDPE), polypropylene (PP), polystyrene (PS), high impact polystyrene (HIPS), polyvinyl chloride (PVC), polyvinylidene chloride (PVDC), acrylonitrile butadiene styrene (ABS), polyacetylene, polyamides, polycarbonates, polyesters, polyurethanes, polyepoxide, polymethyl methacrylate (PMMA), polytetrafluoroethylene (PTFE), phenol formaldehyde (PF), melamine formaldehyde (MF), urea-formaldehyde (UF), polyetheretherketone (PEEK), polyetherimide (PEI), polyimides, polylactic acid (PLA), furans, silicones, polysulfones, any mixture of any of the preceding materials, or any other appropriate material. The substrate may be entirely or partially coated with one or more layers of a metal such as aluminum, copper, silver, or gold, an oxide such as a silicon oxide ($Si_xO_y$, where x, y may take on any possible values), a photoresist such as SU8, a surface coating such as an aminosilane or hydrogel, polyacrylic acid, polyacrylamide dextran, polyethylene glycol (PEG), or any combination of any of the preceding materials, or any other appropriate coating. The one or more layers may have a thickness of at least 1 nanometer (nm), at least 2 nm, at least 5 nm, at least 10 nm, at least 20 nm, at least 50 nm, at least 100 nm, at least 200 nm, at least 500 nm, at least 1 micrometer (μm), at least 2 μm, at least 5 μm, at least 10 μm, at least 20 μm, at least 50 μm, at least 100 μm, at least 200 μm, at least 500 μm, or at least 1 millimeter (mm). The one or more layers may have a thickness that is within a range defined by any two of the preceding values.

The substrate may have the general form of a cylinder, a cylindrical shell or disk, a rectangular prism, or any other geometric form. The substrate may have a thickness (e.g., a minimum dimension) of at least 100 μm, at least 200 μm, at least 500 μm, at least 1 mm, at least 2 mm, at least 5 mm, or at least 10 mm. The substrate may have a thickness that is within a range defined by any two of the preceding values. The substrate may have a first lateral dimension (such as a width for a substrate having the general form of a rectangular prism or a radius for a substrate having the general form of a cylinder) of at least 1 mm, at least 2 mm, at least 5 mm, at least 10 mm, at least 20 mm, at least 50 mm, at least 100 mm, at least 200 mm, at least 500 mm, or at least 1,000 mm. The substrate may have a first lateral dimension that is within a range defined by any two of the preceding values. The substrate may have a second lateral dimension (such as a length for a substrate having the general form of a rectangular prism) or at least 1 mm, at least 2 mm, at least 5 mm, at least 10 mm, at least 20 mm, at least 50 mm, at least 100 mm, at least 200 mm, at least 500 mm, or at least 1,000 mm. The substrate may have a second lateral dimension that is within a range defined by any two of the preceding values. A surface of the substrate may be planar. Alternatively or in addition to, a surface of the substrate may be textured or patterned. For example, the substrate may comprise grooves, troughs, hills, and/or pillars. The substrate may define one or more cavities (e.g., micro-scale cavities or nano-scale cavities). The substrate may have a regular textures and/or patterns across the surface of the substrate. For example, the substrate may have regular geometric structures (e.g., wedges, cuboids, cylinders, spheroids, hemispheres, etc.) above or below a reference level of the surface. Alternatively, the substrate may have irregular textures and/or patterns across the surface of the substrate. For example, the substrate may have any arbitrary structure above or below a reference level of the substrate. In some instances, a texture of the substrate may comprise structures having a maximum dimension of at most about 100%, 90%, 80%, 70%, 60%, 50%, 40%, 30%, 20%, 10%, 9%, 8%, 7%, 6%, 5%, 4%, 3%, 2%, 1%, 0.1%, 0.01%, 0.001%, 0.0001%, 0.00001% of the total thickness of the substrate or a layer of the substrate. In some instances, the textures and/or patterns of the substrate may define at least part of an individually addressable location on the substrate. A textured and/or patterned substrate may be substantially planar.

The substrate may comprise an array. For instance, the array may be located on a lateral surface of the substrate. The array may be a planar array. The array may have the general shape of a circle, annulus, rectangle, or any other shape. The array may comprise linear and/or non-linear rows. The array may be evenly spaced or distributed. The array may be arbitrarily spaced or distributed. The array may have regular spacing. The array may have irregular spacing. The array may be a textured array. The array may be a patterned array. The array may comprise a plurality of individually addressable locations. The analyte to be processed may be immobilized to the array. The array may comprise one or more binders described herein, such as one or more physical or chemical linkers or adaptors, that are coupled to a biological analyte. For instance, the array may comprise a linker or adaptor that is coupled to a nucleic acid molecule. Alternatively or in addition to, the biological analyte may be coupled to a bead; the bead may be immobilized to the array.

The individually addressable locations may comprise locations of analytes or groups of analytes that are accessible for manipulation. The manipulation may comprise placement, extraction, reagent dispensing, seeding, heating, cooling, or agitation. The extraction may comprise extracting individual analytes or groups of analytes. For instance, the extraction may comprise extracting at least 2, at least 5, at least 10, at least 20, at least 50, at least 100, at least 200, at least 500, or at least 1,000 analytes or groups of analytes. Alternatively or in addition to, the extraction may comprise extracting at most 1,000, at most 500, at most 200, at most 100, at most 50, at most 20, at most 10, at most 5, or at most 2 analytes or groups of analytes. The manipulation may be accomplished through, for example, localized microfluidic, pipet, optical, laser, acoustic, magnetic, and/or electromagnetic interactions with the analyte or its surroundings.

The array may be coated with binders. For instance, the array may be randomly coated with binders. Alternatively, the array may be coated with binders arranged in a regular pattern (e.g., in linear arrays, radial arrays, hexagonal arrays etc.). The array may be coated with binders on at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% of the number of individually addressable locations, or of the surface area of the substrate. The array may be coated with binders on a fraction of individually addressable locations, or of the surface areas of the substrate, that is within a range defined by any two of the preceding values. The binders may be integral to the array. The binders may be added to the array. For instance, the binders may be added to the array as one or more coating layers on the array.

The binders may immobilize biological analytes through non-specific interactions, such as one or more of hydrophilic interactions, hydrophobic interactions, electrostatic interactions, physical interactions (for instance, adhesion to pillars or settling within wells), and the like. The binders may immobilize biological analytes through specific interactions. For instance, where the biological analyte is a nucleic acid molecule, the binders may comprise oligonucleotide adaptors configured to bind to the nucleic acid molecule. Alternatively or in addition, such as to bind other types of analytes, the binders may comprise one or more of antibodies, oligonucleotides, aptamers, affinity binding proteins, lipids, carbohydrates, and the like. The binders may immobilize biological analytes through any possible combination of interactions. For instance, the binders may immobilize nucleic acid molecules through a combination of physical and chemical interactions, through a combination of protein and nucleic acid interactions, etc. The array may comprise at least about 10, 100, 1000, 10,000, 100,000, 1,000,000, 10,000,000, 100,000,000 or more binders. Alternatively or in addition, the array may comprise at most about 100,000,000, 10,000,000, 1,000,000, 100,000, 10,000, 1000, 100, 10 or fewer binders. The array may have a number of binders that is within a range defined by any two of the preceding values. In some instances, a single binder may bind a single biological analyte (e.g., nucleic acid molecule). In some instances, a single binder may bind a plurality of biological analytes (e.g., plurality of nucleic acid molecules). In some instances, a plurality of binders may bind a single biological analyte. Though examples herein describe interactions of binders with nucleic acid molecules, the binders may immobilize other molecules (such as proteins), other particles, cells, viruses, other organisms, or the like.

In some instances, each location, or a subset of such locations, may have immobilized thereto an analyte (e.g., a nucleic acid molecule, a protein molecule, a carbohydrate molecule, etc.). In other instances, a fraction of the plurality of individually addressable location may have immobilized thereto an analyte. A plurality of analytes immobilized to the substrate may be copies of a template analyte. For example, the plurality of analytes (e.g., nucleic acid molecules) may have sequence homology. In other instances, the plurality of analytes immobilized to the substrate may not be copies. The plurality of analytes may be of the same type of analyte (e.g., a nucleic acid molecule) or may be a combination of different types of analytes (e.g., nucleic acid molecules, protein molecules, etc.).

In some instances, the array may comprise a plurality of types of binders, such as to bind different types of analytes. For example, the array may comprise a first type of binders (e.g., oligonucleotides) configured to bind a first type of analyte (e.g., nucleic acid molecules), and a second type of binders (e.g., antibodies) configured to bind a second type of analyte (e.g., proteins), and the like. In another example, the array may comprise a first type of binders (e.g., first type of oligonucleotide molecules) to bind a first type of nucleic acid molecules and a second type of binders (e.g., second type of oligonucleotide molecules) to bind a second type of nucleic acid molecules, and the like. For example, the substrate may be configured to bind different types of analytes in certain fractions or specific locations on the substrate by having the different types of binders in the certain fractions or specific locations on the substrate.

A biological analyte may be immobilized to the array at a given individually addressable location of the plurality of individually addressable locations. An array may have any number of individually addressable locations. For instance, the array may have at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000, at least 2,000,000,000, at least 5,000,000,000, at least 10,000,000,000, at least 20,000,000,000, at least 50,000,000,000, or at least 100,000,000,000 individually addressable locations. The array may have a number of individually addressable locations that is within a range defined by any two of the preceding values. Each individually addressable location may be digitally and/or physically accessible individually (from the plurality of individually addressable locations). For example, each individually addressable location may be located, identified, and/or accessed electronically or digitally for mapping, sensing, associating with a device (e.g., detector, processor, dispenser, etc.), or otherwise processing. Alternatively or in addition to, each individually addressable location may be located, identified, and/or accessed physically, such as for physical manipulation or extraction of an analyte, reagent, particle, or other component located at an individually addressable location.

Each individually addressable location may have the general shape or form of a circle, pit, bump, rectangle, or any other shape or form. Each individually addressable location may have a first lateral dimension (such as a radius for individually addressable locations having the general shape of a circle or a width for individually addressable locations having the general shape of a rectangle). The first lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The first lateral dimension may be within a range defined by any two of the preceding values. Each individually addressable location may have a second lateral dimension (such as a length for individually addressable locations having the general shape of a rectangle). The second lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The second lateral dimension may be within a range defined by any two of the preceding values. In some instances, each individually addressable locations may have or be coupled to a binder, as described herein, to immobilize a analyte thereto. In some instances, only a fraction of the individually addressable locations may have or be coupled to a binder. In some instances, an individually addressable location may have or be coupled to a plurality of binders to immobilize an analyte thereto.

The analytes bound to the individually addressable locations may include, but are not limited to, molecules, cells, organisms, nucleic acid molecules, nucleic acid colonies, beads, clusters, polonies, or DNA nanoballs. The bound analytes may be immobilized to the array in a regular, patterned, periodic, random, or pseudo-random configuration, or any other spatial arrangement.

The substrate may be configured to rotate with respect to an axis. In some instances, the systems, devices, and apparatus described herein may further comprise a rotational unit configured to rotate the substrate. The rotational unit may comprise a motor and/or a rotor to rotate the substrate. Such motor and/or rotor may be mechanically connected to the substrate directly or indirectly via intermediary components (e.g., gears, stages, actuators, discs, pulleys, etc.). The rotational unit may be automated. Alternatively or in addition, the rotational unit may receive manual input. The axis of rotation may be an axis through the center of the substrate. The axis may be an off-center axis. For instance, the substrate may be affixed to a chuck (such as a vacuum chuck) of a spin coating apparatus. The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational velocities during different operations described herein. The substrate may be configured to rotate with a rotational velocity that varies according to a time-dependent function, such as a ramp, sinusoid, pulse, or other function or combination of functions. The time-varying function may be periodic or aperiodic.

A solution may be provided to the substrate prior to or during rotation of the substrate to centrifugally direct the solution across the array. In some instances, the solution may be provided to the planar array during rotation of the substrate in pulses, thereby creating an annular wave of the solution moving radially outward. The pulses may have periodic or non-periodic (e.g., arbitrary) intervals. A series of pulses may comprise a series of waves producing a surface-reagent exchange. The surface-reagent exchange may comprise washing in which each subsequent pulse comprises a reduced concentration of the surface reagent. The solution may have a temperature different than that of the substrate, thereby providing a source or sink of thermal energy to the substrate or to an analyte located on the substrate. The thermal energy may provide a temperature change to the substrate or to the analyte. The temperature change may be transient. The temperature change may enable, disable, enhance, or inhibit a chemical reaction, such as a chemical reaction to be carried out upon the analyte. For example, the chemical reaction may comprise denaturation, hybridization, or annealing of nucleic acid molecules. The chemical reaction may comprise a step in a polymerase chain reaction (PCR), bridge amplification, or other nucleic acid amplification reaction. The temperature change may modulate, increase, or decrease a signal detected from the analyte.

The array may be in fluid communication with at least one sample inlet (of a fluid channel). The array may be in fluid communication with the sample inlet via an air gap. In some cases, the array may additionally be in fluid communication with at least one sample outlet. The array may be in fluid communication with the sample outlet via an airgap. The sample inlet may be configured to direct a solution to the array. The sample outlet may be configured to receive a solution from the array. The solution may be directed to the array using one or more dispensing nozzles. For example, the solution may be directed to the array using at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 dispensing nozzles. The solution may be directed to the array using a number of nozzles that is within a range defined by any two of the preceding values. In some cases, different reagents (e.g., nucleotide solutions of different types, different probes, washing solutions, etc.) may be dispensed via different nozzles, such as to prevent contamination. Each nozzle may be connected to a dedicated fluidic line or fluidic valve, which may further prevent contamination. A type of reagent may be dispensed via one or more nozzles. The one or more nozzles may be directed at or in proximity to a center of the substrate. Alternatively, the one or more nozzles may be directed at or in proximity to a location on the substrate other than the center of the substrate. Alternatively or in combination, one or more nozzles may be directed closer to the center of the substrate than one or more of the other nozzles. For instance, one or more nozzles used for dispensing washing reagents may be directed closer to the center of the substrate than one or more nozzles used for dispensing active reagents. The one or more nozzles may be arranged at different radii from the center of the substrate. Two or more nozzles may be operated in combination to deliver fluids to the substrate more efficiently. One or more nozzles may be configured to deliver fluids to the substrate as a jet, spray (or other dispersed fluid), and/or droplets. One or more nozzles may be operated to nebulize fluids prior to delivery to the substrate.

The solution may be dispensed on the substrate while the substrate is stationary; the substrate may then be subjected to rotation following the dispensing of the solution. Alternatively, the substrate may be subjected to rotation prior to the dispensing of the solution; the solution may then be dispensed on the substrate while the substrate is rotating.

Rotation of the substrate may yield a centrifugal force (or inertial force directed away from the axis) on the solution, causing the solution to flow radially outward over the array. In this manner, rotation of the substrate may direct the solution across the array. Continued rotation of the substrate over a period of time may dispense a fluid film of a nearly constant thickness across the array. The rotational velocity of the substrate may be selected to attain a desired thickness of a film of the solution on the substrate. The film thickness may be related to the rotational velocity by equation (1):

$$h(t) = \frac{\sqrt{3\mu/2}}{\sqrt{2t\rho\omega^2 - 3\mu C}} \tag{1}$$

Here, h(t) is the thickness of the fluid film at time t, μ is the viscosity of the fluid, ω is the rotational velocity, and C is a constant.

Alternatively or in combination, the viscosity of the solution may be chosen to attain a desired thickness of a film of the solution on the substrate. For instance, the rotational velocity of the substrate or the viscosity of the solution may be chosen to attain a film thickness of at least 10 nanometers (nm), at least 20 nm, at least 50 nm, at least 100 nm, at least 200 nm, at least 500 nm, at least 1 micrometer (μm), at least 2 μm, at least 5 μm, at least 10 μm, at least 20 μm, at least 50 μm, at least 100 μm. at least 200 μm, at least 500 μm, or at least 1 mm. The rotational velocity of the substrate and/or the viscosity of the solution may be chosen to attain a film thickness that is within a range defined by any two of the preceding values. The viscosity of the solution may be controlled by controlling a temperature of the solution. The thickness of the film may be measured or monitored. Measurements or monitoring of the thickness of the film may be incorporated into a feedback system to better control the film thickness. The thickness of the film may be measured or monitored by a variety of techniques. For instances, the thickness of the film may be measured or monitored by thin film spectroscopy with a thin film spectrometer, such as a fiber spectrometer.

The solution may be a reaction mixture comprising a variety of components. For example, the solution may comprise a plurality of probes configured to interact with the analyte. For example, the probes may have binding specificity to the analyte. In another example, the probes may not have binding specificity to the analyte. A probe may be configured to permanently couple to the analyte. A probe may be configured to transiently couple to the analyte. For example, a nucleotide probe may be permanently incorporated into a growing strand hybridized to a nucleic acid molecule analyte. Alternatively, a nucleotide probe may transiently bind to the nucleic acid molecule analyte. Transiently coupled probes may be subsequently removed from the analyte. Subsequent removal of the transiently coupled probes from an analyte may or may not leave a residue (e.g., chemical residue) on the analyte. A type of probe in the solution may depend on the type of analyte. A probe may comprise a functional group or moiety configured to perform specific functions. For example, a probe may comprise a label (e.g., dye). A probe may be configured to generate a detectable signal (e.g., optical signal), such as via the label, upon coupling or otherwise interacting with the analyte. In some instances, a probe may be configured to generate a detectable signal upon activation (e.g., a stimuli). In another example, a nucleotide probe may comprise reversible terminators (e.g., blocking groups) configured to terminate polymerase reactions (until unblocked). The solution may comprise other components to aid, accelerate, or decelerate a reaction between the probe and the analyte (e.g., enzymes, catalysts, buffers, saline solutions, chelating agents, reducing agents, other agents, etc.). In some instances, the solution may be a washing solution. In some instances, a washing solution may be directed to the substrate to bring the washing solution in contact with the array after a reaction or interaction between reagents (e.g., a probe) in a reaction mixture solution with an analyte immobilized on the array. The washing solution may wash away any free reagents from the previous reaction mixture solution.

A detectable signal, such as an optical signal (e.g., fluorescent signal), may be generated upon reaction between a probe in the solution and the analyte. For example, the signal may originate from the probe and/or the analyte. The detectable signal may be indicative of a reaction or interaction between the probe and the analyte. The detectable signal may be a non-optical signal. For example, the detectable signal may be an electronic signal. The detectable signal may be detected by one or more sensors. For example, an optical signal may be detected via one or more optical detectors in an optical detection scheme described elsewhere herein. The signal may be detected during rotation of the substrate. The signal may be detected following termination of the rotation. The signal may be detected while the analyte is in fluid contact with the solution. The signal may be detected following washing of the solution. In some instances, after the detection, the signal may be muted, such as by cleaving a label from the probe and/or the analyte, and/or modifying the probe and/or the analyte. Such cleaving and/or modification may be effected by one or more stimuli, such as exposure to a chemical, an enzyme, light (e.g., ultraviolet light), or temperature change (e.g., heat). In some instances, the signal may otherwise become undetectable by deactivating or changing the mode (e.g., detection wavelength) of the one or more sensors, or terminating or reversing an excitation of the signal. In some instances, detection of a signal may comprise capturing an image or generating a digital output (e.g., between different images).

The operations of directing a solution to the substrate and detection of one or more signals indicative of a reaction between a probe in the solution and an analyte in the array may be repeated one or more times. Such operations may be repeated in an iterative manner. For example, the same analyte immobilized to a given location in the array may interact with multiple solutions in the multiple repetition cycles. For each iteration, the additional signals detected may provide incremental, or final, data about the analyte during the processing. For example, where the analyte is a nucleic acid molecule and the processing is sequencing, additional signals detected at each iteration may be indicative of a base in the nucleic acid sequence of the nucleic acid molecule. The operations may be repeated at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 cycles to process the analyte. In some instances, a different solution may be directed to the substrate for each cycle. For example, at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 solutions may be directed to the substrate.

In some instances, a washing solution may be directed to the substrate between each cycle (or at least once during each cycle). For instance, a washing solution may be directed to the substrate after each type of reaction mixture solution is directed to the substrate. The washing solutions may be distinct. The washing solutions may be identical. The washing solution may be dispensed in pulses during rotation, creating annular waves as described herein. For example, at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 washing solutions may be directed to the substrate.

In some instances, a subset or an entirety of the solution(s) may be recycled after the solution(s) have contacted the substrate. Recycling may comprise collecting, filtering, and reusing the subset or entirety of the solution. The filtering may be molecule filtering.

Nucleic Acid Sequencing Using a Rotating Array

In some instances, a method for sequencing may employ sequencing by synthesis schemes wherein a nucleic acid molecule is sequenced base-by-base with primer extension reactions. For example, a method for sequencing a nucleic acid molecule may comprise providing a substrate comprising an array having immobilized thereto the nucleic acid molecule. The array may be a planar array. The substrate may be configured to rotate with respect to an axis. The method may comprise directing a solution comprising a plurality of nucleotides across the array prior to or during rotation of the substrate. Rotation of the substrate may facilitate coating of the substrate surface with the solution. The nucleic acid molecule may be subjected to a primer extension reaction under conditions sufficient to incorporate or specifically bind at least one nucleotide from the plurality of nucleotides into a growing strand that is complementary to the nucleic acid molecule. A signal indicative of incorporation or binding of at least one nucleotide may be detected, thereby sequencing the nucleic acid molecule.

In some instances, the method may comprise, prior to providing the substrate having immobilized thereto the nucleic acid molecule, immobilizing the nucleic acid molecule to the substrate. For example, a solution comprising a plurality of nucleic acid molecules comprising the nucleic acid molecule may be directed to the substrate prior to, during, or subsequent to rotation of the substrate, and the substrate may be subject to conditions sufficient to immobilize at least a subset of the plurality of nucleic acid molecules as an array on the substrate.

Figure 2:
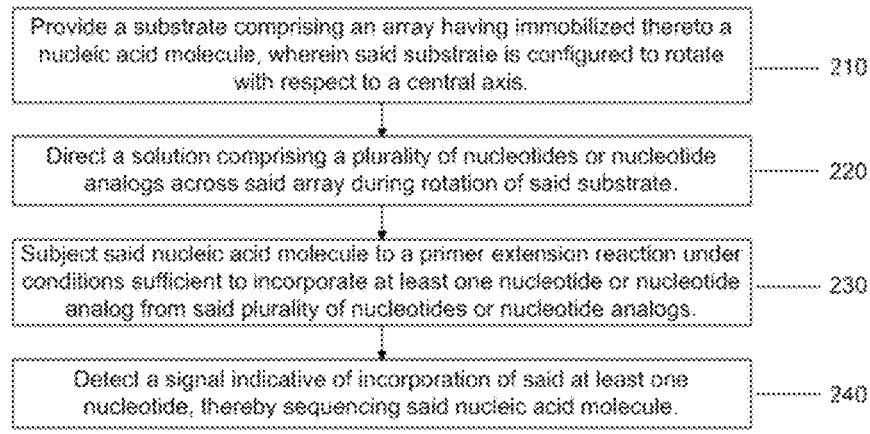
FIG. 2 shows a method for sequencing a nucleic acid molecule.

FIG. 2 shows a method 200 for sequencing a nucleic acid molecule. In a first operation 210, the method may comprise providing a substrate, as described elsewhere herein. The substrate may comprise an array of a plurality of individually addressable locations. The array may be a planar array. The array may be a textured array. The array may be a patterned array. For example, the array may define individually addressable locations with wells and/or pillars. A plurality of nucleic acid molecules, which may or may not be copies of the same nucleic acid molecule, may be immobilized to the array. Each nucleic acid molecule from the plurality of nucleic acid molecules may be immobilized to the array at a given individually addressable location of the plurality of individually addressable locations.

The substrate may be configured to rotate with respect to an axis. The axis may be an axis through the center or substantially center of the substrate. The axis may be an off-center axis. For instance, the substrate may be affixed to a chuck (such as a vacuum chuck) of a spin coating apparatus. The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational velocities during different operations described herein. The substrate may be configured to rotate with a rotational velocity that varies according to a time-dependent function, such as a ramp, sinusoid, pulse, or other function or combination of functions. The time-varying function may be periodic or aperiodic.

In a second operation 220, the method may comprise directing a solution across the array prior to or during rotation of the substrate. The solution may be centrifugally directed across the array. In some instances, the solution may be directed to the array during rotation of the substrate in pulses, thereby creating an annular wave of the solution moving radially outward. The solution may have a temperature different than that of the substrate, thereby providing a source or sink of thermal energy to the substrate or to a nucleic acid molecules located on the substrate. The thermal energy may provide a temperature change to the substrate or to the nucleic acid molecule. The temperature change may be transient. The temperature change may enable, disable, enhance, or inhibit a chemical reaction, such as a chemical reaction to be carried out upon the nucleic acid molecule. The chemical reaction may comprise denaturation, hybridization, or annealing of the plurality of nucleic acid molecules. The chemical reaction may comprise a step in a polymerase chain reaction (PCR), bridge amplification, or other nucleic acid amplification reaction. The temperature change may modulate, increase, or decrease a signal detected from the nucleic acid molecules (or from probes in the solution).

In some instances, the solution may comprise probes configured to interact with nucleic acid molecules. For example, in some instances, such as for performing sequencing by synthesis, the solution may comprise a plurality of nucleotides (in single bases). The plurality of nucleotides may include nucleotide analogs, naturally occurring nucleotides, and/or non-naturally occurring nucleotides, collectively referred to herein as "nucleotides." The plurality of nucleotides may or may not be bases of the same type (e.g., A, T, G, C, etc.). For example, the solution may or may not comprise bases of only one type. The solution may comprise at least 1 type of base or bases of at least 2, at least 3, at least 4, at least 5, at least 6, at least 7, at least 8, at least 9, or at least 10 types. For instance, the solution may comprise any possible mixture of A, T, C, and G. In some instances, the solution may comprise a plurality of natural nucleotides and non-natural nucleotides. The plurality of natural nucleotides and non-natural nucleotides may or may not be bases of the same type (e.g., A, T, G, C).

One or more nucleotides of the plurality of nucleotides may be terminated (e.g., reversibly terminated). For example, a nucleotide may comprise a reversible terminator, or a moiety that is capable of terminating primer extension reversibly. Nucleotides comprising reversible terminators may be accepted by polymerases and incorporated into growing nucleic acid sequences analogously to non-reversibly terminated nucleotides. Following incorporation of a nucleotide analog comprising a reversible terminator into a nucleic acid strand, the reversible terminator may be removed to permit further extension of the nucleic acid strand. A reversible terminator may comprise a blocking or capping group that is attached to the 3'-oxygen atom of a sugar moiety (e.g., a pentose) of a nucleotide or nucleotide analog. Such moieties are referred to as 3'-O-blocked reversible terminators. Examples of 3'-O-blocked reversible terminators include, for example, 3'-ONH$_2$ reversible terminators, 3'-O-allyl reversible terminators, and 3'-O-aziomethyl reversible terminators. Alternatively, a reversible terminator may comprise a blocking group in a linker (e.g., a cleavable linker) and/or dye moiety of a nucleotide analog. 3'-unblocked reversible terminators may be attached to both the base of the nucleotide analog as well as a fluorescing group (e.g., label, as described herein). Examples of 3'-unblocked reversible terminators include, for example, the "virtual terminator" developed by Helicos BioSciences Corp. and the "lightning terminator" developed by Michael L. Metzker et al. Cleavage of a reversible terminator may be achieved by, for example, irradiating a nucleic acid molecule including the reversible terminator.

One or more nucleotides of the plurality of nucleotides may be labeled with a dye, fluorophore, or quantum dot. For example, the solution may comprise labeled nucleotides. In another example, the solution may comprise unlabeled nucleotides. In another example, the solution may comprise a mixture of labeled and unlabeled nucleotides. Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino}fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, Atto 390, 425, 465, 488, 495, 532, 565, 594, 633, 647, 647N, 665, 680 and 700 dyes, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; CySQ and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be one with linkers. For instance, a label may have a disulfide linker attached to the label. Non-limiting examples of such labels include Cy5-azide, Cy-2-azide, Cy-3-azide, Cy-3.5-azide, Cy5.5-azide and Cy-7-azide. In some cases, a linker may be a cleavable linker. In some cases, the label may be a type that does not self-quench or exhibit proximity quenching. Non-limiting examples of a label type that does not self-quench or exhibit proximity quenching include Bimane derivatives such as Monobromobimane. Alternatively, the label may be a type that self-quenches or exhibits proximity quenching. Non-limiting examples of such labels include Cy5-azide, Cy-2-azide, Cy-3-azide, Cy-3.5-azide, Cy5.5-azide and Cy-7-azide. In some instances, a blocking group of a reversible terminator may comprise the dye.

The solution may be directed to the array using one or more nozzles. In some cases, different reagents (e.g., nucleotide solutions of different types, washing solutions, etc.) may be dispensed via different nozzles, such as to prevent contamination. Each nozzle may be connected to a dedicated fluidic line or fluidic valve, which may further prevent contamination. A type of reagent may be dispensed via one or more nozzles. The one or more nozzles may be directed at or in proximity to a center of the substrate. Alternatively, the one or more nozzles may be directed at or in proximity to a location on the substrate other than the center of the substrate. Two or more nozzles may be operated in combination to deliver fluids to the substrate more efficiently.

The solution may be dispensed on the substrate while the substrate is stationary; the substrate may then be subjected to rotation following the dispensing of the solution. Alternatively, the substrate may be subjected to rotation prior to the dispensing of the solution; the solution may then be dispensed on the substrate while the substrate is rotating. Rotation of the substrate may yield a centrifugal force (or inertial force directed away from the axis) on the solution, causing the solution to flow radially outward over the array.

In a third operation 230, the method may comprise subjecting the nucleic acid molecule to a primer extension reaction. The primer extension reaction may be conducted under conditions sufficient to incorporate at least one nucleotide from the plurality of nucleotides into a growing strand that is complementary to the nucleic acid molecule. The nucleotide incorporated may or may not be labeled.

In some cases, the operation 230 may further comprise modifying at least one nucleotide. Modifying the nucleotide may comprise labeling the nucleotide. For instance, the nucleotide may be labeled, such as with a dye, fluorophore, or quantum dot. The nucleotide may be cleavably labeled. In some instances, modifying the nucleotide may comprise activating (e.g., stimulating) a label of the nucleotide.

In a fourth operation 240, the method may comprise detecting a signal indicative of incorporation of the at least one nucleotide. The signal may be an optical signal. The signal may be a fluorescence signal. The signal may be detected during rotation of the substrate. The signal may be detected following termination of the rotation. The signal may be detected while the nucleic acid molecule to be sequenced is in fluid contact with the solution. The signal may be detected following fluid contact of the nucleic acid molecule with the solution. The operation 240 may further comprise modifying a label of the at least one nucleotide. For instance, the operation 240 may further comprise cleaving the label of the nucleotide (e.g., after detection). The nucleotide may be cleaved by one or more stimuli, such as exposure to a chemical, an enzyme, light (e.g., ultraviolet light), or heat. Once the label is cleaved, a signal indicative of the incorporated nucleotide may not be detectable with one or more detectors.

The method 200 may further comprise repeating operations 220, 230, and/or 240 one or more times to identify one or more additional signals indicative of incorporation of one or more additional nucleotides, thereby sequencing the nucleic acid molecule. The method 200 may comprise repeating operations 220, 230, and/or 240 in an iterative manner. For each iteration, an additional signal may indicate incorporation of an additional nucleotide. The additional nucleotide may be the same nucleotide as detected in the previous iteration. The additional nucleotide may be a different nucleotide from the nucleotide detected in the previous iteration. In some instances, at least one nucleotide may be modified (e.g., labeled and/or cleaved) between each iteration of the operations 220, 230, or 240. For instance, the method may comprise repeating the operations 220, 230, and/or 240 at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 times. The method may comprise repeating the operations 220, 230, and/or 240 a number of times that is within a range defined by any two of the preceding values. The method 200 may thus result in the sequencing of a nucleic acid molecule of any size.

The method may comprise directing different solutions to the array during rotation of the substrate in a cyclical manner. For instance, the method may comprise directing a first solution containing a first type of nucleotide (e.g., in a plurality of nucleotides of the first type) to the array, followed by a second solution containing a second type of nucleotide, followed by a third type of nucleotide, followed by a fourth type of nucleotide, etc. In another example, different solutions may comprise different combinations of types of nucleotides. For example, a first solution may comprise a first canonical type of nucleotide (e.g., A) and a second canonical type of nucleotide (e.g., C), and a second solution may comprise the first canonical type of nucleotide (e.g., A) and a third canonical type of nucleotide (e.g., T), and a third solution may comprise the first canonical type, second canonical type, third canonical type, and a fourth canonical type (e.g., G) of nucleotide. In another example, a first solution may comprise labeled nucleotides, and a second solution may comprise unlabeled nucleotides, and a third solution may comprise a mixture of labeled and unlabeled nucleotides. The method may comprise directing at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 solutions to the array. The method may comprise directing a number of solutions that is within a range defined by any two of the preceding values to the array. The solutions may be distinct. The solutions may be identical.

The method may comprise directing at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000, 000, at least 2,000,000, at least 5,000,000, at least 10,000, 000, at least 20,000,000, at least 50,000,000, at least 100, 000,000, at least 200,000,000, at least 500,000,000, or at least 1,000,000,000 washing solutions to the substrate. For instance, a washing solution may be directed to the substrate after each type of nucleotide is directed to the substrate. The washing solutions may be distinct. The washing solutions may be identical. The washing solution may be dispensed in pulses during rotation, creating annular waves as described herein.

The method may further comprise recycling a subset or an entirety of the solution(s) after the solution(s) have contacted the substrate. Recycling may comprise collecting, filtering, and reusing the subset or entirety of the solution. The filtering may be molecule filtering.

The operations 220 and 230 may occur at a first location and the operation 240 may occur at a second location. The first and second locations may comprise first and second processing bays, respectively, as described herein (for instance, with respect to FIG. 12G). The first and second locations may comprise first and second rotating spindles, respectively, as described herein (for instance, with respect to FIG. 13). The first rotating spindle may be exterior or interior to the second rotating spindle. The first and second rotating spindles may be configured to rotate with different angular velocities. Alternatively, the operation 220 may occur at a first location and the operations 230 and 240 may occur at the second location.

The method may further comprise transferring the substrate between the first and second locations. Operations 220 and 230 may occur while the substrate is rotated at a first angular velocity and operation 240 may occur while the substrate is rotated at a second angular velocity. The first angular velocity may be less than the second angular velocity. The first angular velocity may be between about 0 rpm and about 100 rpm. The second angular velocity may be between about 100 rpm and about 1,000 rpm. Alternatively, the operation 220 may occur while the substrate is rotated at the first angular velocity and the operations 230 and 240 may occur while the substrate is rotated at the second angular velocity.

Many variations, alterations, and adaptations based on the method 200 provided herein are possible. For example, the order of the operations of the method 200 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated. Some of the operations may be manual.

For example, in some cases, in the third operation 230, instead of facilitating a primer extension reaction, the nucleic acid molecule may be subject to conditions to allow transient binding of a nucleotide from the plurality of nucleotides to the nucleic acid molecule. The transiently bound nucleotide may be labeled. The transiently bound nucleotide may be removed, such as after detection (e.g., see operation 240). Then, a second solution may be directed to the substrate, this time under conditions to facilitate the primer extension reaction, such that a nucleotide of the second solution is incorporated (e.g., into a growing strand hybridized to the nucleic acid molecule). The incorporated nucleotide may be unlabeled. After washing, and without detecting, another solution of labeled nucleotides may be directed to the substrate, such as for another cycle of transient binding.

In some instances, such as for performing sequencing by ligation, the solution may comprise different probes. For example, the solution may comprise a plurality of oligonucleotide molecules. For example, the oligonucleotide molecules may have a length of about 2 bases, 3 bases, 4 bases, 5 bases, 6 bases, 7 bases, 8 bases, 9 bases, 10 bases or more. The oligonucleotide molecules may be labeled with a dye (e.g., fluorescent dye), as described elsewhere herein. In some instances, such as for detecting repeated sequences in nucleic acid molecules, such as homopolymer repeated sequences, dinucleotide repeated sequences, and trinucleotide repeated sequences, the solution may comprise targeted probes (e.g., homopolymer probe) configured to bind to the repeated sequences. The solution may comprise one type of probe (e.g., nucleotides). The solution may comprise different types of probes (e.g., nucleotides, oligonucleotide molecules, etc.). The solution may comprise different types of probes (e.g., oligonucleotide molecules, antibodies, etc.) for interacting with different types of analytes (e.g., nucleic acid molecules, proteins, etc.). Different solutions comprising different types of probes may be directed to the substrate any number of times, with or without detection between consecutive cycles (e.g., detection may be performed between some consecutive cycles, but not between some others), to sequence or otherwise process the nucleic acid molecule, depending on the type of processing.

Figure 3:
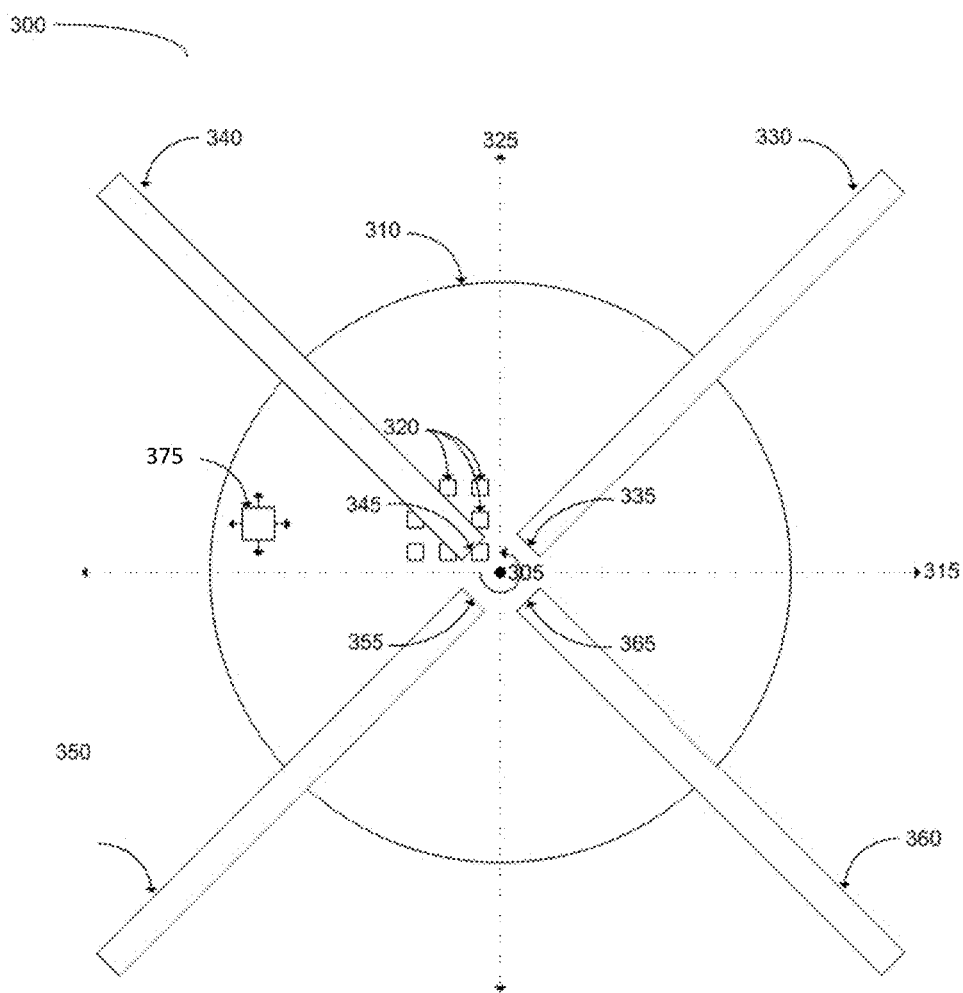
FIG. 3 shows a system for sequencing a nucleic acid molecule.

FIG. 3 shows a system 300 for sequencing a nucleic acid molecule or processing an analyte. The system may be configured to implement the method 200 or 1400. Although the systems (e.g., 300, 400, 500*a*, 500*b*, etc.) are described with respect to processing nucleic acid molecules, the systems may be used to process any other type of biological analyte, as described herein.

The system may comprise a substrate 310. The substrate may comprise any substrate described herein, such as any substrate described herein with respect to FIG. 2. The substrate may comprise an array. The substrate may be open. The array may comprise one or more locations 320 configured to immobilize one or more nucleic acid molecules or analytes. The array may comprise any array described herein, such as any array described herein with respect to method 200. For instance, the array may comprise a plurality of individually addressable locations. The array may comprise a linker (e.g., any binder described herein) that is coupled to the nucleic acid molecule to be sequenced. Alternatively or in combination, the nucleic acid molecule to be sequenced may be coupled to a bead; the bead may be immobilized to the array. The array may be textured. The array may be a patterned array. The array may be planar.

The substrate may be configured to rotate with respect to an axis 305. The axis may be an axis through the center of the substrate. The axis may be an off-center axis. The substrate may be configured to rotate at any rotational velocity described herein, such as any rotational velocity described herein with respect to method 200 or 1400.

The substrate may be configured to undergo a change in relative position with respect to first or second longitudinal axes 315 and 325. For instance, the substrate may be translatable along the first and/or second longitudinal axes (as shown in FIG. 3). Alternatively, the substrate may be stationary along the first and/or second longitudinal axes. Alternatively or in combination, the substrate may be translatable along the axis (as shown in FIG. 4). Alternatively or in combination, the substrate may be stationary along the axis. The relative position of the substrate may be configured to alternate between positions. The relative position of the substrate may be configured to alternate between positions with respect to one or more of the longitudinal axes or the axis. The relative position of the substrate may be configured to alternate between positions with respect to any of the fluid channels described herein. For instance, the relative position of the substrate may be configured to alternate between a first position and a second position. The relative position of the substrate may be configured to alternate between at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 positions. The relative position of the substrate may be configured to alternate between a number of positions that is within a range defined by any two of the preceding values. The first or second longitudinal axes may be substantially perpendicular with the axis. The first or second longitudinal axes may be substantially parallel with the axis. The first or second longitudinal axes may be coincident with the axis.

The system may comprise a first fluid channel 330. The first fluid channel may comprise a first fluid outlet port 335. The first fluid outlet port may be configured to dispense a first fluid to the array. The first fluid outlet port may be configured to dispense any fluid described herein, such as any solution described herein. The first fluid outlet port may be external to the substrate. The first fluid outlet port may not contact the substrate. The first fluid outlet port may be a nozzle. The first fluid outlet port may have an axis that is substantially coincident with the axis. The first fluid outlet port may have an axis that is substantially parallel to the axis.

The system may comprise a second fluid channel 340. The second fluid channel may comprise a second fluid outlet port 345. The second fluid outlet port may be configured to dispense a second fluid to the array. The second fluid outlet port may be configured to dispense any fluid described herein, such as any solution described herein. The second fluid outlet port may be external to the substrate. The second fluid outlet port may not contact the substrate. The second fluid outlet port may be a nozzle. The second fluid outlet port may have an axis that is substantially coincident with the axis. The second fluid outlet port may have an axis that is substantially parallel to the axis.

The first and second fluids may comprise different types of reagents. For instance, the first fluid may comprise a first type of nucleotide, such as any nucleotide described herein, or a nucleotide mixture. The second fluid may comprise a second type of nucleotide, such as any nucleotide described herein, or a nucleotide mixture. Alternatively, the first and second fluids may comprise the same type of reagents (e.g., same type of fluid is dispensed through multiple fluid outlet ports (e.g., nozzles) to increase coating speed). Alternatively or in combination, the first or second fluid may comprise a washing reagent. The first fluid channel 330 and the second fluid channel 340 may be fluidically isolated. Beneficially, where the first and second fluids comprise different types of reagents, each of the different reagents may remain free of contamination from the other reagents during dispensing.

The first fluid outlet port may be configured to dispense the first fluid during rotation of the substrate. The second fluid outlet port may be configured to dispense the second fluid during rotation of the substrate. The first and second fluid outlet ports may be configured to dispense at non-overlapping times. Alternatively, the first and second fluid outlet ports may be configured to dispense at overlapping times, such as when the first fluid and the second fluid comprise the same type of reagents. The substrate may be configured to rotate with a different speed or a different number of rotations when the first and second outlet ports dispense. Alternatively, the substrate may be configured to rotate with the same speed and number of rotations when the first and second outlet ports dispense. During rotation, the array may be configured to direct the first fluid in a substantially radial direction away from the axis. The first fluid outlet port may be configured to direct the first fluid to the array during at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, or at least 1,000,000 full rotations of the substrate. The first fluid outlet port may be configured to direct the first fluid to the array during a number of full rotations that is within a range defined by any two of the preceding values.

The system may comprise a third fluid channel 350 comprising a third fluid outlet port 355 configured to dispense a third fluid. The system may comprise a fourth fluid channel 360 comprising a fourth fluid outlet port 365 configured to dispense a fourth fluid. The third and fourth fluid channels may be similar to the first and second fluid channels described herein. The third and fourth fluids may be the same or different fluids as the first and/or second fluids. In some cases, at least 1, 2, 3, 4, 5, 6, 7, 8, 9, 10, 15, 20 or more fluids (or reagents) may be employed. For example, 5-10 fluids (or reagents) may be employed.

Although FIG. 3 shows a change in position of the substrate, as an alternative or in addition to, one or more of the first, second, third, and fourth fluid channels may be configured to undergo a change in position. For instance, any of the first, second, third, or fourth fluid channel may be translatable along the first and/or second longitudinal axes. Alternatively, any of the first, second, third, or fourth fluid channel may be stationary along the first and/or second longitudinal axes. Alternatively or in addition to, any of the first, second, third, or fourth fluid channel may be translatable along the axis. Alternatively or in addition to, any of the first, second, third, or fourth fluid channel may be stationary along the axis.

The relative position of one or more of the first, second, third, and fourth fluid channels may be configured to alternate between positions with respect to one or more of the longitudinal axes or the axis. For instance, the relative position of any of the first, second, third, or fourth fluid channel may be configured to alternate between a first position and a second position (e.g., by moving such channel, by moving the substrate, or by moving the channel and the substrate). The relative position of any of the first, second, third, or fourth fluid channel may be configured to alternate between at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more positions. The relative position of any of the first, second, third, or fourth fluid channel may be configured to alternate between a number of positions that is within a range defined by any two of the preceding values. The first or second longitudinal axes may be substantially perpendicular to the axis. The first or second longitudinal axes may be substantially parallel to the axis. The first or second longitudinal axes may be coincident with the axis.

Figure 4A:
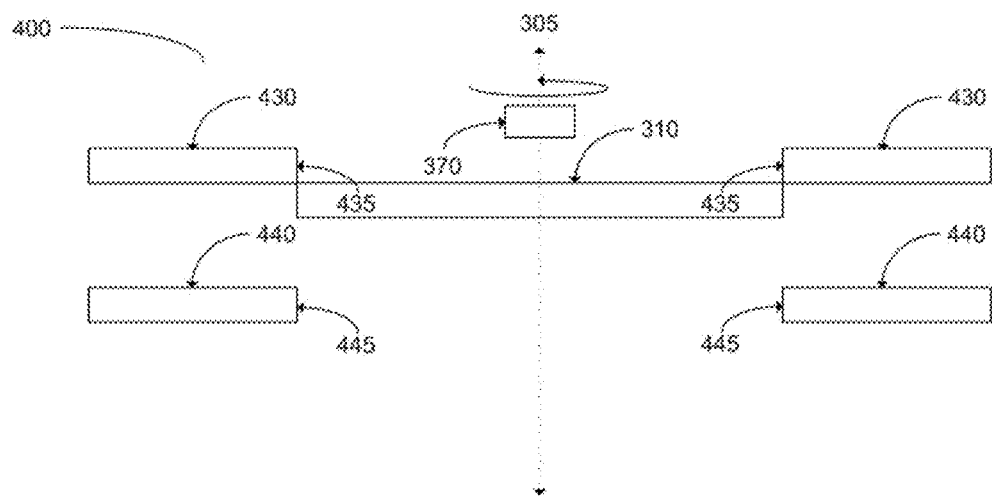
FIG. 4A shows a system for sequencing a nucleic acid molecule in a first vertical level.
Figure 4B:
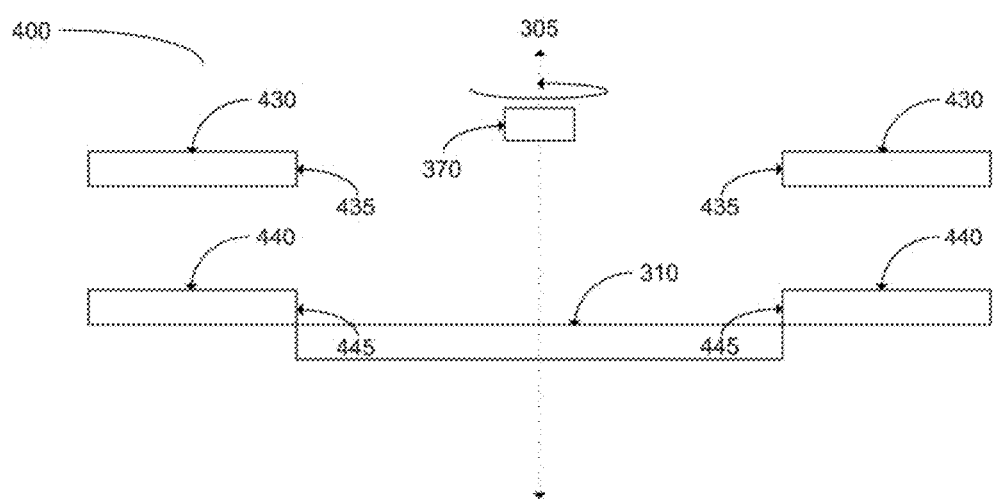
FIG. 4B shows a system for sequencing a nucleic acid molecule in a second vertical level.

In some instances, the system may comprise one or more fluid channels for receiving fluid from the substrate (not shown in FIG. 3). Referring to FIG. 4A-4B, a fifth fluid channel 430 may comprise a first fluid inlet port 435. The first fluid inlet port may be located at a first level of the axis (as shown in FIG. 4). In some instances, the first fluid inlet port may surround the periphery of the substrate 310 (e.g., circularly). The first fluid inlet port may be downstream of and in fluid communication with the substrate 310 when the substrate is in a first position, such as with respect to the axis. The fifth fluid channel may be in fluid communication with the first fluid channel 330. For example, the first fluid inlet port may be configured to receive a solution passing from the first fluid outlet port to the substrate and thereafter off the substrate (e.g., due to inertial forces during rotation of the substrate). For instance, the first fluid inlet port may be configured to receive the solution in a recycling process such as the recycling process described herein with respect to method 200 or 1400. In some instances, the solution received by the fifth fluid channel via the first fluid inlet port may be fed back (e.g., after filtering) to the first fluid channel to be dispensed via the first fluid outlet port to the substrate. The fifth fluid channel and the first fluid channel may define at least part of a first cyclic fluid flow path. The first cyclic fluid flow path may comprise a filter, such as a filter described herein with respect to method 200 or 1400. The filter may be a molecular filter. In other instances, the solution received by the fifth fluid channel may be fed back (e.g., after filtering) to different fluid channels (other than the first fluid channel) to be dispensed via different fluid outlet ports.

The system may comprise a sixth fluid channel 440. The sixth fluid channel may comprise a second fluid inlet port 445. The second fluid inlet port may be located at a second level of the axis (as shown in FIG. 4). In some instances, the second fluid inlet port may surround the periphery of the substrate 310. The second fluid inlet port may be downstream of and in fluid communication with the substrate 310 when the substrate is in a second position, such as with respect to the axis. The sixth fluid channel may be in fluid communication with the second fluid channel 340. For example, the second fluid inlet port may be configured to receive a solution passing from the second fluid outlet port to the substrate and thereafter off the substrate. For instance, the second fluid inlet port may be configured to receive the solution in a recycling process such as the recycling process described herein with respect to method 200 or 1400. In some instances, the solution received by the sixth fluid channel via the second fluid inlet port may be fed back (e.g., after filtering) to the second fluid channel to be dispensed via the second fluid outlet port to the substrate. The sixth fluid channel and the second fluid channel may define at least part of a second cyclic fluid flow path. The second cyclic fluid flow path may comprise a filter, such as a filter described herein with respect to method 200 or 1400. The filter may be a molecular filter.

The system may comprise a shield (not shown) that prevents fluid communication between the substrate and the second fluid inlet port when the substrate is in the first position and between the substrate and the first fluid inlet port when the substrate is in the second position.

The system may further comprise one or more detectors 370. The detectors may be optical detectors, such as one or more photodetectors, one or more photodiodes, one or more avalanche photodiodes, one or more photomultipliers, one or more photodiode arrays, one or more avalanche photodiode arrays, one or more cameras, one or more charged coupled device (CCD) cameras, or one or more complementary metal oxide semiconductor (CMOS) cameras. The cameras may be TDI or other continuous area scanning detectors described herein. The detectors may be fluorescence detectors. The detectors may be in sensing communication with the array. For instance, the detectors may be configured to detect a signal from the array. The signal may be an optical signal. The signal may be a fluorescence signal. The detectors may be configured to detect the signal from the substrate during rotation of the substrate. The detectors may be configured to detect the signal from the substrate when the substrate is not rotating. The detectors may be configured to detect the signal from the substrate following termination of the rotation of the substrate. FIG. 3 shows an example region 375 on the substrate that is optically mapped to the detector.

The system may comprise one or more sources (not shown in FIG. 3) configured to deliver electromagnetic radiation to the substrate. The sources may comprise one or more optical sources. The sources may comprise one or more incoherent or coherent optical sources. The sources may comprise one or more narrow bandwidth or broadband optical sources. The sources may be configured to emit optical radiation having a bandwidth of at most 1 hertz (Hz), at most 2 Hz, at most 5 Hz, at most 10 Hz, at most 20 Hz, at most 50 Hz, at most 100 Hz, at most 200 Hz, at most 500 Hz, at most 1 kilohertz (kHz), at most 2 kHz, at most 5 kHz, at most 10 kHz, at most 20 kHz, at most 50 kHz, at most 100 kHz, at most 200 kHz, at most 500 kHz, at most 1 megahertz (MHz), at most 2 MHz, at most 5 MHz, at most 10 MHz, at most 20 MHz, at most 50 MHz, at most 100 MHz, at most 200 MHz, at most 500 MHz, at most 1 gigahertz (GHz), at most 2 GHz, at most 5 GHz, at most 10 GHz, at most 20 GHz, at most 50 GHz, at most 100 GHz, or a bandwidth that is within a range defined by any two of the preceding values. The sources may comprise one or more lasers. The sources may comprise one or more single-mode laser sources. The sources may comprise one or more multi-mode laser sources. The sources may comprise one or more laser diodes. The source may comprise one or more light emitting diodes (LEDs). The sources may be configured to emit light comprising one or more wavelengths in the ultraviolet (about 100 nm to about 400 nm), visible (about 400 nm to about 700 nm), or infrared (about 700 nm to about 10,000 nm) regions of the electromagnetic spectrum, or any combination therefore. For instances, the sources may emit radiation comprising one or more wavelengths in the range from 600 nm to 700 nm. The sources may emit radiation, either individually or in combination, having an optical power of at least 0.05 watts (W), at least 0.1 W, at least 0.2 W, at least 0.5 W, at least 1 W, at least 2 W, at least 5 W, at least 10 W, or an optical power that is within a range defined by any two of the preceding values. The sources may be configured to interact with molecules on the substrate to generate detectable optical signals that may be detected by the optical detectors. For instance, the sources may be configured to generate optical absorption, optical reflectance, scattering, phosphorescence, fluorescence, or any other optical signal described herein.

The system may comprise a seventh, eighth, ninth, tenth, eleventh, twelfth, thirteenth, fourteenth, fifteenth, sixteenth, seventeenth, eighteenth, nineteenth, or twentieth fluid channel. Each fluid channel may comprise a fluid outlet port or a fluid inlet port in fluid communication with the substrate. For instance, the ninth, tenth, thirteenth, fourteenth, seventeenth, or eighteenth fluid channel may comprise a fluid outlet port. The seventh, eighth, eleventh, twelfth, fifteenth, sixteenth, nineteenth, or twentieth fluid channel may comprise a fluid inlet port. Alternatively, the system may comprise more than twenty fluid channels comprising a fluid outlet port or a fluid inlet port.

Thus, the system may comprise fifth, sixth, seventh, eighth, ninth, or tenth fluid outlet ports. The fifth, sixth, seventh, eighth, ninth, or tenth fluid outlet ports may be configured to dispense fifth, sixth, seventh, eighth, ninth, or tenth fluids to the array. The fifth, sixth, seventh, eighth, ninth, or tenth fluid outlet ports may be configured to dispense any fluid described herein, such as any solution described herein. The fifth, sixth, seventh, eighth, ninth, or tenth fluid outlet ports may be similar to the first, second, third, or fourth fluid outlet ports described herein. Alternatively, the system may comprise more than ten fluid outlet ports.

The fluid channels may be fluidically isolated from one another. For instance, the fluid channels may be fluidically isolated upstream of the first, second, third, fourth, fifth, sixth, seventh, eighth, ninth, or tenth fluid outlet ports. The fifth, sixth, seventh, eighth, ninth, or tenth fluid outlet ports may be external to the substrate. The fifth, sixth, seventh, eighth, ninth, or tenth fluid outlet ports may not contact the substrate. The fifth, sixth, seventh, eighth, ninth, or tenth fluid outlet ports may be a nozzle.

The system may comprise third, fourth, fifth, sixth, seventh, eighth, ninth, or tenth fluid inlet ports. The third, fourth, fifth, sixth, seventh, eighth, ninth, or tenth fluid inlet ports may be in fluid communication with the substrate when the substrate is in a third, fourth, fifth, sixth, seventh, eighth, ninth, or tenth position (e.g., with respect to the axis), respectively. Alternatively, the system may comprise more than ten fluid inlet ports.

The ninth, tenth, thirteenth, fourteenth, seventeenth, or eighteenth fluid channel may be in fluid communication with the seventh, eighth, eleventh, twelfth, fifteenth, or sixteenth, fluid channel, respectively; each pair of fluid channels may define at least part of a third, fourth, fifth, sixth, seventh, eighth, ninth, or tenth cyclic fluid flow path, respectively. Each cyclic fluid flow path may be configured similarly to the first or second cyclic fluid flow paths described herein, with the fluid inlet port of the cyclic fluid flow path configured to receive a solution passing from the fluid outlet port of the cyclic fluid flow path to the substrate. Each cyclic fluid flow path may be configured to receive the solution in a recycling process as described herein. Each cyclic fluid flow path may comprise a filter as described herein.

The fifth, sixth, seventh, eighth, ninth, or tenth fluids may comprise different types of reagents. For instance, the fifth, sixth, seventh, eighth, ninth, or tenth fluid may comprise a fifth, sixth, seventh, eighth, ninth, or tenth type of nucleotide, respectively, such as any nucleotide described herein. Alternatively or in combination, the fifth, sixth, seventh, eighth, ninth, or tenth fluid may comprise a washing reagent.

The fifth, sixth, seventh, eighth, ninth, or tenth fluid outlet port may be configured to dispense the fifth, sixth, seventh, eighth, ninth, or tenth fluid, respectively, during rotation of the substrate. The fifth, sixth, seventh, eighth, ninth, or tenth fluid outlet ports may be configured to dispense at overlapping or non-overlapping times.

FIG. 4A shows a system 400 for sequencing a nucleic acid molecule in a first vertical level. The system may be substantially similar to system 300 described herein or may differ from system 300 in the arrangement of one or more of its elements. The system 400 may comprise substrate 310 described herein. The system 400 may utilize vertical motion parallel to the axis 305 to expose (e.g., make available fluid communication) the substrate 310 to different fluid channels. The system may comprise first fluid channel 330 and first fluid outlet port 335 described herein. The system may comprise second fluid channel 340 and second fluid outlet port 345 described herein. The system may comprise third fluid channel 350 and third fluid outlet port 355 described herein. The system may comprise fourth fluid channel 360 and fourth fluid outlet port 365 described herein. The system may comprise detector 370 described herein. The detector may be in optical communication with the region shown. The system may comprise any optical source described herein (not shown in FIG. 4A).

The fifth fluid channel 430 and first fluid inlet port 435 may be arranged at a first level along the vertical axis, as shown in FIGS. 4A and 4B. The sixth fluid channel 440 and second fluid inlet port 445 may be arranged at a second level along the vertical axis. In this manner, the system may be viewed as comprising first and second fluid flow paths, with each fluid flow path located at a different vertical level. The substrate 310 may be vertically movable between the first level and the second level, from the first level to the second level, and from the second level to the first level. As an alternative, the substrate may be vertically fixed but the levels may be vertically movable with respect to the substrate 310. As another alternative, the substrate and the levels may be vertically movable.

The system 400 may comprise multiple levels. The levels may be vertically orientated relative to one another. The system may include at least 2, 3, 4, 5, 6, 7, 8, 9, 10, 20, 30, 40, 50, 100 or more levels. Each level may include one or more sub-levels (e.g., an incremental level between any two levels). Each level may be for dispensing and/or recovering a different fluid (or reagent). Some levels may be for dispensing the same fluid (or reagent).

While in the first vertical level, the substrate may be in fluid communication with the fifth fluid channel and the first fluid inlet port, but not the sixth fluid channel and the second fluid inlet port. The substrate may be isolated from the sixth fluid channel and the second fluid inlet port by a shield (not shown), as described herein. A first fluid or first solution described herein may be dispensed to the substrate while the substrate is in this first vertical level. For example, any excess of the first solution spinning off the substrate may be received by the first fluid inlet port while the substrate is at the first vertical level. In another example, a washing solution (e.g., dispensed from a different fluid outlet port than the first fluid) spinning off the substrate with some of the first fluid may be received by the first fluid inlet port while the substrate is at the first vertical level. The substrate may then be moved to a second vertical level by vertically moving the substrate. Alternatively, the fifth or sixth fluid channels may be moved vertically. Alternatively or in addition, the substrate and one or more of the fluid channels may be moved relative to the other (e.g., along the axis).

FIG. 4B shows the system 400 for sequencing a nucleic acid molecule in a second vertical level. While in the second vertical level, the substrate may be in fluid communication with the sixth fluid channel and the second fluid inlet port, but not the fifth fluid channel and the first fluid inlet port. The substrate may be isolated from the fifth fluid channel and the first fluid inlet port by a shield (not shown), as described herein. A second fluid or second solution described herein may be dispensed to the substrate while the substrate is in this second vertical position. Alternatively, the first solution may be removed while the substrate is in the second vertical position. In some cases, the first solution may be recycled while the substrate is in the second vertical position. The substrate may then be moved back to the first vertical level, or to another vertical level described herein, by vertically moving the substrate. Alternatively, the fifth or sixth fluid channels may be moved vertically. Alternatively or in addition, the substrate and one or more of the fluid channels may be moved relative to the other (e.g., along the axis).

The third, fourth, fifth, sixth, seventh, eighth, ninth, or tenth fluid inlet ports may be located at third, fourth, fifth, sixth, seventh, eighth, ninth, or tenth vertical levels, respectively. The substrate may be moved to the third, fourth, fifth, sixth, seventh, eighth, ninth, or tenth vertical levels by vertically moving the substrate or by vertically moving the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth fluid flow channels. At any of the first, second, third, fourth, fifth, sixth, seventh, eighth, ninth, tenth or more vertical levels, any fluid solution described herein may be dispensed to the substrate. At any of the first, second, third, fourth, fifth, sixth, seventh, eighth, ninth, tenth or more vertical levels, any fluid solution described herein may be removed from the substrate. At any of the first, second, third, fourth, fifth, sixth, seventh, eighth, ninth, tenth or more vertical levels, any fluid solution described herein may be recycled from the substrate.

Figure 5A:
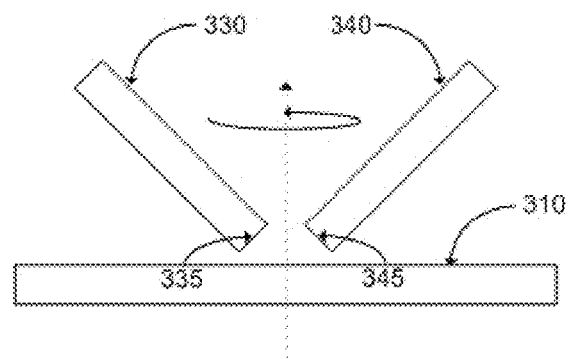
FIG. 5A shows a first example of a system for sequencing a nucleic acid molecule using an array of fluid flow channels.

FIG. 5A shows a first example of a system 500*a* for sequencing a nucleic acid molecule using an array of fluid flow channels. The system may be substantially similar to system 300 or 400 described herein and may differ from system 300 or 400 in the arrangement of one or more of its elements. The system 500*a* may utilize a geometrical arrangement of a plurality of fluid flow channels to expose the substrate to different fluids. The system 500*a* may comprise substrate 310 described herein. The system may comprise first fluid channel 330 and first fluid outlet port 335 described herein. The system may comprise second fluid channel 340 and second fluid outlet port 345 described herein. The system may comprise fifth fluid channel 430 and first fluid inlet port 435 described herein (not shown in FIG. 5A). The system may comprise sixth fluid channel 440 and second fluid inlet port 445 described herein (not shown in FIG. 5A). The system may comprise detector 370 described herein (not shown in FIG. 5A). The system may comprise any optical source described herein (not shown in FIG. 5A).

The first fluid channel and first fluid outlet port may be arranged at a first position, as shown in FIG. 5A. The second fluid channel and second fluid outlet port may be arranged at a second position. The system may be configured to dispense a first fluid from the first fluid outlet port and a second fluid from the second fluid outlet port.

The system may comprise any of third, fourth, seventh, eighth, ninth, tenth, eleventh, twelfth, thirteenth, fourteenth, fifteenth, sixteenth, seventeenth, eighteenth, nineteenth, or twentieth fluid channels described herein. The system may comprise any of third, fourth, fifth, sixth, seventh, eighth, ninth, or tenth fluid outlet ports described herein. The system may comprise any of third, fourth, fifth, sixth, seventh, eighth, ninth, or tenth fluid inlet ports described herein.

The third, fourth, fifth, sixth, seventh, eighth, ninth, or tenth fluid outlet ports may be located at third, fourth, fifth, sixth, seventh, eighth, ninth, or tenth positions, respectively. The system may be configured to dispense a third, fourth, fifth, sixth, seventh, eighth, ninth, or tenth fluid from the third, fourth, fifth, sixth, seventh, eighth, ninth, or tenth fluid outlet port, respectively.

Any two or more of the first, second, third, fourth, seventh, eighth, ninth, tenth, eleventh, twelfth, thirteenth, fourteenth, fifteenth, sixteenth, seventeenth, eighteenth, nineteenth, twentieth, or more fluid channels may form an array of fluid flow channels. The array of fluid flow channels may be moveable. Alternatively, the array of fluid flow channels may be at a fixed location with respect to the substrate. Each fluid flow channel of the array of fluid flow channels may be positioned such that a longitudinal axis of the fluid flow channel forms an angle with the rotational axis of the substrate. The angle may have a value of at least 0 degrees, at least 5 degrees, at least 10 degrees, at least 15 degrees, at least 20 degrees, at least 25 degrees, at least 30 degrees, at least 35 degrees, at least 40 degrees, at least 45 degrees, at least 50 degrees, at least 55 degrees, at least 60 degrees, at least 65 degrees, at least 70 degrees, at least 75 degrees, at least 80 degrees, at least 85 degrees, or at least 90 degrees. The angle may have a value that is within a range defined by any two of the preceding values. Each fluid channel of the array of fluid channels may make a similar angle with the substrate. Alternatively, one or more fluid channels may make different angles with the substrate.

Figure 5B:
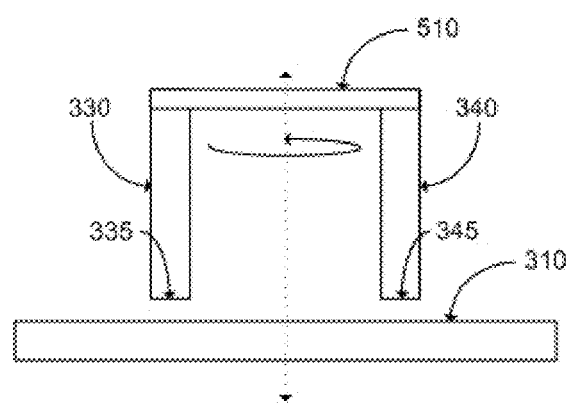
FIG. 5B shows a second example of a system for sequencing a nucleic acid molecule using an array of fluid flow channels.

FIG. 5B shows a second example of a system 500*b* for sequencing a nucleic acid molecule using an array of fluid flow channels.

The system may be substantially similar to system 300 or 400 described herein and may differ from system 300 or 400 in the arrangement of one or more of its elements. The system 500*b* may utilize a plurality of fluid flow channels configured to move relative to the substrate to expose the substrate to different fluids. The system 500*b* may comprise substrate 310 described herein. The system may comprise first fluid channel 330 and first fluid outlet port 335 described herein. The system may comprise second fluid channel 340 and second fluid outlet port 345 described herein. The system may comprise fifth fluid channel 430 and first fluid inlet port 435 described herein (not shown in FIG.

5B). The system may comprise sixth fluid channel 440 and second fluid inlet port 445 described herein (not shown in FIG. 5B). The system may comprise detector 370 described herein (not shown in FIG. 5B). The system may comprise any optical source described herein (not shown in FIG. 5B).

The first fluid channel and first fluid outlet port may be attached to a fluid dispenser 510. The fluid dispenser may be a moveable fluid dispenser, such as comprising a moveable gantry arm, as shown in FIG. 5B. As an alternative, the fluid dispenser may be fixed or stationary. The fluid dispenser may be configured to move to a first position to dispense a first fluid from the first fluid outlet port. The second fluid channel and second fluid outlet port may also be attached to the fluid dispenser. The fluid dispenser may be configured to move to a second position to dispense a second fluid from the second fluid outlet port.

The system may comprise any of third, fourth, seventh, eighth, ninth, tenth, eleventh, twelfth, thirteenth, fourteenth, fifteenth, sixteenth, seventeenth, eighteenth, nineteenth, or twentieth fluid channels described herein. The system may comprise any of third, fourth, fifth, sixth, seventh, eighth, ninth, or tenth fluid outlet ports described herein. The system may comprise any of third, fourth, fifth, sixth, seventh, eighth, ninth, or tenth fluid inlet ports described herein.

The third, fourth, fifth, sixth, seventh, eighth, ninth, or tenth fluid outlet ports may be attached to the fluid dispenser. The fluid dispenser may be configured to move to a third, fourth, fifth, sixth, seventh, eighth, ninth, or tenth position to dispense a third, fourth, fifth, sixth, seventh, eighth, ninth, or tenth fluid from the third, fourth, fifth, sixth, seventh, eighth, ninth, or tenth fluid outlet port, respectively. Alternatively, the fluid dispenser may be kept stationary and the substrate 310 may be moved to different positions to receive different fluids.

Figure 6:
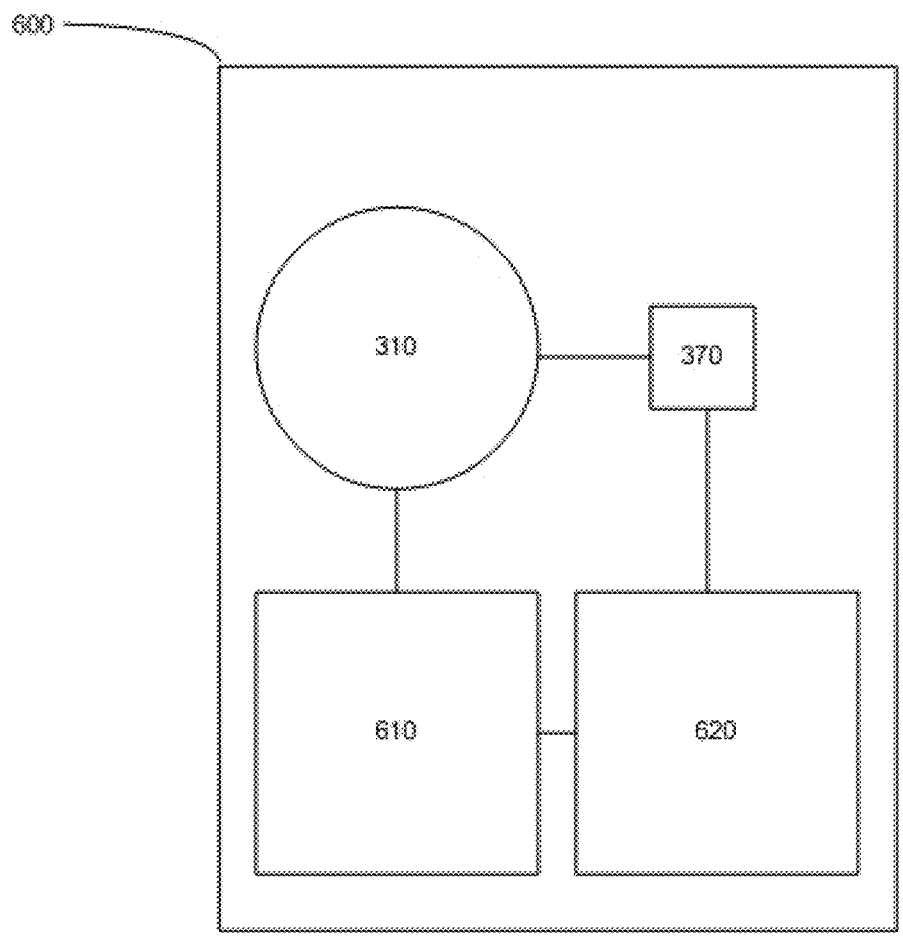
FIG. 6 shows a computerized system for sequencing a nucleic acid molecule.

FIG. 6 shows a computerized system 600 for sequencing a nucleic acid molecule. The system may comprise a substrate 310, such as a substrate described herein with respect to method 200 or 1400, or system 300. The system may further comprise a fluid flow unit 610. The fluid flow unit may comprise any element associated with fluid flow described herein, such as any or all of elements 330, 335, 340, 345, 350, 355, 360, 365, 430, 435, 440, 445, and 370 described herein with respect to system 300, 400, 500a, or 500b. The fluid flow unit may be configured to direct a solution comprising a plurality of nucleotides described herein to an array of the substrate prior to or during rotation of the substrate. The fluid flow unit may be configured to direct a washing solution described herein to an array of the substrate prior to or during rotation of the substrate. In some instances, the fluid flow unit may comprise pumps, compressors, and/or actuators to direct fluid flow from a first location to a second location. With respect to method 1400, the fluid flow system may be configured to direct any solution to the substrate 310. With respect to method 1400, the fluid flow system may be configured to collect any solution from the substrate 310. The system may further comprise a detector 370, such as any detector described herein with respect to system 300 or 400. The detector may be in sensing communication with the array of the substrate.

The system may further comprise one or more computer processors 620. The one or more processors may be individually or collectively programmed to implement any of the methods described herein. For instance, the one or more processors may be individually or collectively programmed to implement any or all operations of the methods of the present disclosure, such as method 200 or 1400. In particular, the one or more processors may be individually or collectively programmed to: (i) direct the fluid flow unit to direct the solution comprising the plurality of nucleotides across the array during or prior to rotation of the substrate; (ii) subject the nucleic acid molecule to a primer extension reaction under conditions sufficient to incorporate at least one nucleotide from the plurality of nucleotides into a growing strand that is complementary to the nucleic acid molecule; and (iii) use the detector to detect a signal indicative of incorporation of the at least one nucleotide, thereby sequencing the nucleic acid molecule.

While the rotational system has been described with respect to sequencing applications, such rotational schemes may be used for other applications (e.g., pre-sequencing applications, sample preparation, etc.), such as template seeding and surface amplification processes. For example, the reagents dispensed during or prior to rotation of the substrate may be tailored to the other applications. While the reagents dispensed to the substrate in the rotational system have been described with respect to nucleotides, any reagent that may react with a nucleic acid molecule (or any other molecule or cell) immobilized to the substrate, such as probes, adaptors, enzymes, and labelling reagents, may be dispensed to the substrate prior to, during, or subsequent to rotation to achieve high speed coating of the substrate with the dispensed reagents.

The systems for sequencing nucleic acid molecules described herein (such as any of systems 300, 400, 500a, or 500b, or any other system described herein), or any element thereof, may be environmentally controlled. For instance, the systems may be maintained at a specified temperature or humidity. The systems (or any element thereof) may be maintained at a temperature of at least 20 degrees Celsius (° C.), at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at most 100° C., at most 95° C., at most 90° C., at most 85° C., at most 80° C., at most 75° C., at most 70° C., at most 65° C., at most 60° C., at most 55° C., at most 50° C., at most 45° C., at most 40° C., at most 35° C., at most 30° C., at most 25° C., at most 20° C., or at a temperature that is within a range defined by any two of the preceding values. Different elements of the system may be maintained at different temperatures or within different temperature ranges, such as the temperatures or temperature ranges described herein. Elements of the system may be set at temperatures above the dewpoint to prevent condensation. Elements of the system may be set at temperatures below the dewpoint to collect condensation.

The systems (or any element thereof) may be maintained at a relative humidity of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at most 100%, at most 95%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5%, or a relative humidity that is within a range defined by any two of the preceding values. The systems (or any element thereof) may be contained within a sealed container, housing, or chamber that insulates the system (or any element thereof) from the external environment, allowing for the control of the temperature or humidity. An environmental unit (e.g., humidifiers, heaters, heat exchangers, compressors, etc.) may be configured to regulate one or more operating conditions in each environment. In some instances, each environment may be regulated by independent environmental units. In some instances, a single environmental unit may regulate a plurality of environments. In some instances, a plurality of environmental units may, individually or collectively, regulate the different environments. An environmental unit may use active methods or passive methods to regulate the operating conditions. For example, the temperature may be controlled using heating or cooling elements. The humidity may be controlled using humidifiers or dehumidifiers. In some instances, a part of the internal environment within the container or chamber may be further controlled from other parts of the internal environment. Different parts may have different local temperatures, pressures, and/or humidity. For example, the internal environment may comprise a first internal environment and a second internal environment separated by a seal. In some instances, the seal may comprise an immersion objective lens. For example, an immersion objective lens may be part of a seal that separates the internal environment in the container into a first internal environment having 100% (or substantially 100%) humidity and a second environment having one or more of an ambient temperature, pressure or humidity. The immersion objective lens may be in contact with one or more of a detector and imaging lens.

Optical Systems for Imaging a Rotating Substrate

For a substrate exhibiting a smooth, stable rotational motion, it may be simpler or more cost-effective to image the substrate using a rotational motion system instead of a rectilinear motion system. Rotational motion, as used herein, may generally refer to motion in a polar coordinate system that is predominantly in an angular direction. Prior optical imaging systems have utilized time delay and integration (TDI) cameras to achieve high duty cycles and maximum integration times per field point. A TDI camera may use a detection principle similar to a charge coupled device (CCD) camera. Compared to a CCD camera, the TDI camera may shift electric charge, row by row, across a sensor at the same rate as an image traverses the focal plane of the camera. In this manner, the TDI camera may allow longer image integration times while reducing artifacts such as blurring that may be otherwise associated with long image exposure times. A TDI camera may perform integration while simultaneously reading out and may therefore have a higher duty cycle than a camera that performs these functions in a serial manner. Use of a TDI camera to extend integration times may be important for high throughput fluorescent samples, which may be limited in signal production by fluorescent lifetimes. For instance, alternative imaging techniques, such as point scanning, may be precluded from use in high throughput systems as it may not be possible to acquire an adequate number of photons from a point in the limited amount of integration time required for high speeds due to limits imposed by fluorescence lifetimes of dye molecules.

Prior TDI detection schemes may be limited in their applicability to the imaging of rotating systems, such as the rotating nucleic acid sequencing systems described herein. When scanning a curved path, such as the curved path generated by the rotating systems described herein, a TDI sensor may only be able to shift charge (commonly referred to as clocking or line triggering) at the correct rate for a single velocity. For instance, the TDI sensor may only be able to clock at the correct rate along an arc located at a particular distance from the center of rotation. Locations at smaller distances from the center of rotation may clock too quickly, while locations at smaller distances from the center of rotation may clock too slowly. In either case, the mismatch between the rotational speed of the rotating system and the clock rate of the TDI sensor may cause blurring that varies with the distance of a location from the center of the rotating system. This effect may be referred to as tangential velocity blur. The tangential velocity blur may produce an image distortion of a magnitude a defined by equation (2):

$$\sigma = \frac{hw}{2R} = \frac{A}{2R} \qquad (2)$$

Here, h, w, and A are the effective height, width, and area, respectively, of the TDI sensor projected to the object plan. R is the distance of the center of the field from the center of the rotating system. The effective height, width, and area of the sensor are the height, width, and area, respectively, that produce signal. In the case of fluorescence imaging, the effective height, width, and area of the sensor may be the height, width, and area, respectively, that correspond to illuminated areas on the sample. In addition to the tangential velocity blur effect, Equation (2) implies that increasing sensor area, which may be a goal of many imaging systems, may introduce imaging complications for TDI imaging of rotating systems. Consequently, prior TDI systems may require small image sensors to image rotating systems and may thus be unfit for simultaneous high-sensitivity and high-throughput imaging of such systems.

Described herein are systems and methods for imaging rotating systems that can address at least the abovementioned problems. The systems and methods described herein may benefit from higher efficiency, such as from faster imaging time.

Figure 7:
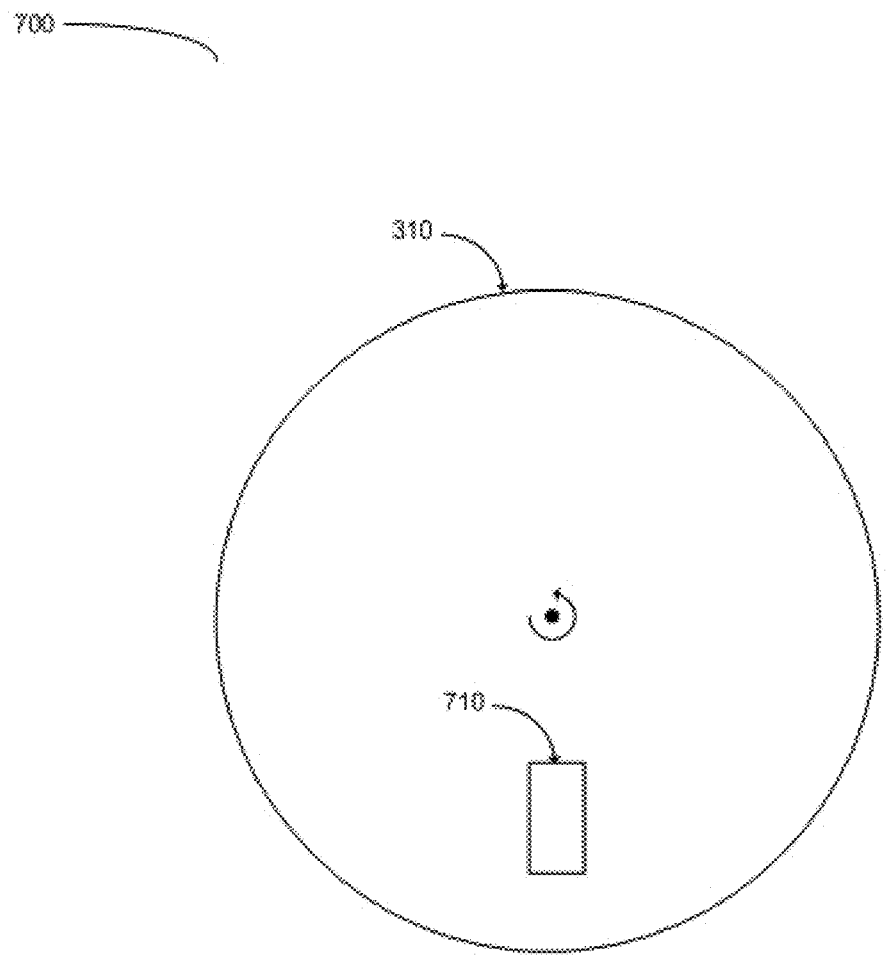
FIG. 7 shows an optical system for continuous area scanning of a substrate during rotational motion of the substrate.

FIG. 7 shows an optical system 700 for continuous area scanning of a substrate during rotational motion of the substrate. The term "continuous area scanning (CAS)," as used herein, generally refers to a method in which an object in relative motion is imaged by repeatedly, electronically or computationally, advancing (clocking or triggering) an array sensor at a velocity that compensates for object motion in the detection plane (focal plane). CAS can produce images having a scan dimension larger than the field of the optical system. TDI scanning may be an example of CAS in which the clocking entails shifting photoelectric charge on an area sensor during signal integration. For a TDI sensor, at each clocking step, charge may be shifted by one row, with the last row being read out and digitized. Other modalities may accomplish similar function by high speed area imaging and co-addition of digital data to synthesize a continuous or stepwise continuous scan.

The optical system may comprise one or more sensors 710. As shown, in FIG. 7, the sensors may be optically projected to the sample. The optical system may comprise one or more optical elements, such as the optical element 810 described in the context of FIG. 8. The system may comprise a plurality of sensors, such as at least 2, at least 5, at least 10, at least 20, at least 50, at least 100, at least 200, at least 500, or at least 1,000 sensors. The system may comprise a at least 2, at least 4, at least 8, at least 16, at least 32, at least 64, at least 128, at least 256, at least 512, or at least 1,024 sensors. The plurality of sensors may be the same type of sensor or different types of sensors. Alternatively, the system may comprise at most about 1000, 500, 200, 100, 50, 20, 10, 5, 2, or fewer sensors. Alternatively, the system may comprise at most about 1024, 512, 256, 128, 64, 32, 16, 8, 4, 2, or fewer sensors. The system may comprise a number of sensors that is within a range defined by any two of the preceding values. The sensors may comprise image sensors. The sensors may comprise CCD cameras. The sensors may comprise CMOS cameras. The sensors may comprise TDI cameras. The sensors may comprise pseudo-TDI rapid frame rate sensors. The sensors may comprise CMOS TDI or hybrid cameras. The sensors may be integrated together in a single package. The sensors may be integrated together in a single semiconductor substrate. The system may further comprise any optical source described herein (not show in FIG. 7).

The sensors may be configured to detect an image from a substrate, such as the substrate 310 described herein, during rotational motion of the substrate. The rotational motion may be with respect to an axis of the substrate. The axis may be an axis through the center of the substrate. The axis may be an off-center axis. The substrate may be configured to rotate at any rotational speed described herein. The rotational motion may comprise compound motion. The compound motion may comprise rotation and an additional component of radial motion. The compound motion may be a spiral (or substantially spiral). The compound motion may be a ring (or substantially ring-like).

Each sensor may be located at a focal plane in optical communication with the substrate. The focal plane may be the approximate plane in an imaging system (e.g., CAS sensor) at which an image of a region of the substrate forms. The focal plane may be segmented into a plurality of regions, such as at least 2, at least 5, at least 10, at least 20, at least 50, at least 100, at least 200, at least 500, or at least 1000 regions. The focal plane may be segmented into at least 2, at least 4, at least 8, at least 16, at least 32, at least 64, at least 128, at least 256, at least 512, or at least 1,024 regions. The focal plane may be segmented into a number of regions that is within a range defined by any two of the preceding values. The focal plane may be segmented into a plurality of regions along an axis substantially normal to a projected direction of the rotational motion. An angle between the axis and the projected direction of the rotational motion may be no more than 1 degree, no more than 2 degrees, no more than 3 degrees, no more than 4 degrees, no more than 5 degrees, no more than 6 degrees, no more than 7 degrees, no more than 8 degrees, no more than 9 degrees, no more than 10 degrees, no more than 11 degrees, no more than 12 degrees, no more than 13 degrees, no more than 14 degrees, or no more than 15 degrees from normal, or an angle that is within a range defined by any two of the preceding values. The focal plane may be segmented into a plurality of regions along an axis parallel to a projected direction of the rotational motion. The focal plane may be spatially segmented. For instance, the focal plane may be segmented by abutting or otherwise arranging a plurality of sensors in a single focal plane and clocking each of the sensors independently.

Alternatively or in combination, the focal plane may be segmented by optically splitting the focal plane into a plurality of separate paths, each of which may form a sub-image on an independent sensor of the plurality of sensors and which may be clocked independently. The focal path may be optically split using one or more optical elements, such as a lens array, mirror, or prism. Each sensor of the plurality of sensors may be in optical communication with a different region of the rotating substrate. For instance, each sensor may image a different region of the rotating substrate. Each sensor of the plurality of sensors may be clocked at a rate appropriate for the region of the rotating substrate imaged by the sensor, which may be based on the distance of the region from the center of the rotating substrate or the tangential velocity of the region.

One or more of the sensors may be configured to be in optical communication with at least 2 of the plurality of regions in the focal plane. One or more of the sensors may comprise a plurality of segments. Each segment of the plurality of segments may be in optical communication with a region of the plurality of regions. Each segment of the plurality of segments may be independently clocked. The independent clocking of a segment may be linked to a velocity of an image in an associated region of the focal plane. The independent clocking may comprise TDI line rate or pseudo-TDI frame rate.

The system may further comprise a controller (not shown). The controller may be operatively coupled to the one or more sensors. The controller may be programmed to process optical signals from each region of the rotating substrate. For instance, the controller may be programmed to process optical signals from each region with independent clocking during the rotational motion. The independent clocking may be based at least in part on a distance of each region from a projection of the axis and/or a tangential velocity of the rotational motion. The independent clocking may be based at least in part on the angular velocity of the rotational motion. While a single controller has been described, a plurality of controllers may be configured to, individually or collectively, perform the operations described herein.

Figure 8A:
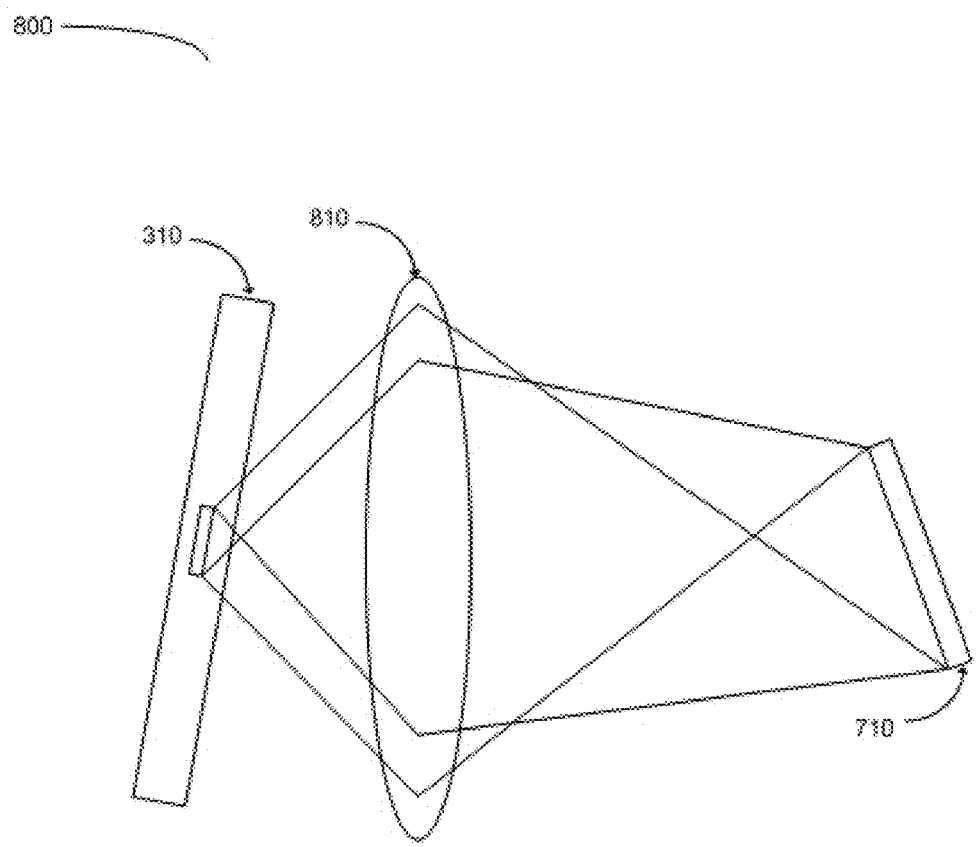
FIG. 8A shows an optical system for imaging a substrate during rotational motion of the substrate using tailored optical distortions.

FIG. 8A shows an optical system 800 for imaging a substrate during rotational motion of the substrate using tailored optical distortions. The optical system may comprise one or more sensors 710. The one or more sensors may comprise any sensors described herein. The optical system may comprise any optical sources described herein (not shown in FIG. 8A).

The sensors may be configured to detect an image from a substrate, such as the substrate 310 described herein, during rotational motion of the substrate. The rotational motion may be with respect to an axis of the substrate. The axis may be an axis through the center of the substrate. The axis may be an off-center axis. The substrate may be configured to rotate at any rotational speed described herein.

The system 800 may further comprise an optical element 810. The optical element may be in optical communication with the sensor. The optical element may be configured to direct optical signals from the substrate to the sensor. The optical element may produce an optical magnification gradient across the sensor. At least one of the optical element and the sensor may be adjustable. For instance, at least one of the optical element and the sensor may be adjustable to generate an optical magnification gradient across the sensor. The optical magnification gradient may be along a direction substantially perpendicular to a projected direction of the rotational motion of the substrate. The optical element may be configured to rotate, tilt, or otherwise be positioned to engineer the optical magnification gradient. The optical element may produce a magnification that scales approximately as the inverse of the distance to the axis of the substrate. The magnification gradient may be produced by selecting a relative orientation of the substrate, optical element, and sensor. For instance, the magnification gradient may be produced by tilting the object and image planes as shown in FIG. 8A. The magnification gradient may display geometric properties. For instance, a ratio of a first optical magnification of a first region at a minimum distance from the center of the substrate to a second optical magnification of a second region at a maximum distance from the center of the substrate may be substantially equal to a ratio of the maximum distance to the minimum distance. In this manner, the first and second optical magnifications may be in the same ratio as the radii of their respective sample regions. Although the system 800 as shown includes a single optical element 810, the system 800 may include a plurality of optical elements, such as at least 2, 3, 4, 5, 6, 7, 8, 9, 10, 20, 30, 40, 50, 100, or more optical elements. Various arrangements or configurations of optical elements may be employed. For example, the system 800 may include a lens and a mirror for directing light.

Figure 8B:
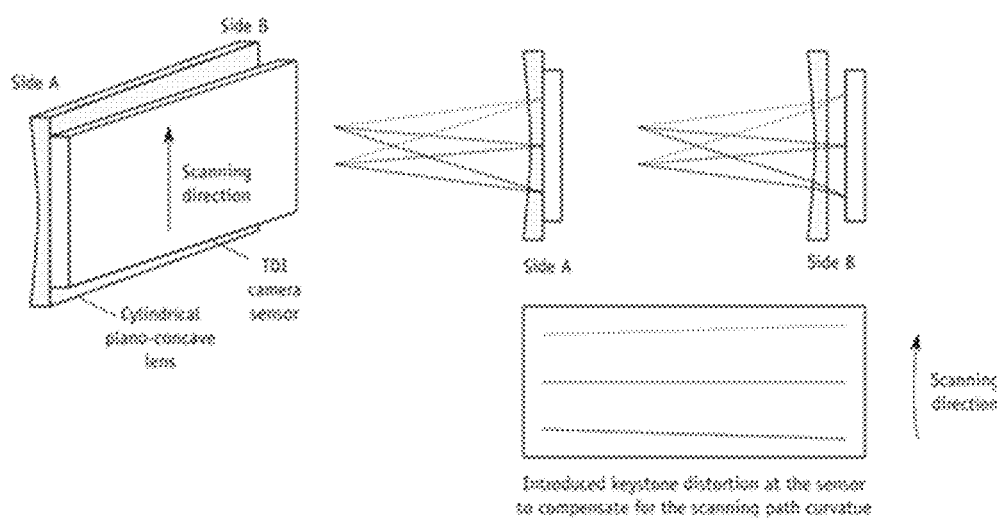
FIG. 8B shows an example of induced tailored optical distortions using a cylindrical lens.

The optical element may be a lens. The lens may be a field lens. The lens may be a cylindrical lens (for instance, as shown in FIG. 8B). The cylindrical lens may be plano-cylindrical. The lens may be plano-concave or plano-convex. The cylindrical lens may have a positive or negative curvature. The curvature of the cylindrical lens may vary. The curvature of the cylindrical lens may vary in a direction perpendicular to a projected direction of rotational motion. The shape of a surface of the lens may be conical. The lens may be tilted with respect to the sensor, thereby producing an anamorphic magnification gradient. The tilt of the lens may be adjustable, thereby producing an adjustable anamorphic magnification gradient.

FIG. 8B shows an example of induced tailored optical distortions using a cylindrical lens. As shown in FIG. 8B, a cylindrical lens may have a first side A and a second side B. The first side A may be located closer to an image sensor (such as a TDI camera sensor described herein) than the second side B. Such a configuration may be achieved by tilting the cylindrical lens in relation to the image sensor. In this manner, the cylindrical lens may direct light to different locations on the image sensor, with light passing through side B being directed more divergently than light passing through side A. In this manner, the cylindrical lens may provide an anamorphic magnification gradient across the image sensor, as depicted in FIG. 8B.

Tilting of the lens may provide an anamorphic magnification gradient across the sensor. The tilt and hence anamorphic gradient may be in a direction substantially perpendicular to the image motion on the sensor. The tilt of the lens may be adjustable. The adjustment may be automatic by using a controller. The adjustment may be coupled to the radius of the scanned substrate region relative to the substrate axis of rotation. The ratio of the minimum to maximum anamorphic magnification may be exactly or approximately in the ratio of the minimum to maximum projected radii relative to the substrate axis of rotation.

Alternatively or in combination, a gradient in the radius of curvature of the lens may provide an anamorphic magnification gradient across the sensor. The curvature gradient may be in a direction substantially direction perpendicular to the image motion on the sensor.

The system may further comprise a controller (not shown). The controller may be operatively coupled to the sensor and the optical element. The controller may be programmed to direct the adjustment of at least one of the sensor and the optical element to generate an optical magnification gradient across the sensor. The magnification gradient may be generated along a direction substantially perpendicular to a projected direction of the rotational motion. The controller may be programmed to direct adjustment of the sensor and/or the optical element to produce an anamorphic optical magnification gradient. The optical magnification gradient may be across the sensor in a direction substantially perpendicular to a projected direction of the rotational motion. The controller may be programmed to direct rotation or tilt of the optical element. The controller may be programmed to direct adjustment of the magnification gradient. For instance, the controller may be programmed to direct adjustment of the magnification gradient at least in part on a radial range of a field dimension relative to a projection about the axis of the substrate. The controller may be programmed to subject the rotational motion to the substrate. While a single controller has been described, a plurality of controllers may be configured to, individually or collectively, perform the operations described herein.

The optical systems described herein may utilize multiple scan heads. The multiple scan heads may be operated in parallel along different imaging paths. For instance, the scan heads may be operated to produce interleaved spiral scans, nested spiral scans, interleaved ring scans, nested ring scans, or a combination thereof.

Figure 9A:
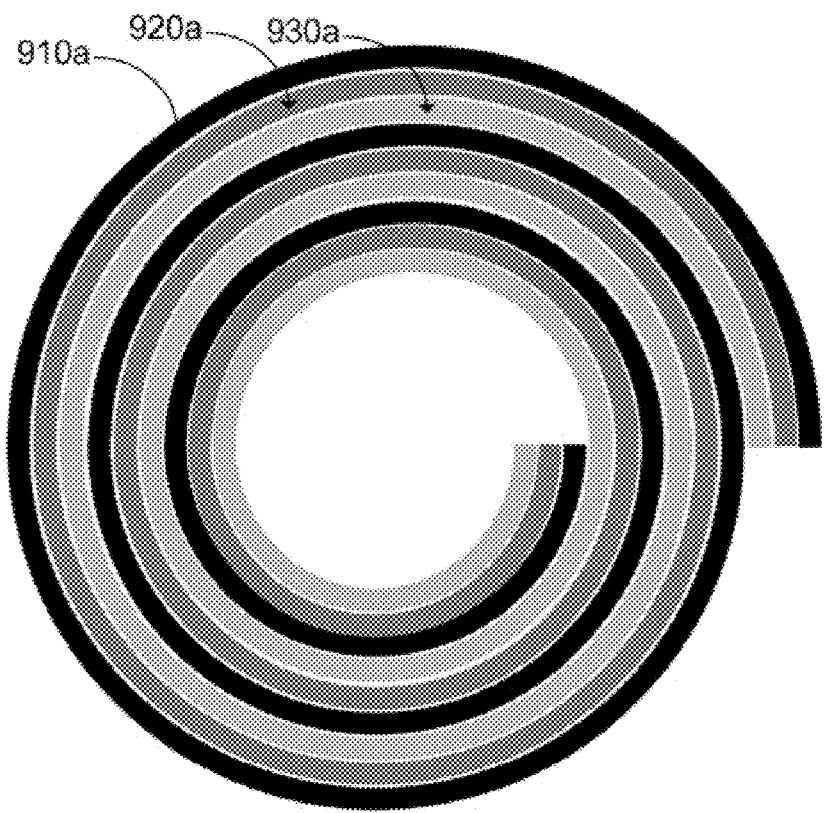
FIG. 9A shows a first example of an interleaved spiral imaging scan.

FIG. 9A shows a first example of an interleaved spiral imaging scan. A first region of a scan head may be operated along a first spiral path 910a. A second region of a scan head may be operated along a second spiral path 920a. A third region of a scan head may be operated along a third spiral path 930a. Each of the first, second, and third regions may be independently clocked. The scan head may comprise any optical systems described herein. The use of multiple imaging scan paths may increase imaging throughput by increasing imaging rate.

Figure 9B:
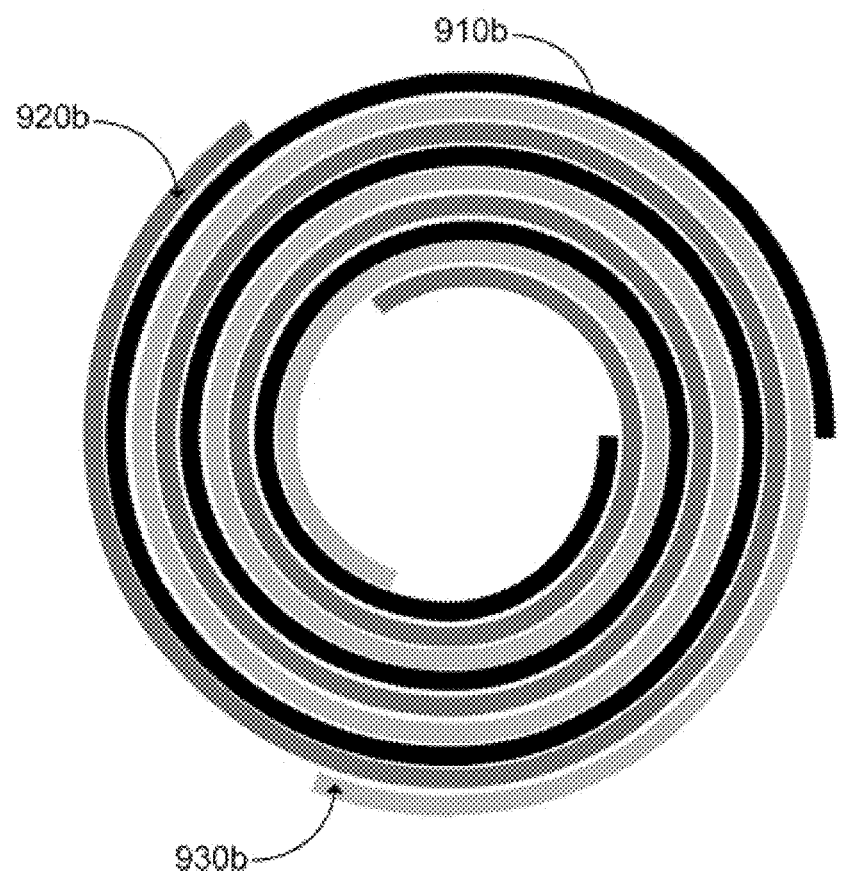
FIG. 9B shows a second example of an interleaved imaging scan.

FIG. 9B shows a second example of an interleaved spiral imaging scan. A first scan head may be operated along a first spiral path 910b. A second scan head may be operated along a second spiral path 920b. A third scan head may be operated along a third spiral path 930b. Each of the first, second, and third scan heads may be independently clocked or clocked in unison. Each of the first, second, and third scan heads may comprise any optical systems described herein. The use of multiple imaging scan paths may increase imaging throughput by increasing net imaging rate. Throughput of the optical system can be multiplied by operating many scan heads of a field width in parallel. For example, each scan head may be fixed at a different angle relative to the center of substrate rotation.

Figure 9C:
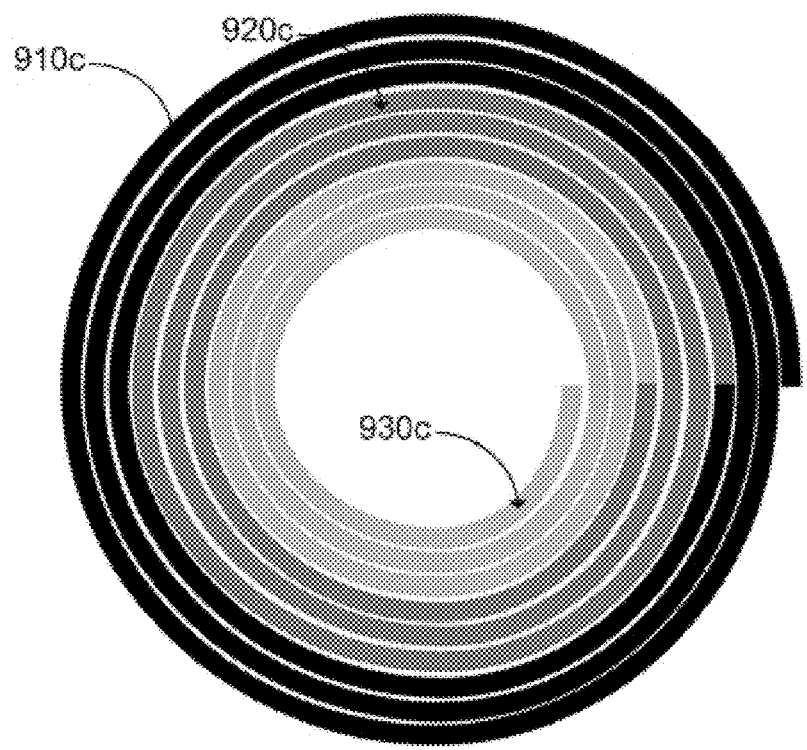
FIG. 9C shows an example of a nested imaging scan.

FIG. 9C shows an example of a nested spiral imaging scan. A first scan head may be operated along a first spiral path 910c. A second scan head may be operated along a second spiral path 920c. A third scan head may be operated along a third spiral path 930c. Each of the first, second, and third scan heads may be independently clocked. Each of the first, second, and third scan heads may comprise any optical systems described herein. The use of multiple imaging scan paths may increase imaging throughput by increasing imaging rate. The scan heads may move together in the radial direction. Throughput of the optical system can be multiplied by operating many scan heads of a field width in parallel. For example, each scan head may be fixed at a different angle. The scans may be in discrete rings rather or spirals.

While FIGS. 9A-9C illustrate three imaging paths, there may be any number of imaging paths and any number of scan heads. For example, there may be at least about 2, 3, 4, 5, 6, 7, 8, 9, 10, or more imaging paths or scan heads. Alternatively, there may be at most about 10, 9, 8, 7, 6, 5, 4, 3, 2, or less imaging paths or scan heads. Each scan head may be configured to receive light having a wavelength within a given wavelength range. For instance, the first scan head may be configured to receive first light having a wavelength within a first wavelength range. The second scan head may be configured to receive second light having a wavelength within a second wavelength range. The third scan head may be configured to receive third light having a wavelength within a third wavelength range. Similarly, fourth, fifth, sixth, seventh, eighth, ninth, or tenth scan heads may be configured to receive fourth, fifth, sixth, seventh, eighth, ninth, or tenth light, respectively, each of the fourth, fifth, sixth, seventh, eighth, ninth, or tenth light having a wavelength within a fourth, fifth, sixth, seventh, eighth, ninth, or tenth wavelength range, respectively. The first, second, third, fourth, fifth, sixth, seventh, eighth, ninth, or tenth wavelength ranges may be identical. The first, second, third, fourth, fifth, sixth, seventh, eighth, ninth, or tenth wavelength ranges may partially overlap. Any 2, 3, 4, 5, 6, 7, 8, 9, or 10 of the first, second, third, fourth, fifth, sixth, seventh, eighth, ninth, or tenth wavelength ranges may be distinct. The first, second, third, fourth, fifth, sixth, seventh, eighth, ninth, or tenth wavelength ranges may be in the ultraviolet, visible, or near infrared regions of the electromagnetic spectrum. Each of the first, second, third, fourth, fifth, sixth, seventh, eighth, ninth, or tenth wavelength ranges may comprise a wavelength emitted by a fluorophore, dye, or quantum dot described herein. In this manner, the system may be configured to detect optical signals from a plurality of fluorophores, dyes, or quantum dots.

Figure 10:
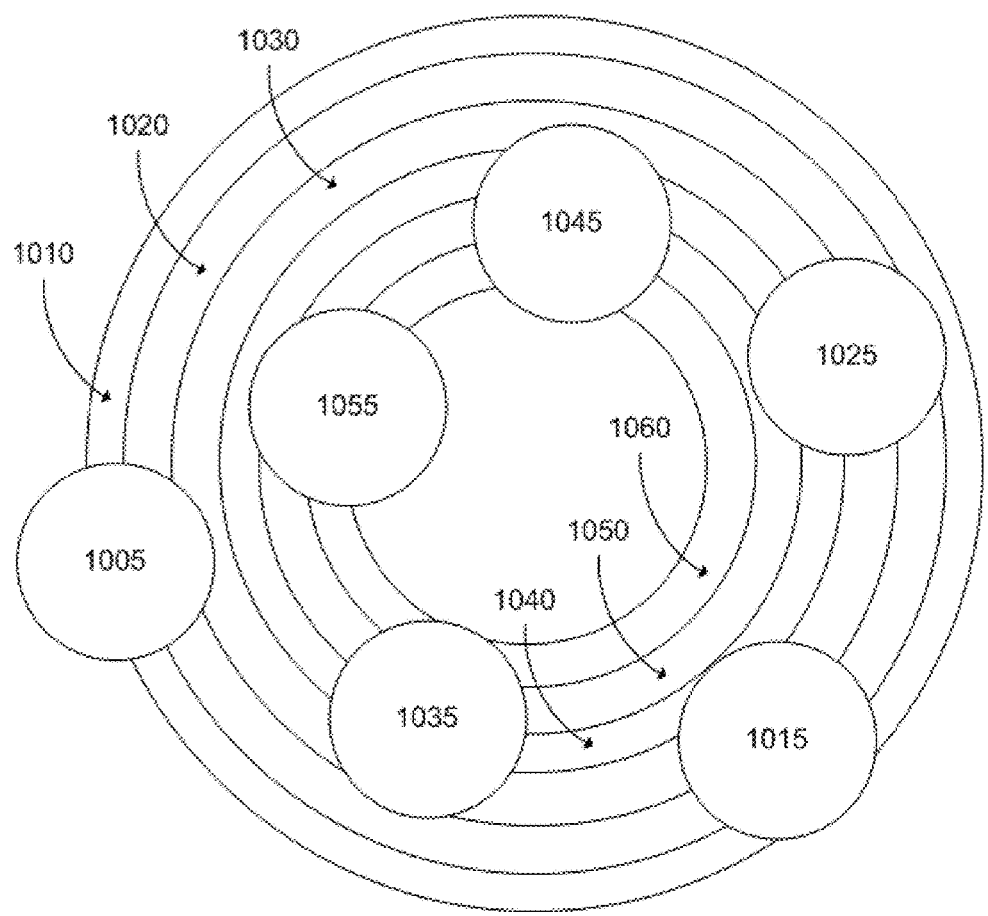
FIG. 10 shows a configuration for a nested circular imaging scan.

FIG. 10 shows a nested circular imaging scan. A first scan head 1005 may be operated along a first approximately circular path 1010. A second scan head 1015 may be operated along a second approximately circular path 1020. A third scan head 1025 may be operated along a third approximately circular path 1030. A fourth scan head 1035 may be operated along a fourth approximately circular path 1040. A fifth scan head 1045 may be operated along a fifth approximately circular path 1050. A sixth scan head 1055 may be operated along a sixth approximately circular path 1060. Each of the first, second, third, fourth, fifth, and sixth scan heads may be independently clocked. Each of the first, second, third, fourth, fifth, and sixth scan heads may comprise any optical systems described herein. Each of the first, second, third, fourth, fifth, and sixth scan heads may be configured to remain in a fixed location during scanning of a substrate. Alternatively, one or more of the first, second, third, fourth, fifth, and sixth scan heads may be configured to move during scanning of a substrate. The use of a plurality of scan heads imaging along approximately circular imaging paths may greatly increase imaging throughput. For instance, the configuration of scan heads depicted in FIG. 10 may allow all addressable locations on a substrate to be imaged during a single rotation of the substrate. Such a configuration may have the additional advantage of simplifying the mechanical complexity of an imaging system by requiring only one scanning motion (e.g., the rotation of the substrate).

While FIG. 10 illustrates six imaging paths and six scan heads, there may be any number of imaging paths and any number of scan heads. For example, there may be at least about 2, 3, 4, 5, 6, 7, 8, 9, 10, or more imaging paths or scan heads. Alternatively, there may be at most about 10, 9, 8, 7, 6, 5, 4, 3, 2, or less imaging paths or scan heads. Each scan head may be configured to receive light having a wavelength within a given wavelength range. For instance, the first scan head may be configured to receive first light having a wavelength within a first wavelength range. The second scan head may be configured to receive second light having a wavelength within a second wavelength range. The third scan head may be configured to receive third light having a wavelength within a third wavelength range. The fourth scan head may be configured to receive fourth light having a wavelength within a fourth wavelength range. The fifth scan head may be configured to receive fifth light having a wavelength within a fifth wavelength range. The sixth scan head may be configured to receive sixth light having a wavelength within a sixth wavelength range. Similarly, seventh, eighth, ninth, or tenth scan heads may be configured to receive seventh, eighth, ninth, or tenth light, respectively, each of the seventh, eighth, ninth, or tenth light having a wavelength within a seventh, eighth, ninth, or tenth wavelength range, respectively. The first, second, third, fourth, fifth, sixth, seventh, eighth, ninth, or tenth wavelength ranges may be identical. The first, second, third, fourth, fifth, sixth, seventh, eighth, ninth, or tenth wavelength ranges may partially overlap. Any 2, 3, 4, 5, 6, 7, 8, 9, or 10 of the first, second, third, fourth, fifth, sixth, seventh, eighth, ninth, or tenth wavelength ranges may be distinct. The first, second, third, fourth, fifth, sixth, seventh, eighth, ninth, or tenth wavelength ranges may be in the ultraviolet, visible, or near infrared regions of the electromagnetic spectrum. Each of the first, second, third, fourth, fifth, sixth, seventh, eighth, ninth, or tenth wavelength ranges may comprise a wavelength emitted by a fluorophore, dye, or quantum dot described herein. In this manner, the system may be configured to detect optical signals from a plurality of fluorophores, dyes, or quantum dots.

Figure 11:
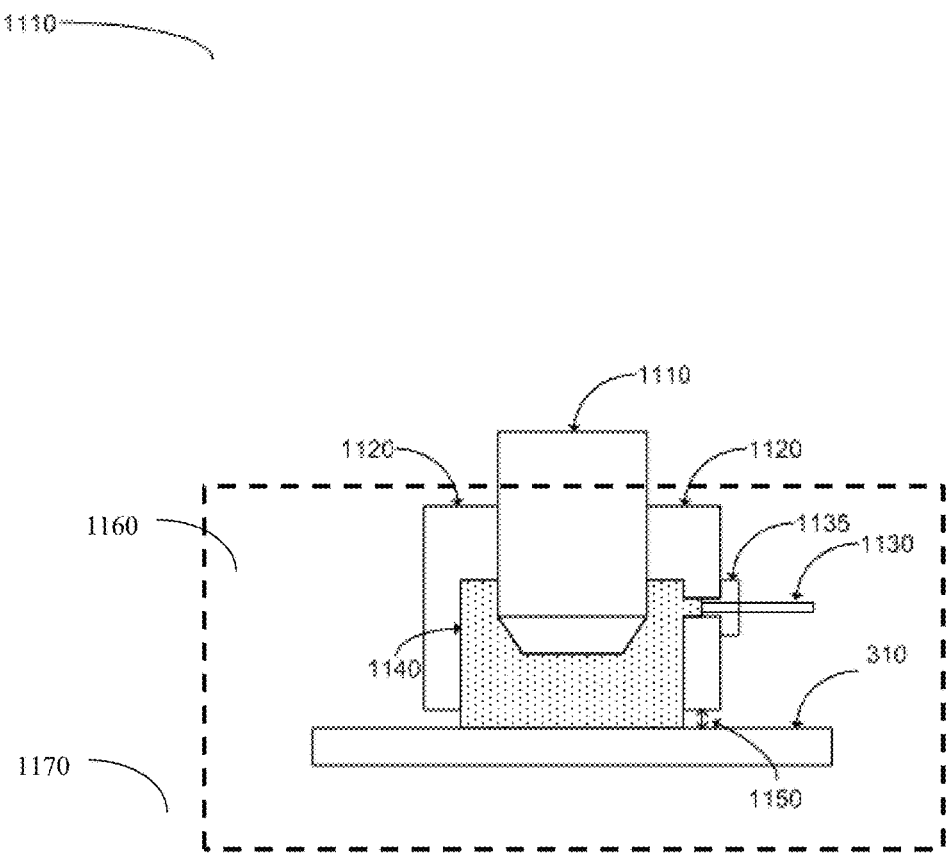
FIG. 11 shows a cross-sectional view of an immersion optical system.

FIG. 11 shows a cross-sectional view of an immersion optical system 1100. The system 1100 may be used to optically image the substrates described herein. The system 1100 may be integrated with any other optical system or system for nucleic acid sequencing described herein (such as any of systems 300, 400, 500a, 500b, 700, or 800), or any element thereof. The system may comprise an optical imaging objective 1110. The optical imaging objective may be an immersion optical imaging objective. The optical imaging objective may be configured to be in optical communication with a substrate, such as substrate 310 described herein. The optical imaging objective may be configured to be in optical communication with any other optical elements described herein. The optical imaging objective may be partially or completely surrounded by an enclosure 1120. The enclosure may partially or completely surround a sample-facing end of the optical imaging objective. The enclosure and fluid may comprise an interface between the atmosphere in contact with the substrate and the ambient atmosphere. The atmosphere in contact with the substrate and the ambient atmosphere may differ in relative humidity, temperature, and/or pressure. The enclosure may have a generally cup-like shape or form. The enclosure may be any container. The enclosure may be configured to contain a fluid 1140 (such as water or an aqueous or organic solution) in which the optical imaging objective is to be immersed. The enclosure may be configured to maintain a minimal distance 1150 between the substrate and the enclosure in order to avoid contact between the enclosure and the substrate during rotation of the substrate. The minimal distance may be at least 100 nm, at least 200 nm, at least 500 nm, at least 1 µm, at least 2 µm, at least 5 µm, at least 10 µm, at least 20 µm, at least 50 µm, at least 100 µm, at least 200 µm, at least 500 µm, at least 1 mm, or a distance that is within a range defined by any two of the preceding values. Even with a minimal distance, the enclosure may contain the fluid due to surface tension effects. The system may comprise a fluid flow tube 1130 configured to deliver fluid to the inside of the enclosure. The fluid flow tube may be connected to the enclosure through an adaptor 1135. The adaptor may comprise a threaded adaptor, a compression adaptor, or any other adaptor. An electrical field application unit (not shown) can be configured to regulate a hydrophobicity of one or more surfaces of a container to retain at least a portion of the fluid contacting the immersion objective lens and the open substrate, such as by applying an electrical field.

The fluid may be in contact with the substrate. The optical imaging objective and enclosure may be configured to provide a physical barrier between a first location in which chemical processing operations are performed and a second location in which detection operations are performed. In this manner, the chemical processing operations and the detection operations may be performed with independent operation conditions and contamination of the detector may be avoided. The first and second locations may have different humidities, temperatures, pressures, or atmospheric admixtures.

A system of the present disclosure may be contained in a container or other closed environment. For example, a container may isolate an internal environment 1160 from an external environment 1170. The internal environment 1160 may be controlled such as to localize temperature, pressure, and/or humidity, as described elsewhere herein. In some instances, the external environment 1170 may be controlled. In some instances, the internal environment 1160 may be further partitioned, such as via, or with aid of, the enclosure 1120 to separately control parts of the internal environment (e.g., first internal environment for chemical processing operations, second internal environment for detection operations, etc.). The different parts of the internal environment may be isolated via a seal. For example, the seal may comprise the immersion objective described herein.

System Architectures for High-Throughput Processing

The nucleic acid sequencing systems and optical systems described herein (or any elements thereof) may be combined in a variety of architectures.

Figure 12A:
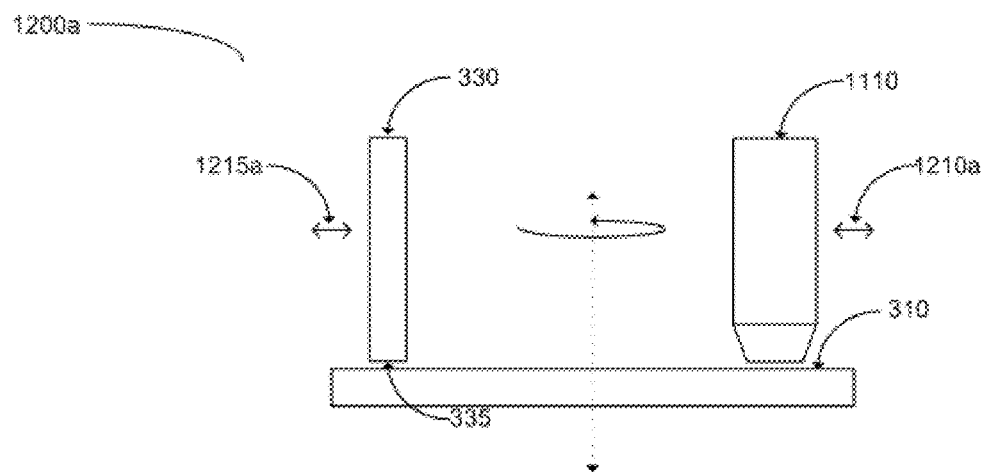
FIG. 12A shows an architecture for a system comprising a stationary axis substrate and moving fluidics and optics.

FIG. 12A shows an architecture for a system 1200a comprising a stationary substrate and moving fluidics and optics. The system 1200a may comprise substrate 310 described herein. The substrate may be configured to rotate, as described herein. The substrate may be adhered or otherwise affixed to a chuck (not shown in FIG. 12A), as described herein. The system may further comprise fluid channel 330 and fluid outlet port 335 described herein, and/or any other fluid channel and fluid outlet port described herein. The fluid channel and fluid outlet port may be configured to dispense any solution described herein. The fluid channel and fluid outlet port may be configured to move 1215a relative to the substrate. For instance, the fluid channel and fluid outlet port may be configured to move to a position above (such as near the center of) the substrate during periods of time in which the fluid channel and fluid outlet port are dispensing a solution. The fluid channel and fluid outlet port may be configured to move to a position away from the substrate during the period in which the fluid channel and fluid outlet port are not dispensing a solution. Alternatively, the reverse may apply. The system may further comprise optical imaging objective 1110 described herein. The optical imaging objective may be configured to move 1210a relative for the substrate. For instance, the optical imaging objective may be configured to move to a position above (such as near the center of) the substrate during periods of time in which the substrate is being imaged. The optical imaging objective may be configured to move to a position away from the substrate during the period in which the substrate is not being imaged. The system may alternate between dispensing of solutions and imaging, allowing rapid sequencing of the nucleic acids attached to the substrate using the systems and methods described herein.

Figure 12B:
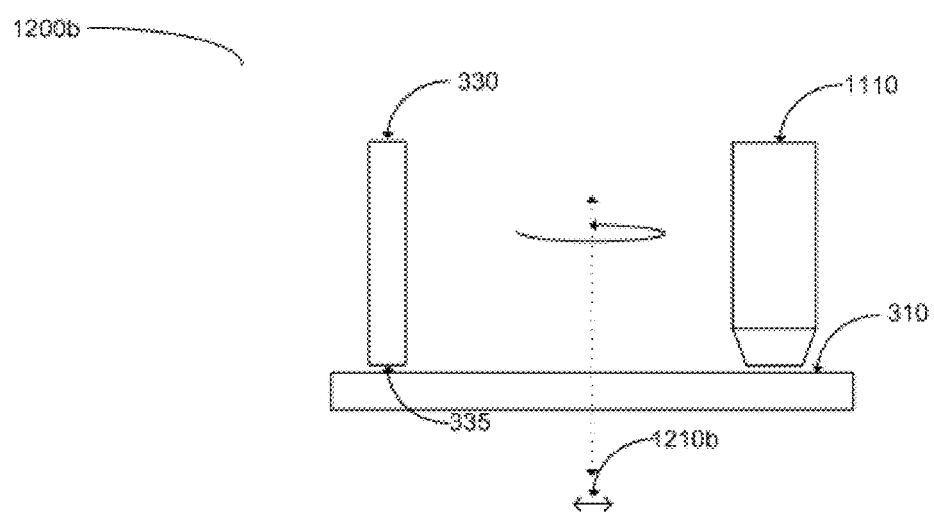
FIG. 12B shows an architecture for a system comprising a translating axis substrate and stationary fluidics and optics.

FIG. 12B shows an architecture for a system 1200b comprising a moving substrate and stationary fluidics and optics. The system 1200b may comprise substrate 310 described herein. The substrate may be configured to rotate, as described herein. The substrate may be adhered or otherwise affixed to a chuck (not shown in FIG. 12B), as described herein. The system may further comprise fluid channel 330 and fluid outlet port 335 described herein, or any other fluid channel and fluid outlet port described herein. The fluid channel and fluid outlet port may be configured to dispense any solution described herein. The system may further comprise optical imaging objective 1110 described herein. The fluid channel, fluid outlet port, and optical imaging objective may be stationary. The substrate may be configured to move 1210b relative to the fluid channel, fluid outlet port, and optical imaging objective. For instance, the substrate may be configured to move to a position such that the fluid channel and fluid outlet port are above (such as near the center of) the substrate during periods of time in which the fluid channel and fluid outlet port are dispensing a solution. The substrate may be configured to move to a position away from the fluid channel and fluid outlet port during the period in which the fluid channel and fluid outlet port are not dispensing a solution. The substrate may be configured to radially scan the objective over the substrate during periods of time in which the substrate is being imaged. The substrate may be configured to move to a position away from the optical imaging objective during the period in which the substrate is not being imaged. The system may alternate between dispensing of solutions and imaging, allowing rapid sequencing of the nucleic acids attached to the substrate using the systems and methods described herein.

Figure 12C:
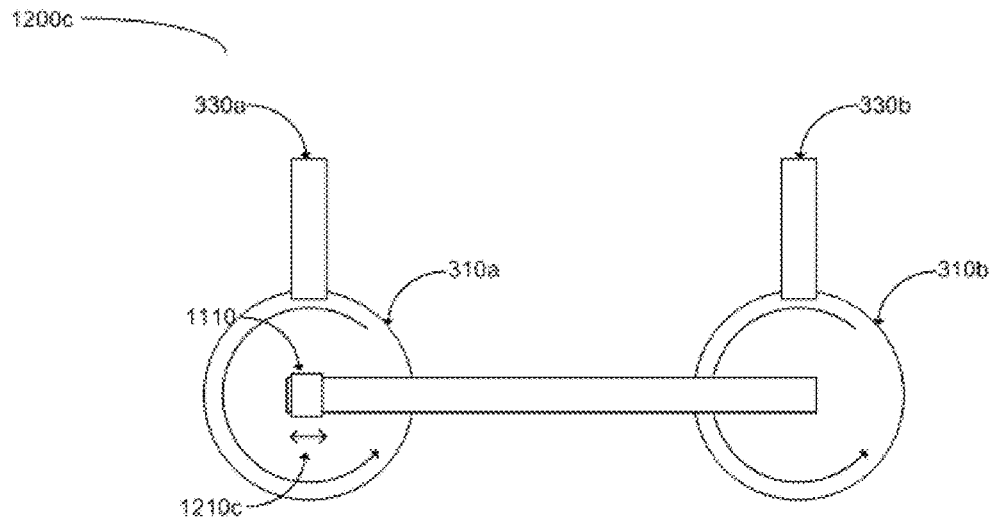
FIG. 12C shows an architecture for a system comprising a plurality of stationary substrates and moving fluidics and optics.

FIG. 12C shows an architecture for a system 1200c comprising a plurality of stationary substrates and moving fluidics and optics. The system 1200c may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12C), as described herein. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The system may further comprise second fluid channel 330b and second fluid outlet port 335b. Second fluid channel 330b may be similar to fluid channel 330 described herein or any other fluid channel described herein. Second fluid outlet port 335a may be similar to fluid outlet port 335 described herein or any other fluid outlet port described herein. The first fluid channel and first fluid outlet port may be configured to dispense any solution described herein. The second fluid channel and second fluid outlet port may be configured to dispense any solution described herein.

The system may further comprise optical imaging objective 1110. Optical imaging objective 1110 may be configured to move 1210c relative to the first and second substrates. For instance, the optical imaging objective may be configured to move to a position above (such as near the center of, or radially scanning) the first substrate during periods of time in which the first fluid channel and first fluid outlet port are not dispensing a solution to the second substrate (and during which the first substrate is to be imaged). The optical imaging objective may be configured to move to a position away from the first substrate during the period in which the first fluid channel and first fluid outlet port are dispensing a solution. The optical imaging objective may be configured to move to a position above (such as near the center of, or radially scanning) the second substrate during periods of time in which the second fluid channel and second fluid outlet port are not dispensing a solution to the second substrate (and during which the second substrate is to be imaged). The optical imaging objective may be configured to move to a position away from the second substrate during the period in which the second fluid channel and second fluid outlet port are dispensing a solution.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the optical imaging objective may be moved from the second substrate to the first substrate. A solution may then be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 12C, system 1200c may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and/or at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. Each optical imaging objective may be moved between substrates as described herein.

Figure 12D:
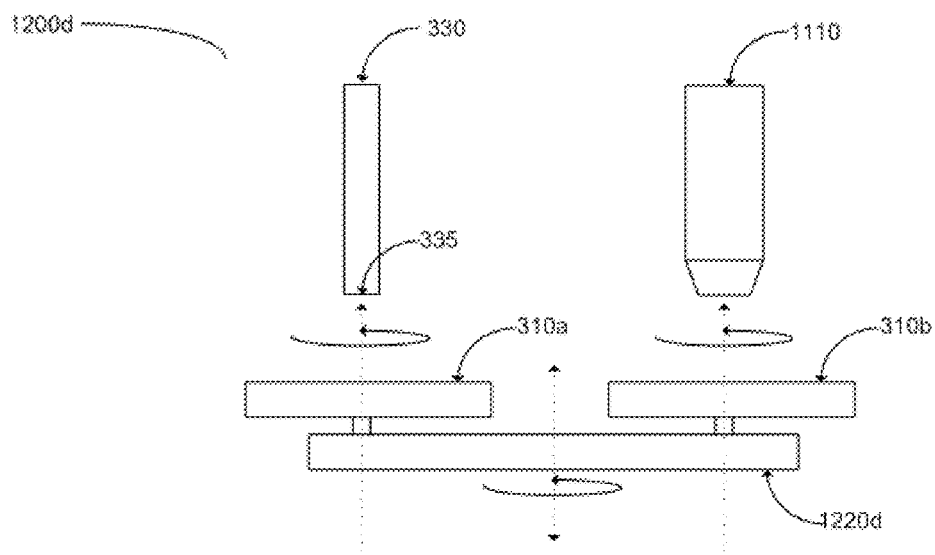
FIG. 12D shows an architecture for a system comprising a plurality of moving substrates on a rotary stage and stationary fluidics and optics.

FIG. 12D shows an architecture for a system 1200d comprising a plurality of moving substrates on a rotary stage and stationary fluidics and optics. The system 1200d may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12D), as described herein. The first and second substrates may be affixed to a rotating stage 1220d (such as approximately at opposing ends of the rotating stage). The rotating stage may be configured to rotate about an axis. The axis may be an axis through the center of the substrate. The axis may be an off-center axis. The rotating stage may approximately scan the radius of the substrate 310b. The system may further comprise fluid channel 330 and fluid outlet port 335. The fluid channel and fluid outlet port may be configured to dispense any solution described herein. The system may further comprise optical imaging objective 1110. A longitudinal axis of the imaging objective 1110 may not be coincident with a central axis of the second substrate 310b (although this is difficult to distinguish in FIG. 12D). The imaging objective 1110 may be positioned at some distance from a center of the second substrate 310b.

The rotating stage may be configured to alter the relative positions of the first and second substrates to carry out different sequencing operations. For instance, the rotating stage may be configured to rotate such that the optical imaging objective is in a position above (such as near the center of, or radially scanning) the first substrate during periods of time in which the fluid channel and fluid outlet port are not dispensing a solution to the first substrate (and during which the first substrate is to be imaged). The rotating stage may be configured to rotate such that the optical imaging objective is away from the first substrate during the period in which the fluid channel and fluid outlet port are dispensing a solution to the first substrate. The rotating stage may be configured to rotate such that the optical imaging objective is in a position above (such as near the center of, or radially scanning) the second substrate during periods of time in which the fluid channel and fluid outlet port are not dispensing a solution to the second substrate (and during which the second substrate is to be imaged). The rotating stage may be configured to rotate such that the optical imaging objective is away from the second substrate during the period in which the fluid channel and fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the rotating stage may be rotated such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, one fluid channel, one fluid outlet port, and one optical imaging objective in FIG. 12D, system 1200d may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The rotating stage may be rotated to place any substrate under any fluid channel, fluid outlet port, or optical imaging objective at any time.

Figure 12E:
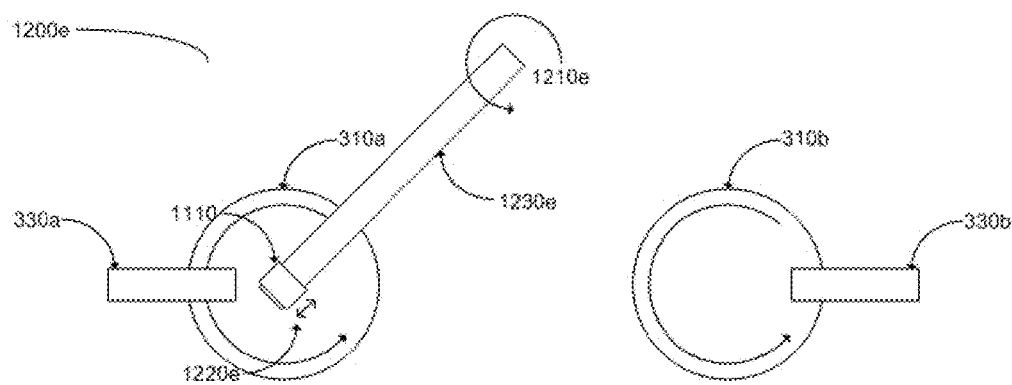
FIG. 12E shows an architecture for a system comprising a plurality of stationary substrates and moving optics.

FIG. 12E shows an architecture for a system 1200e comprising a plurality of stationary substrates and moving optics. The system 1200d may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12E), as described herein. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein.

The system may further comprise optical imaging objective 1110. The optical imaging objective may be attached to an imaging arm 1230e. The optical imaging objective may be configured to move 1220e along the optical imaging arm to image an entire area of the first or second substrate. The optical imaging arm may be configured to rotate 1210e. The optical imaging arm may be configured to rotate such that the optical imaging objective is in a position above (such as near the center of, or radially scanning) the first substrate during periods of time in which the first fluid channel and first fluid outlet port are not dispensing a solution to the first substrate (and during which the first substrate is to be imaged). The optical imaging arm may be configured to rotate such that the optical imaging objective is away from the first substrate during the period in which the first fluid channel and first fluid outlet port are dispensing a solution to the first substrate. The optical imaging arm may be configured to rotate such that the optical imaging objective is in a position above (such as near the center of, or radially scanning) the second substrate during periods of time in which the second fluid channel and second fluid outlet port are not dispensing a solution to the second substrate (and during which the second substrate is to be imaged). The optical imaging arm may be configured to rotate such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the optical imaging arm may be rotated such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 12E, system 1200e may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The optical imaging arm may be rotated to place any substrate under any fluid channel, fluid outlet port, or optical imaging objective at any time.

Figure 12F:
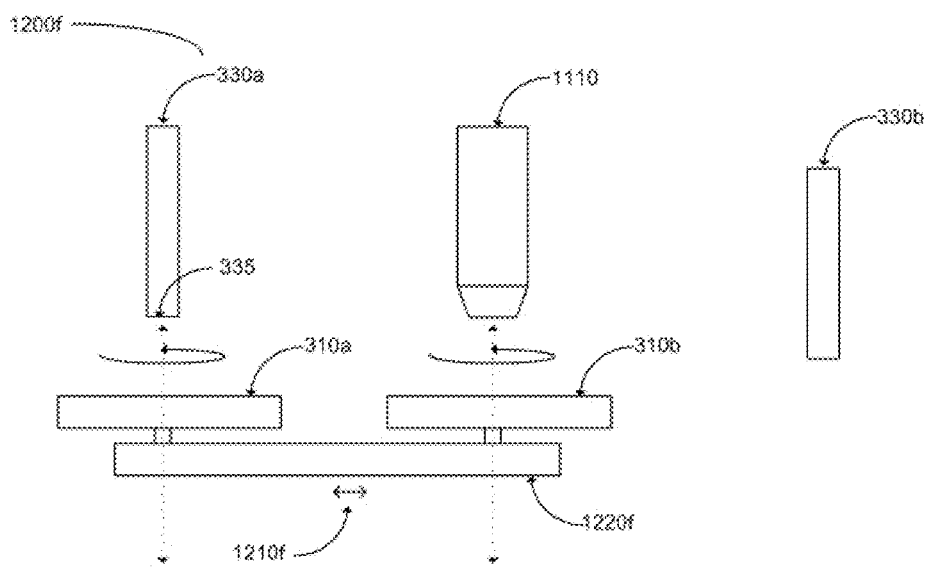
FIG. 12F shows an architecture for a system comprising a plurality of moving substrates and stationary fluidics and optics.

FIG. 12F shows an architecture for a system 1200f comprising a plurality of moving substrates and stationary fluidics and optics. The system 1200f may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12F), as described herein. The first and second substrates may be affixed to opposing ends of a moving stage 1220f. The moving stage may be configured to move 1210f. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein. The system may further comprise optical imaging objective 1110.

The moving stage may be configured to move such that the optical imaging objective is in a position above (such as near the center of, or radially scanning) the first substrate during periods of time in which the first fluid channel and first fluid outlet port are not dispensing a solution to the first substrate (and during which the first substrate is to be imaged). The moving stage may be configured to move such that the optical imaging objective is away from the first substrate during the period in which the first fluid channel and first fluid outlet port are dispensing a solution to the first substrate. The moving stage may be configured to move such that the optical imaging objective is in a position above (such as near the center of, or radially scanning) the second substrate during periods of time in which the second fluid channel and second fluid outlet port are not dispensing a solution to the second substrate (and during which the second substrate is to be imaged). The moving stage may be configured to move such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the moving stage may move such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 12F, system 1200f may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The moving stage may move so as to place any substrate under any fluid channel, fluid outlet port, or optical imaging objective at any time.

Figure 12G:
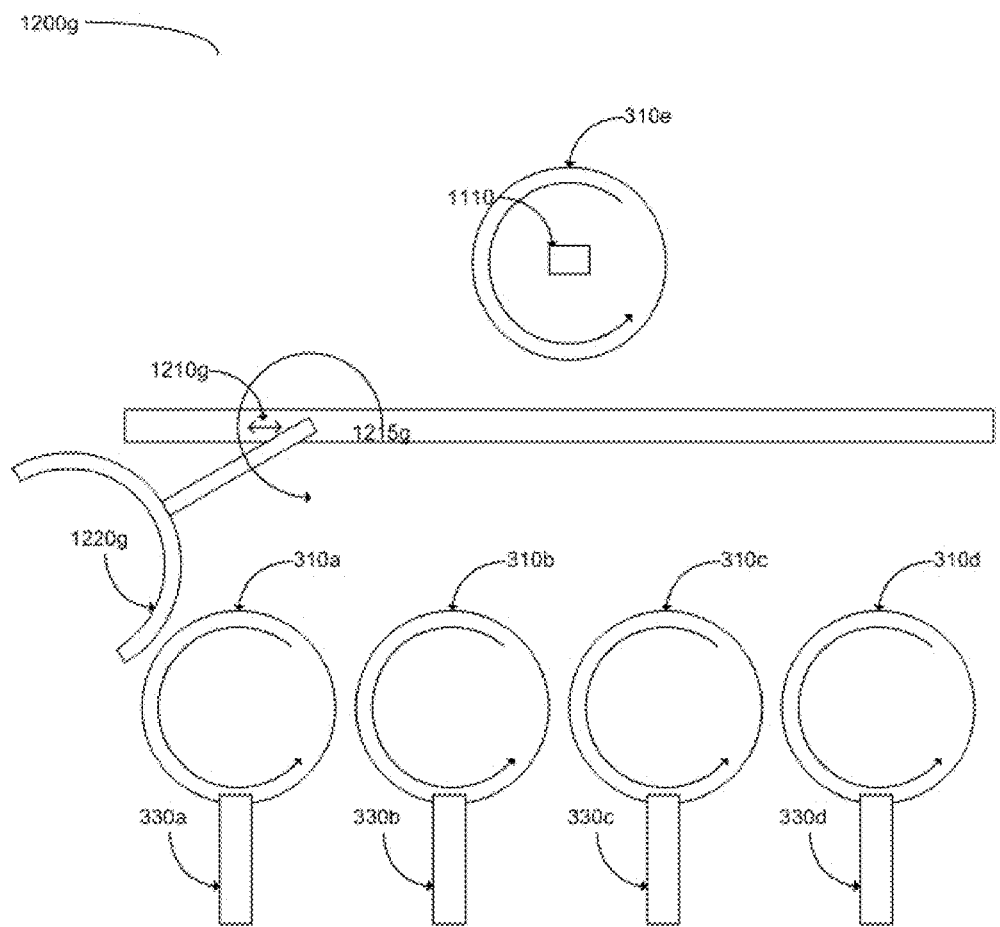
FIG. 12G shows an architecture for a system comprising a plurality of substrates moved between a plurality of processing bays.

FIG. 12G shows an architecture for a system 1200g comprising a plurality of substrates moved between a plurality of processing bays. The system 1200g may comprise first, second, third, and fourth substrates 310a, 310b, 310c, 310d, and 310e, respectively. The first, second, third, fourth, and fifth substrates may be similar to substrate 310 described herein. The first, second, third, fourth, and fifth substrates may be configured to rotate, as described herein. The first, second, third, fourth, and fifth substrates may be adhered or otherwise affixed to first, second, third, fourth, and fifth chucks (not shown in FIG. 12G), respectively, as described herein.

The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The first fluid channel and first fluid outlet port may be regarded as a first processing bay. The first processing bay may be configured to perform a first processing operation, such as dispensing of a first solution to any of the first, second, third, fourth, or fifth substrates.

The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein. The second fluid channel and second fluid outlet port may be regarded as a second processing bay or processing station. The second processing bay may be configured to perform a second processing operation, such as dispensing of a second solution to any of the first, second, third, fourth, or fifth substrates.

The system may further comprise third fluid channel 330c and third fluid outlet port 335c. Third fluid channel 330c may be similar to fluid channel 330 described herein or any other fluid channel described herein. Third fluid outlet port 335c may be similar to fluid outlet port 335 described herein or any other fluid outlet port described herein. The third fluid channel and third fluid outlet port may be configured to dispense any solution described herein. The third fluid channel and third fluid outlet port may be regarded as a third processing bay or processing station. The third processing bay may be configured to perform a third processing operation, such as dispensing of a third solution to any of the first, second, third, fourth, or fifth substrates.

The system may further comprise fourth fluid channel 330d and fourth fluid outlet port 335d. Fourth fluid channel 330d may be similar to fluid channel 330 described herein or any other fluid channel described herein. Fourth fluid outlet port 335d may be similar to fluid outlet port 335 described herein or any other fluid outlet port described herein. The fourth fluid channel and fourth fluid outlet port may be configured to dispense any solution described herein. The fourth fluid channel and fourth fluid outlet port may be regarded as a fourth processing bay or processing station. The fourth processing bay may be configured to perform a fourth processing operation, such as dispensing of a fourth solution to any of the first, second, third, fourth, or fifth substrates.

The system may further comprise a scanning optical imaging objective 1110. The optical imaging objective may be regarded as a fifth processing bay or processing station.

The system may further comprise a moving arm 1220g. The moving arm may be configured to move laterally 1210g or rotate 1215g. The moving arm may be configured to move any of the first, second, third, fourth, or fifth substrates between different processing stations (such as by picking up substrates and moving them to new locations). For instance, at a first point in time, the first substrate may undergo a first operation (such as dispensing of a first solution) at the first processing bay, the second substrate may undergo a second operation (such as dispensing of a second solution) at the second processing bay, the third substrate may undergo a third operation (such as dispensing of a third solution) at the first processing bay, the fourth substrate may undergo a fourth operation (such as dispensing of a fourth solution) at the fourth processing bay, and the fifth substrate may be imaged at the fifth processing bay. Upon completion of one or more of the first, second, third, or fourth operations, or of imaging, the moving arm may move one or more of the first, second, third, fourth, or fifth substrates to one or more of the first, second, third, fourth, or fifth processing bays, where another operation may be completed. The pattern of completing one or more operations and moving one or more substrates to another processing bay to complete another operation may be repeated, allowing rapid sequencing of the nucleic acids attached to the first, second, third, fourth, and fifth substrates using the systems and methods described herein. The alternating pattern of dispensing and imaging may speed up the sequencing by increasing the duty cycle of the imaging process or the solution dispensing process.

Though depicted as comprising five substrates, four fluid channels, four fluid outlet ports, and one optical imaging objective in FIG. 12G, system 1200g may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The moving arm may move so as to place any substrate under any fluid channel, fluid outlet port, or optical imaging objective at any time.

Figure 12H:
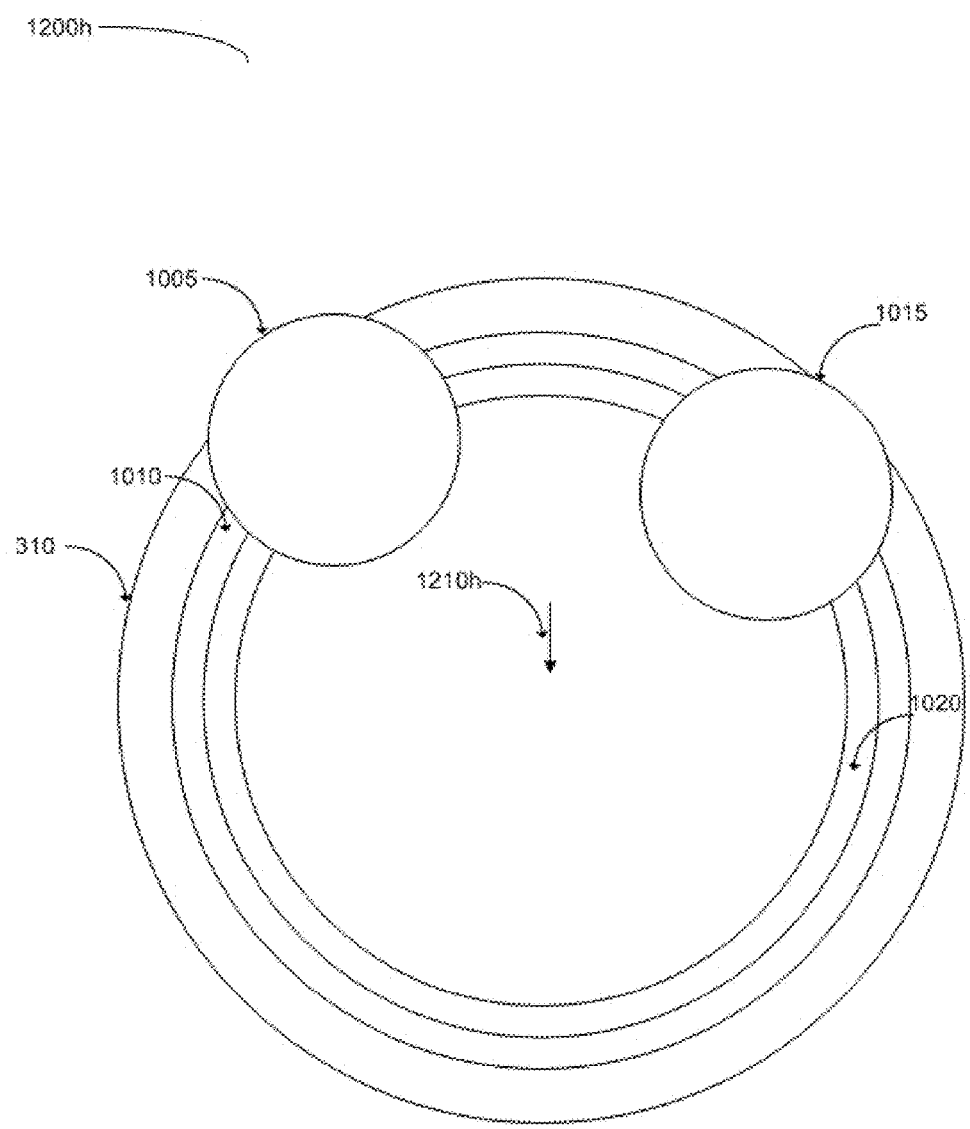
FIG. 12H shows an architecture for a system comprising a plurality of imaging heads scanning with shared translation and rotational axes and independently rotating fields.

FIG. 12H shows an architecture for a system 1200h comprising a plurality of imaging heads scanning with shared translation and rotational axes and independently rotating fields. The system may comprise first and second read heads 1005 and 1015, respectively, configured to image substrate 310. The first and second read heads may be similar to any read head described herein (such as with respect to FIG. 10). At a particular point in time, the first and second read heads may be configured to image first and second paths 1010 and 1020, respectively. The first and second paths may be similar to any paths described herein (such as with respect to FIG. 10). The first and second read heads may be configured to move 1210h in a substantially radial direction over the spinning substrate, thereby scanning the substrate. In the event that either the first or second read head does not move precisely radially, an image field or sensor of the read head may rotate to maintain a substantially tangential scan direction. A field rotation may be accomplished using rotating prisms.

Though depicted as comprising two read heads and two imaging paths in FIG. 12H, system 1200h may comprise any number of read heads or imaging paths. For instance, the system may comprise at least 1, at least 2, at least 3, at least 4, at least 5, at least 6, at least 7, at least 8, at least 9, or at least 10 read heads. The system may comprise at least 1, at least 2, at least 3, at least 4, at least 5, at least 6, at least 7, at least 8, at least 9, or at least 10 imaging paths.

Figure 12I:
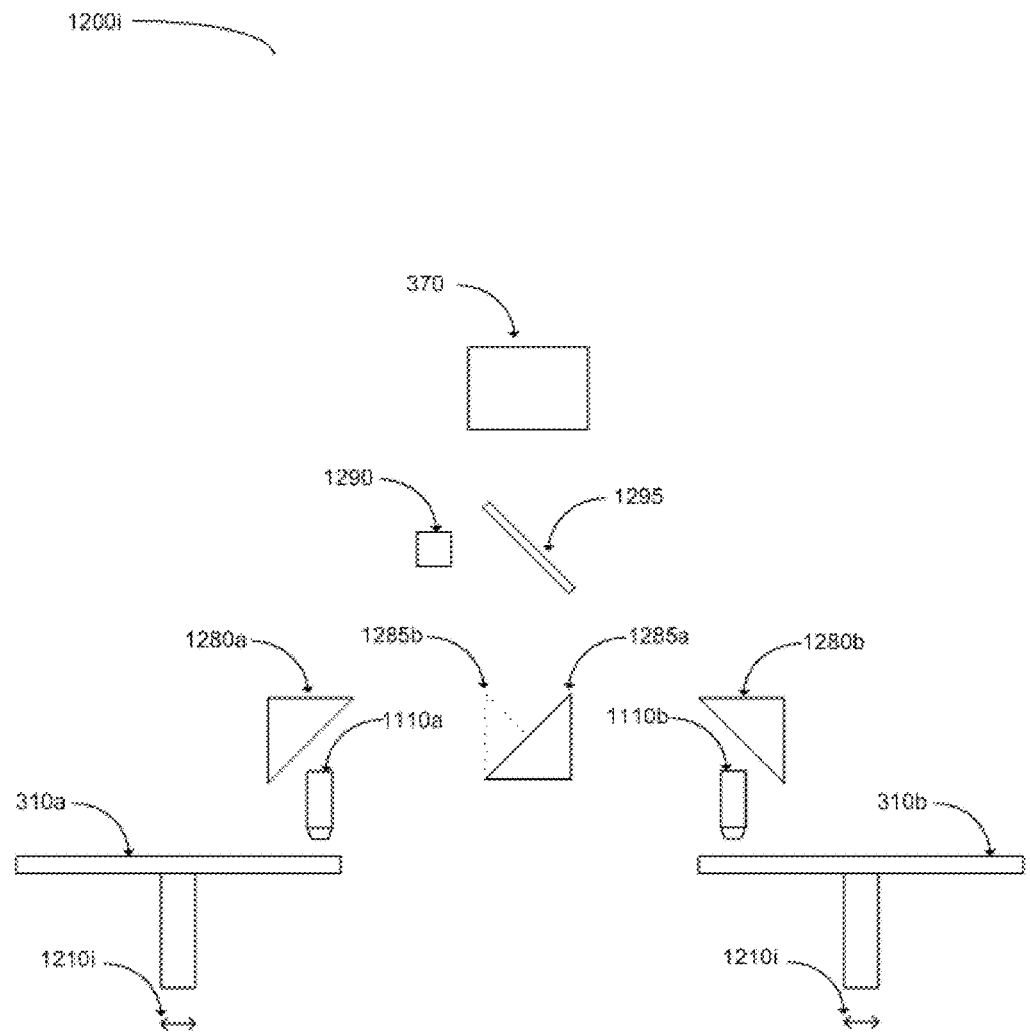
FIG. 12I shows an architecture for a system comprising multiple spindles scanning with a shared optical detection system.

FIG. 12I shows an architecture for a system 1200i comprising multiple spindles scanning with a shared optical detection system. The system may comprise first and second substrates 310a and 310b, respectively. The first and second substrates may be similar to substrate 310 described herein. The first and second substrates may be affixed to first and second spindles, respectively. The first and second spindles may impart rotational motion to the first and second substrates, respectively. The system may comprise first and second optical imaging objectives 1110a and 1110b, respectively. The first and second optical imaging objectives may be similar to optical imaging objective 1110 described herein. The first and second optical imaging objectives may be configured to collect light from the first and second substrates, respectively. The first and second optical imaging objectives may pass light collected from the first and second substrates, respectively, to first and second mirrors 1280a and 1280b, respectively. In some cases, only one of the first and second optical imaging objective will collect light at a particular instance in time.

The first and second mirrors may pass the light to a shared movable mirror. When in a first configuration 1285a, the shared movable mirror may direct light from the first substrate to a beamsplitter 1295. The beamsplitter may comprise a dichroic mirror. The beamsplitter may pass light to a detector 370, allowing the first substrate to be imaged. The first substrate may be configured to be translated 1210i, allowing different locations on the first substrate to be imaged.

When in a second configuration 1285b, the shared movable mirror may direct light from the second substrate to the beamsplitter 1295. The beamsplitter may pass light to a detector 370, allowing the second substrate to be imaged. The second substrate may be configured to be translated 1210i, allowing different locations on the second substrate to be imaged. Thus, by moving the movable mirror, the first and second substrates may be imaged by a shared optical system.

The system may further comprise an excitation light source 1290. The light source may be configured to provide excitation light (such as for fluorescence imaging) to the first or second substrate. The excitation light may be selectively delivered to the first or second substrate using the movable mirror in a similar manner as for detection described herein.

Though depicted as comprising two substrates, two imaging optical objectives, and two mirrors in FIG. 12I, system 1200i may comprise any number of substrates, imaging optical objectives, or mirrors. For instance, the system may comprise at least 1, at least 2, at least 3, at least 4, at least 5, at least 6, at least 7, at least 8, at least 9, or at least 10 substrates. The system may comprise at least 1, at least 2, at least 3, at least 4, at least 5, at least 6, at least 7, at least 8, at least 9, or at least 10 imaging optical objectives. The system may comprise at least 1, at least 2, at least 3, at least 4, at least 5, at least 6, at least 7, at least 8, at least 9, or at least 10 mirrors.

Figure 13:
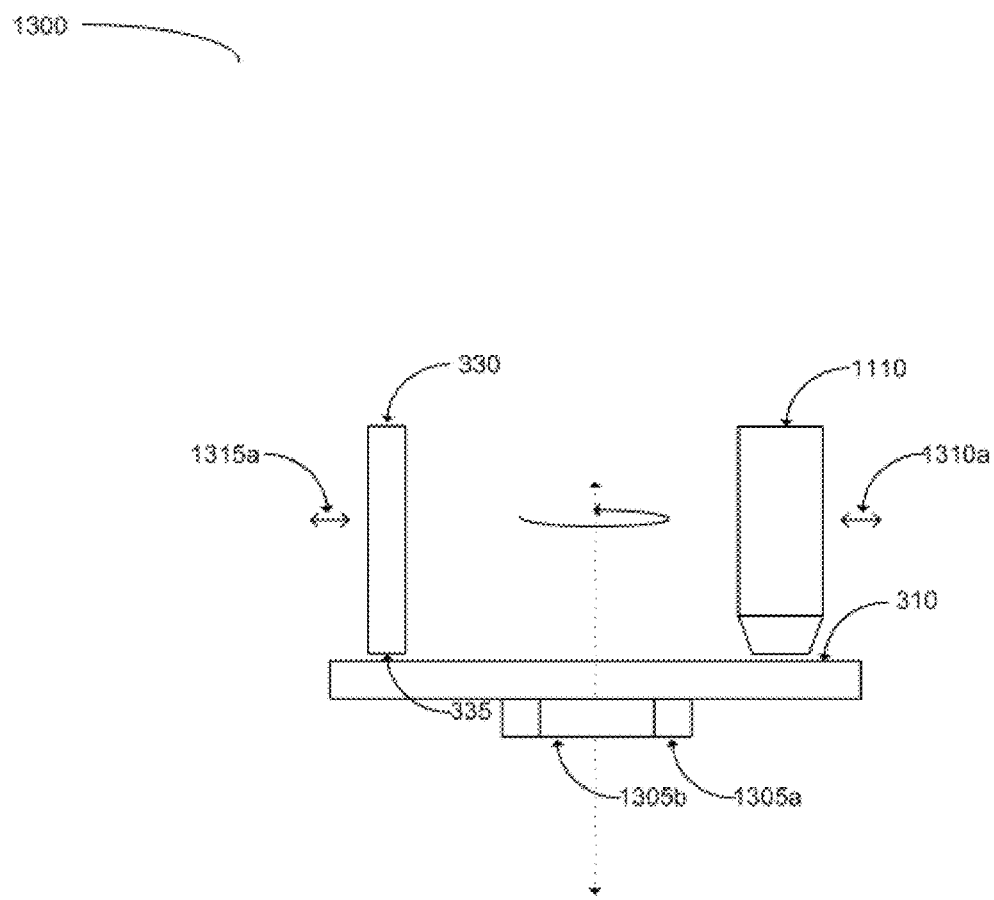
FIG. 13 shows an architecture for a system comprising a plurality of rotating spindles.

FIG. 12H shows an architecture for a system comprising a plurality of imaging heads scanning with shared translation and rotational axes and independently rotating fields;

FIG. 12I shows an architecture for a system comprising multiple spindles scanning with a shared optical detection system FIG. 13 shows an architecture for a system 1300 comprising a plurality of rotating spindles. The system 1300 may comprise substrate 310 described herein. The substrate may be configured to rotate, as described herein. The system may further comprise fluid channel 330 and fluid outlet port 335 described herein, or any other fluid channel and fluid outlet port described herein. The fluid channel and fluid outlet port may be configured to dispense any solution described herein. The fluid channel and fluid outlet port may be configured to move 1315a relative to the substrate. For instance, the fluid channel and fluid outlet port may be configured to move to a position above (such as near the center of) the substrate during periods of time in which the fluid channel and fluid outlet port are dispensing a solution. The fluid channel and fluid outlet port may be configured to move to a position away from the substrate during the period in which the fluid channel and fluid outlet port are not dispensing a solution. The system may further comprise optical imaging objective 1110 described herein. The optical imaging objective may be configured to move 1310a relative for the substrate. For instance, the optical imaging objective may be configured to move to a position above (such as near the center of, or radially scanning) the substrate during periods of time in which the substrate is being imaged. The optical imaging objective may be configured to move to a position away from the substrate during the period in which the substrate is not being imaged.

The system may further comprise a first spindle 1305a and a second spindle 1305b. The first spindle may be interior to the second spindle. The first spindle may be exterior to the second spindle. The second spindle may be interior to the first spindle. The second spindle may be exterior to the first spindle. The first and second spindles may each be configured to rotate independently of each other. The first and second spindles may be configured to rotate with different angular velocities. For instance, the first spindle may be configured to rotate with a first angular velocity and the second spindle may be configured to rotate with a second angular velocity. The first angular velocity may be less than the second angular velocity. The first spindle may be configured to rotate at a relatively low angular velocity (such as an angular velocity between about 0 rpm and about 100 rpm) during periods in which a solution is being dispensed to the substrate. The second spindle may be configured to rotate at a relatively high angular velocity (such as an angular velocity between about 100 rpm and about 1,000 rpm) during periods in which the substrate is being imaged. Alternatively, the reverse may apply. The substrate may be transferred between the first and second spindles to complete each of the dispensing and imaging operations.

The system may comprise any number of spindles. For example, the system may comprise at least about 2, 3, 4, 5, 6, 7, 8, 9, 10, 20, or more spindles. Alternatively or in addition, the system may comprise at most about 20, 10, 9, 8, 7, 6, 5, 4, 3, 2, or 1 spindle. A given spindle may be interior or exterior relative to one or more other spindles in the system. In some instances, each of the spindles may rotate independently of each other. In some instances, at least a subset of the spindles may rotate independently of each other. In some instances, at least a subset of the spindles may rotate dependently of each other (e.g., simultaneously at the same angular velocity). The spindles may rotate with respect to the same axis or different axes. In some instances, each spindle may rotate with different angular velocities. In some instances, at least a subset of the spindles may rotate with different angular velocities.

Though depicted as utilizing a moving fluid channel and optical imaging objective in FIG. 13, the system 1300 may be configured in other manners as described herein. For instance, the system may be configured such that the fluid channel and optical imaging objective are stationary and the substrate is configured to move. The system may be configured in any other manner described herein.

Application to Other Analytes

Figure 14:
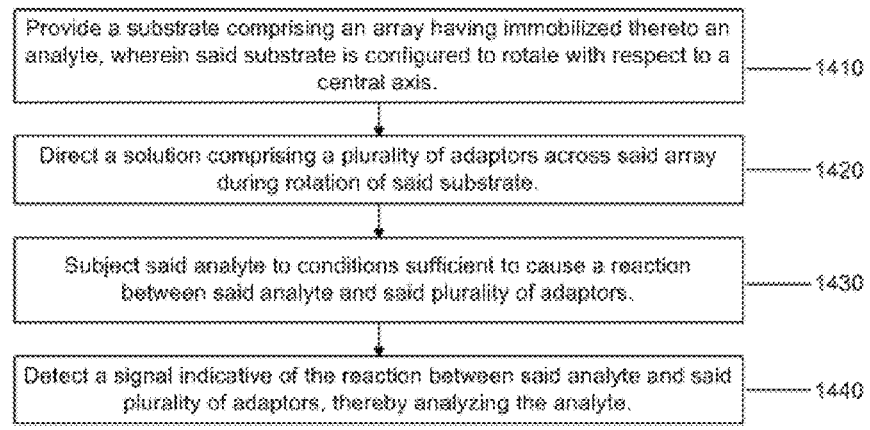
FIG. 14 shows a flowchart for a method for processing an analyte.

Though described herein as useful for sequencing nucleic acids, the systems and method described herein may be applied to other analytes and/or other applications processing such analytes. FIG. 14 shows a flowchart for a method 1400 for processing an analyte.

In a first operation 1410, the method may comprise providing a substrate comprising a planar array having immobilized thereto an analyte, wherein the substrate is configured to rotate with respect to an axis. The axis may be an axis through the center of the substrate. The axis may be an off-center axis. The substrate may be any substrate described herein. In some instances, the planar array may comprise a single type of analyte. In other instances, the planar array may comprise two or more types of analytes. The two or more types of analytes may be arranged randomly. The two or more types of analytes may be arranged in a regular pattern. The analyte may be any biological sample described herein or derivative thereof. For example, the analyte may be a single cell analyte. The analyte may be a nucleic acid molecule. The analyte may be a protein molecule. The analyte may be a single cell. The analyte may be a particle. The analyte may be an organism. The analyte may be part of a colony. In some cases, the analyte may be or be derived from a non-biological sample. The analyte may be immobilized in an individually addressable location on the planar array. The analyte may be immobilized to the substrate via a linker configured to bind to the analyte. For example, the linker may comprise a carbohydrate molecule. The link may comprise an affinity binding protein. The linker may be hydrophilic. The linker may be hydrophobic. The linker may be electrostatic. The linker may be labeled. The linker may be integral to the substrate. The linker may be an independent layer on the substrate.

In a second operation 1420, the method may comprise directing a solution comprising a plurality of adaptors across the planar array during rotation of the substrate. The solution may comprise any solution or reagent described herein. The plurality of adaptors may be configured to interact with the analyte immobilized to the planar array. For example, where the analyte is a nucleic acid molecule, the plurality of adaptors may comprise a plurality of probes. A given probe of the plurality of probes may comprise a random sequence or a targeted sequence, such as a homopolymer sequence or a dibase or tribase repeating sequence. In some instances, the probe may be a dibase probe. In some instances, the probe may be about 1 to 10 bases in length. In some instances, the probe may be about 10 to 20 bases in length. In some instances, the probe may be at least about 1, 2, 3, 4, 5, 6, 7, 8, 9, 10, 11, 12, 13, 14, 15, 16, 17, 18, 19, 20, 30, 40, 50, or more bases. Alternatively or in combination the probe may be at most about 50, 40, 30, 20, 19, 18, 17, 16, 15, 14, 13, 12, 11, 10, 9, 8, 7, 6, 5, 4, 3, 2, 1 base. In another example, where the analyte is a protein molecule, the plurality of adaptors may comprise a plurality of antibodies. A given antibody of the plurality of antibodies may have binding specificity to one or more types of proteins. In other instances, the plurality of adaptors may comprise any combination of a plurality of oligonucleotide molecules, carbohydrate molecules, lipid molecules, affinity binding proteins, aptamers, antibodies, enzymes, or other reagents. The plurality of adaptors may be hydrophilic. The plurality of adaptors may be hydrophobic. The plurality of adaptors may be electrostatic. The plurality of adaptors may be labeled. The plurality of adaptors may comprise a mixture of labeled and unlabeled components. In some instances, the plurality of adaptors may not be labeled.

In an operation 1430, the method may comprise subjecting the analyte to conditions sufficient to cause a reaction between the analyte and the plurality of adaptors. In an operation 1440, the method may comprise detecting a signal indicative of the reaction between the analyte and the plurality of adaptors, thereby analyzing the analyte.

The method may further comprise, prior to operation 1410, directing the analyte across the substrate comprising the linker. For example, prior to or during dispensing of the analyte, the substrate may be rotated to coat the substrate surface and/or the planar array with the analyte. In some instances, the analyte may be coupled to a bead, which bead is immobilized to the planar array.

The method may further comprise recycling, as described elsewhere herein, a subset of the solution that has contacted the substrate. The recycling may comprise collecting, filtering, and reusing the subset of the solution. The filtering may comprise molecular filtering. The molecular filtering may comprise specific nucleic acid filtering (i.e. filtering for a specific nucleic acid). The nucleic acid filtering may comprise exposure of the solution to an array of oligonucleotide extension compounds which may specifically bind to contaminant nucleotides or nucleic acids.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal. The signal may be any detectable signal. Alternatively or in addition to the optical sensors described herein, the system may comprise one or more other detectors (e.g., acoustic detector, etc.) configured to detect the detectable signal.

In some instances, the method may further comprise, prior to operation 1420, subjecting the substrate to rotation with respect to the central axis.

In some instances, the method may further comprise terminating rotation of the substrate prior to detecting the signal in operation 1440. In other instances, the signal may be detected in operation 1440 while the substrate is rotating.

The signal may be generated by binding of a label to the analyte. The label may be bound to a molecule, particle, cell, or organism. The label may be bound to the molecule, particle, cell, or organism prior to operation 1410. The label may be bound to the molecule, particle, cell, or organism subsequent to operation 1410. The signal may be generated by formation of a detectable product by a chemical reaction. The reaction may comprise an enzymatic reaction. The signal may be generated by formation of a detectable product by physical association. The signal may be generated by formation of a detectable product by proximity association. The proximity association may comprise Förster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. For example, the reaction may comprise a hybridization reaction or ligation reaction. The reaction may comprise a hybridization reaction and a ligation reaction.

The method may further comprise repeating operations 1420, 1430, and 1440 one or more times. Different solutions may be directed to the planar array during rotation of the substrate for consecutive cycles.

Many variations, alterations, and adaptations based on the method 1400 provided herein are possible. For example, the order of the operations of the method 1400 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated. Some of the operations may be manual.

Figure 15:
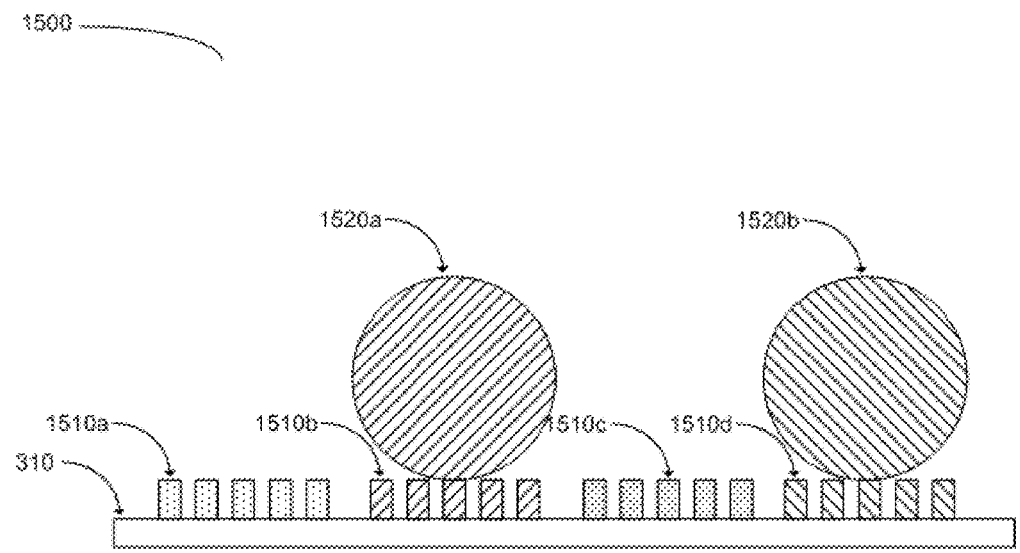
FIG. 15 shows a first example of a system for isolating an analyte.

FIG. 15 shows a first example of a system 1500 for isolating an analyte. The system may comprise a plurality of linkers 1510a, 1510b, 1510c, and 1510d. The plurality of linkers may be adhered or otherwise affixed to substrate 310 described herein. For instance, each linker may be bound to a particular individually addressable location of the plurality of individually addressable locations described herein. Linkers 1510a, 1510b, 1510c, and 1510d may comprise any linker described herein. Some or all of linkers 1510a, 1510b, 1510c, and 1510d may be the same. Some or all of linkers 1510a, 1510b, 1510c, and 1510d may be different. The linkers may be configured to interact with analytes 1520a and 1520b. For instance, the linkers may be configured to bind to analytes 1520a and 1520b through any interaction described herein. Analytes 1520a and 1520b may comprise any analyte described herein. Analytes 1520a and 1520b may be the same. Analytes 1520a and 1520b may be different. The linkers may be configured to interact specifically with particular analytes and/or types thereof. For instance, linker 1510b may be configured to interact specifically with analyte 1520a. Linker 1510d may be configured to interact specifically with analyte 1520b. Any linker may be configured to interact with any analyte. In this manner, specific analytes may be bound to specific locations on the substrate. Though shown as comprising four linkers and two analytes in FIG. 15, system 1500 may comprise any number of linkers and analytes. For instance, system 1500 may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000 linkers, or a number of linkers that is within a range defined by any two of the preceding values. System 1500 may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000 analytes, or a number of analytes that is within a range defined by any two of the preceding values.

Figure 16:
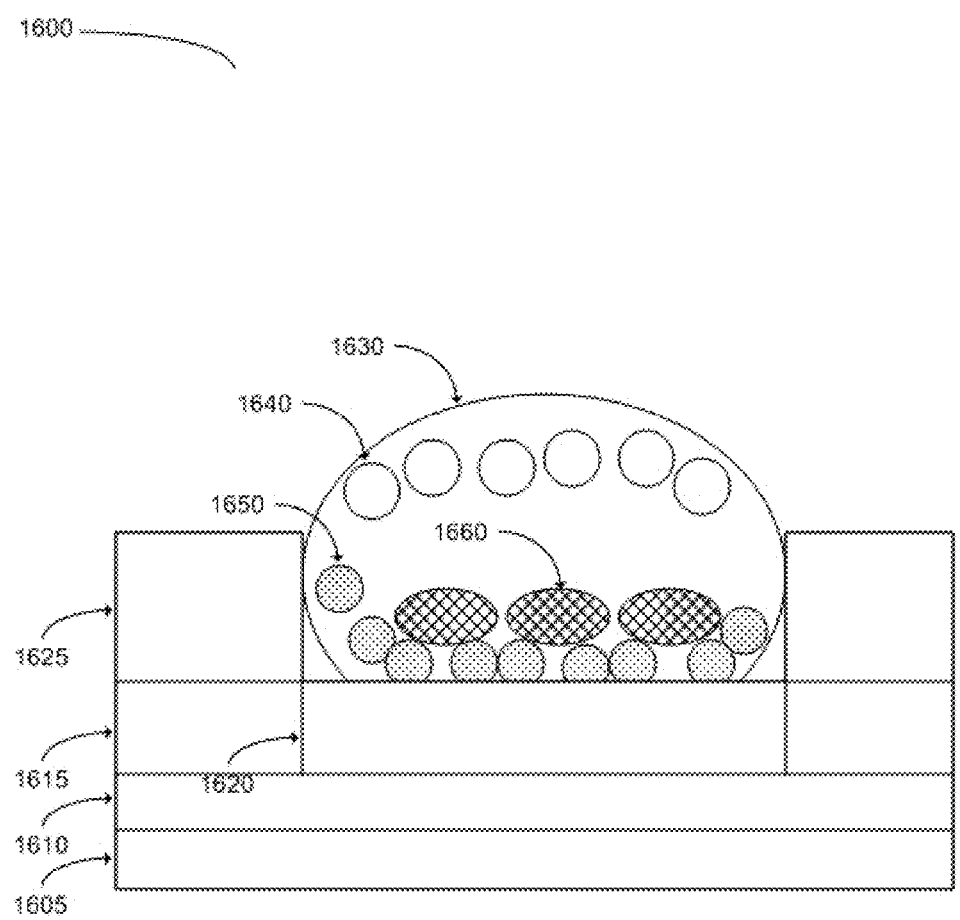
FIG. 16 shows a second example of a system for isolating an analyte.

FIG. 16 shows a second example of a system 1600 for isolating an analyte. The system may comprise a well configured to physically trap a particle. The well may comprise an individually addressable location of the plurality of individually addressable locations described herein. The well may be configured to trap an analyte. For instance, the well may be configured to trap a droplet of blood 1630. For example, the droplet of blood may comprise white blood cells 1640, red blood cells 1650, and circulating tumor cells 1660. The well may be configured to trap any other analyte described herein. The well may be constructed in layers using microfabrication materials and techniques. For instance, the well may comprise a base layer 1605. The base layer may comprise silicon. The well may comprise an oxide layer 1610. The oxide layer may comprise silicon oxide. The well may comprise a metal layer 1615. The metal may comprise nickel or aluminum. The well may comprise a nanotube layer 1620. The nanotube layer may comprise one or more carbon nanotubes. The well may comprise a confinement layer 1625. The confinement layer may comprise a photoresist. The photoresist may comprise SU-8. The nanotube layer and confinement layer may be configured to together trap the cell.

Figure 17:
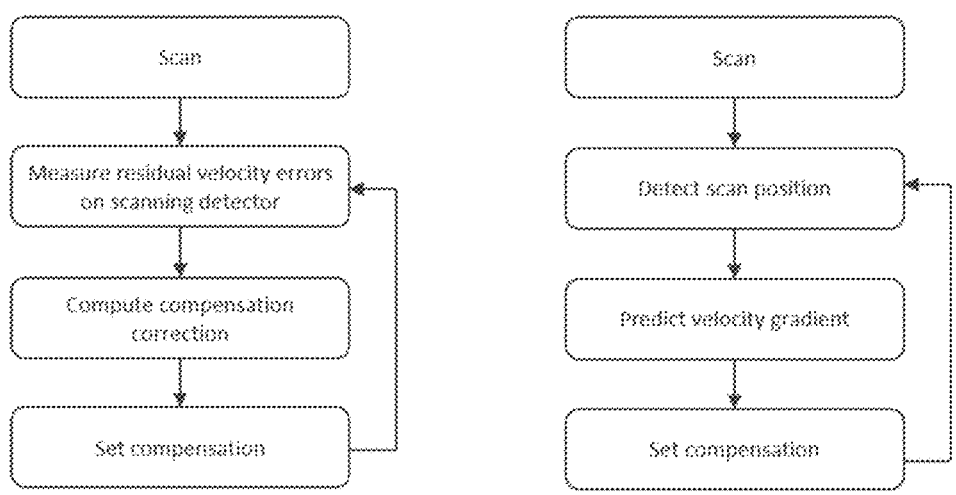
FIG. 17 shows examples of control systems to compensate for velocity gradients during scanning.

FIG. 17 shows examples of control systems to compensate for velocity gradients during scanning. Such control system may algorithmically compensate for velocity gradients. The control system may predictive or adaptively compensate for tangential velocity gradients. In a first control system, illustrated on the left of FIG. 17, the control system may, based on scanning of a rotating substrate, measure residual (uncorrected) velocity errors during scanning, compute a compensation correction factor, and use the compensation correction factor to set (or adjust) a compensation factor to reduce the velocity errors for subsequent scanning results. The first control system may be a closed loop control system that removes (or otherwise reduces) velocity errors. In a second control system, illustrated on the right of FIG. 17, the control system may, based on knowledge of the geometry and relative position of the scanning relative to the substrate, directly compute (or predict) the expected velocity gradient, and set (or adjust) the system to remove the expected gradient.

Computer Control Systems

The present disclosure provides computer control systems that are programmed to implement methods of the disclosure. FIG. 1 shows a computer system 101 that is programmed or otherwise configured to sequence a nucleic acid sample. The computer system 101 can regulate various aspects of methods and systems of the present disclosure.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, nucleic acid sequencing information to a user. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for analyzing a biological analyte, comprising:
   a substrate comprising a first location and a second location, wherein said substrate comprises an array having immobilized thereto said biological analyte at said second location of said substrate, wherein said substrate is configured to rotate with respect to a central axis;
   a fluid flow unit comprising a fluid channel configured to dispense a solution comprising a plurality of probes to said array at said first location of said substrate such that, during rotation of said substrate, said solution is directed centrifugally along a direction away from said central axis from said first location to and in contact with said biological analyte at said second location of said substrate under conditions sufficient to couple at least one probe of said plurality of probes to said biological analyte, wherein said first location is radially closer to said central axis than said second location;
   a rotational unit operatively coupled to said substrate, wherein said rotational unit is configured to subject said substrate to rotation;
   a detector in optical communication with said array, wherein said detector is configured to detect one or more signals from said at least one probe coupled to said biological analyte; and
   one or more computer processors operatively coupled to said fluid flow unit, said rotational unit, and said detector, wherein said one or more computer processors are individually or collectively programmed to (i) direct said rotational unit to subject said substrate to rotation, (ii) direct said fluid flow unit to dispense said solution through said fluid channel to said first location of said substrate such that said solution comprising said plurality of probes is directed centrifugally along a direction away from said central axis from said first location to and in contact with said biological analyte at said second location of said substrate during rotation of said substrate, and (iii) use said detector to detect said one or more signals from said at least one probe coupled to said biological analyte.

2. The system of claim 1, wherein said substrate is movable along said central axis.

3. The system of claim 2, wherein said fluid channel is configured to dispense said solution when said substrate is at a first location along said central axis, and wherein said detector is configured to detect said one or more signals when said substrate is at a second location along said central axis, which second location is different from said first location.

4. The system of claim 3, wherein at said first location, said substrate is rotatable at a first angular velocity and, at said second location, said substrate is rotatable at a second angular velocity that is different than said first angular velocity.

5. The system of claim 1, further comprising an additional fluid channel configured to dispense an additional solution to said array, wherein said fluid channel and said additional fluid channel are fluidically isolated upstream from one another upstream of outlet ports of said fluid channel and said additional fluid channel.

6. The system of claim 1, further comprising an optical imaging objective configured to be at least partially immersed in a fluid in contact with said substrate, which optical imaging objective is in optical communication with said detector.

7. The system of claim 6, further comprising a container encircling said optical imaging objective, which container is configured to retain at least a portion of said fluid.

8. The system of claim 1, wherein said fluid channel does not contact said substrate.

9. The system of claim 1, wherein said array is a substantially planar array.

10. The system of claim 1, wherein said one or more computer processors are individually or collectively programmed to direct said fluid flow unit to dispense said solution through said fluid channel to said array prior to rotation of said substrate.

11. The system of claim 1, wherein said one or more computer processors are individually or collectively programmed to direct said fluid flow unit to dispense said solution through said fluid channel to said array when said substrate is undergoing rotation.

12. The system of claim 1, wherein said detector is configured to detect said one or more signals during rotation of said substrate.

13. The system of claim 12, wherein said detector is configured to continuously scan said array along a nonlinear path during rotation of said substrate.

14. The system of claim 1, wherein said detector is configured to detect said one or more signals when said substrate is not rotating.

15. The system of claim 1, wherein said detector is an optical detector and wherein said one or more signals are one or more optical signals.

16. The system of claim 1, wherein said array comprises a plurality of individually addressable locations.

17. The system of claim 16, wherein said plurality of individually addressable locations are individually physically accessible.

18. The system of claim 1, wherein said substrate is textured or patterned.

19. The system of claim 1, further comprising a container comprising said substrate.

20. The system of claim 19, further comprising an environmental unit that is configured to regulate a temperature or a humidity of an environment of said container.

21. The system of claim 1, wherein said detector comprises a time delay and integration (TDI) sensor or a pseudo-TDI rapid frame rate sensor.

22. The system of claim 1, further comprising an additional detector in optical communication with said array, wherein said detector and said additional detector are configured to scan said array along different paths.

23. The system of claim 22, wherein said different paths are non-linear.

24. The system of claim 1, further comprising one or more optics between, and in optical communication with, said array and said detector, wherein said one or more optics are configured to provide an optical magnification gradient across said array.

25. The system of claim 24, wherein said optical magnification gradient is anamorphic.

26. A system for analyzing a biological analyte, comprising:
a substrate comprising a substantially planar array having a first location and a second location, said substantially planar array having immobilized thereto said biological analyte at said second location of said substantially planar array, wherein said substrate is configured to rotate with respect to a central axis;
a fluid flow unit comprising a fluid channel configured to dispense a solution comprising a plurality of probes to said substantially planar array at said first location of said substantially planar array such that, during rotation of said substrate, said solution is directed across said substantially planar array from said first location to and in contact with said biological analyte at said second location of said substantially planar array under conditions sufficient to couple at least one probe of said plurality of probes to said biological analyte, wherein said first location is radially closer to said central axis than said second location;
a rotational unit operatively coupled to said substrate, wherein said rotational unit is configured to subject said substrate to rotation;
a detector in optical communication with said substantially planar array, wherein said detector is configured to detect one or more signals from said at least one probe coupled to said biological analyte; and
one or more computer processors operatively coupled to said fluid flow unit, said rotational unit, and said detector, wherein said one or more computer processors are individually or collectively programmed to (i) direct said rotational unit to subject said substrate to rotation, (ii) direct said fluid flow unit to dispense said solution through said fluid channel to said first location of said substantially planar array such that said solution comprising said plurality of probes is directed across said substantially planar array from said first location to and in contact with said biological analyte at said second location of said substantially planar array during rotation of said substrate, and (iii) use said detector to detect said one or more signals from said at least one probe coupled to said biological analyte.

27. The system of claim 26, further comprising an optical imaging objective configured to be at least partially immersed in a fluid in contact with said substrate, which optical imaging objective is in optical communication with said detector.

28. The system of claim 26, wherein said detector comprises a time delay and integration (TDI) sensor or a pseudo-TDI rapid frame rate sensor.

29. The system of claim 26, wherein said detector is configured to detect said one or more signals during rotation of said substrate.

30. The system of claim 29, wherein said detector is configured to continuously scan said array along a nonlinear path during rotation of said substrate.

31. The system of claim 1, wherein said biological analyte is immobilized to said array through one or more binders.

32. The system of claim 1, wherein said array comprises at least 100,000 binders, wherein a binder of said at least 100,000 binders immobilizes said biological analyte to said array.

33. The system of claim 1, wherein said biological analyte is coupled to a bead, which bead is immobilized to said array.

34. The system of claim 1, wherein said biological analyte is a nucleic acid molecule.

35. The system of claim 1, wherein said plurality of probes comprise a plurality of oligonucleotide molecules.

36. The system of claim 1, wherein said plurality of probes comprise a plurality of nucleotides or analogs thereof.

37. The system of claim 1, wherein said one or more computer processors are individually or collectively programmed to direct said rotational unit to subject said substrate to rotation at least at two different angular velocities.

38. The system of claim 1, wherein said one or more computer processors are individually or collectively programmed to direct said rotational unit to subject said substrate to rotation at a first angular velocity during dispensing of said solution and at a second angular velocity during detection of said one or more signals, wherein said first angular velocity and said second angular velocity are different.

39. The system of claim 38, wherein said first angular velocity is greater than said second angular velocity.

40. The system of claim 38, wherein said first angular velocity and said second angular velocity are the same.

41. The system of claim 26, wherein said biological analyte is immobilized to said substantially planar array through one or more binders.

42. The system of claim 26, wherein said substantially planar array comprises at least 100,000 binders, wherein a binder of said at least 100,000 binders immobilizes said biological analyte to said substantially planar array.

43. The system of claim 26, wherein said biological analyte is coupled to a bead, which bead is immobilized to said substantially planar array.

44. The system of claim 26, wherein said biological analyte is a nucleic acid molecule.

45. The system of claim 26, wherein said plurality of probes comprise a plurality of oligonucleotide molecules.

46. The system of claim 26, wherein said plurality of probes comprise a plurality of nucleotides or analogs thereof.

47. The system of claim 26, wherein said one or more computer processors are individually or collectively programmed to direct said rotational unit to subject said substrate to rotation at least at two different angular velocities.

48. The system of claim 26, wherein said one or more computer processors are individually or collectively programmed to direct said rotational unit to subject said substrate to rotation at a first angular velocity during dispensing of said solution and at a second angular velocity during detection of said one or more signals, wherein said first angular velocity and said second angular velocity are different.

49. The system of claim 48, wherein said first angular velocity is greater than said second angular velocity.

50. The system of claim 48, wherein said first angular velocity and said second angular velocity are the same.

* * * * *